(12) United States Patent
Kruse et al.

(10) Patent No.: US 8,012,948 B2
(45) Date of Patent: Sep. 6, 2011

(54) FAS/FASL OR OTHER DEATH RECEPTOR TARGETED METHODS AND COMPOSITIONS FOR KILLING TUMOR CELLS

(75) Inventors: Carol Kruse, San Diego, CA (US); Richard Tritz, San Diego, CA (US)

(73) Assignee: Promising Future, LLC, Hagatna, GU (US)

( * ) Notice: Subject to any disclaimer, the term of this patent is extended or adjusted under 35 U.S.C. 154(b) by 0 days.

(21) Appl. No.: 12/579,259

(22) Filed: Oct. 14, 2009

(65) Prior Publication Data

US 2010/0324116 A1 Dec. 23, 2010

Related U.S. Application Data

(60) Provisional application No. 61/105,550, filed on Oct. 15, 2008, provisional application No. 61/229,231, filed on Jul. 28, 2009.

(51) Int. Cl.
*A01N 43/04* (2006.01)
*A61K 31/70* (2006.01)
*C07H 21/04* (2006.01)

(52) U.S. Cl. .................... 514/44 A; 536/24.5
(58) Field of Classification Search ............. 536/24.5; 514/44
See application file for complete search history.

(56) References Cited

U.S. PATENT DOCUMENTS

| | | | |
|---|---|---|---|
| 2004/0248830 A1* | 12/2004 | Tritz et al. | 514/44 |
| 2005/0119212 A1 | 6/2005 | Haeberli et al. | |
| 2005/0255487 A1* | 11/2005 | Khvorova et al. | 435/6 |
| 2006/0057109 A1 | 3/2006 | Waxman et al. | |
| 2007/0077553 A1* | 4/2007 | Bentwich | 435/5 |
| 2007/0254850 A1 | 11/2007 | Lieberman et al. | |
| 2008/0081791 A1 | 4/2008 | Huang et al. | |
| 2008/0227733 A1 | 9/2008 | Lieberman et al. | |

OTHER PUBLICATIONS

Tritz et al., Catalytic nucleic acid enzymes for the study and development of therapies in the central nervous system, Gene Ther Mol Biol vol. 9, 89-106, 2005.
Tritz et al., siRNA down-regulation of the PATZ1 gene in human glioma cells increases their sensitivity to apoptic stimuli, Cancer Therapy vol. 6, 865-876, 2008.
Gomez et al., Immunoresistant human glioma cell clones selected with alloreactive cytoxic T lymphocytes: downregulation of multiple proapoptic factors, Gene Ther Mol Biol vol. 12, 101-110, 2008.
Tritz et al., FAPP2 gene downregulation increases tumor cell sensitivity to Fas-induced apoptosis, Biochem. Biophys. Res. Comm. (2009), doi:10.1016/j.bbrc.2009.03.126.
PCT, International Search Report, Aug. 13, 2010.

* cited by examiner

*Primary Examiner* — Brian Whiteman
(74) *Attorney, Agent, or Firm* — Themis Law; Franco A. Serafini; David M. Fortner

(57) ABSTRACT

Provided herein are methods and compositions for killing tumor cells. In certain embodiments, compositions can promote apoptosis by down-regulating FAPP2 and PATZ1 products.

22 Claims, 13 Drawing Sheets

FIGURE 5

| Cell Lines | Nontransfected | luc siRNA | FAPP2 siRNA |
|---|---|---|---|
| 1833 | 26.0±1.4 | 19.6±1.5*** | 20.6±0.6 |
| U-87MG | 73.0±1.4 | 73.6±1.1 | 82.6±2.1*** |
| U-373MG | 22.5±0.7 | 21.3±0.6 | 21.0±1.0 |
| U-251MG | 49.5±2.1 | 57.3±3.5*** | 70.0±1.0*** |
| T98G | 48.0±0.0 | 55.0±0.3*** | 63.6±1.5*** |

*** The differences in MFI at $p<0.001$ by 2-way ANOVA.

FAS/FASL OR OTHER DEATH RECEPTOR TARGETED METHODS AND COMPOSITIONS FOR KILLING TUMOR CELLS

RELATED PATENT APPLICATIONS

This patent application claims the benefit of U.S. Provisional Application No. 61/105,550 entitled "METHODS AND COMPOSITIONS FOR INCREASING KILLING OF TUMOR CELLS BY DOWN REGULATING THE PATZ1 GENE" filed Oct. 15, 2008 naming Carol Kruse as an inventor, and claims the benefit of U.S. Provisional Application No. 61/229,231 entitled "FAPP2 TARGETED METHODS AND COMPOSITIONS FOR KILLING TUMOR CELLS," filed Jul. 28, 2009, naming Carol Kruse as an inventor. The entire content of each of these patent applications is hereby incorporated by reference herein, including all text, drawings and tables, in jurisdictions providing for such incorporation.

STATEMENT OF GOVERNMENT SUPPORT

This technology was developed in part with government support under Grant Nos. NIH NS056300. The government has certain rights in this technology.

REFERENCE TO A SEQUENCE LISTING

The sequence listing is ASCII text file 1016200005SequenceListing, created on Jun. 16, 2010 and having 102,787 bytes, is incorporated herein by reference.

FIELD

Provided herein are methods and compositions for killing tumor cells. In certain embodiments, compositions can promote apoptosis by down-regulating FAPP2 and PATZ1 products.

BACKGROUND

Uncontrolled cell growth is a distinguishing feature of tumors and other cancers. Surgical intervention seeks to remove the tumor mass. Various other techniques, such as chemotherapy and radiation, target and kill cancer cells, including those left behind after surgery and those located away from the primary tumor mass. Newer techniques employ the body's own defenses including immunological reactions against the aberrant cells.

In concert with uncontrolled cancer growth, cells often exhibit a failure of programmed cell death, or apoptosis. Healthy cells follow a built-in cycle of cell division, growth, and apoptosis. However, transformation to a cancerous or neoplastic state may give rise to genetic modifications that protect the abnormal cell against the action of molecules that typically trigger apoptosis. Cells normally programmed to die survive and continue to divide, thus propagating the cancer.

SUMMARY

Herein provided is a method for inhibiting proliferation of brain tumor cells, which comprises administering to brain tumor cells a siNA agent that reduces the amount of RNA encoding a Fas/FasL apoptosis gating polypeptide in an amount sufficient to inhibit proliferation of the brain tumor cells. In certain embodiments the Fas/FasL apoptosis gating polypeptide is a FAPP2 polypeptide. In some embodiments the Fas/FasL apoptosis gating polypeptide is a PATZ1 polypeptide.

Also provided herein is a method for treating a brain tumor in a subject, which comprises administering to a subject in need thereof a siNA agent that reduces the amount of RNA encoding a FAPP2 polypeptide or a PATZ1 polypeptide in an amount sufficient to inhibit proliferation of cells in the brain tumor in the subject. In certain embodiments the brain tumor cells may comprise glioma cells and/or human cells. In some embodiments the cells undergo apoptosis.

Further provided is a composition that comprises a glioma cell and a nucleic acid. The nucleic acid may comprise a nucleotide sequence complementary to a RNA encoding a Fas/FasIL gating polypeptide in tumor cells; and a ribozyme activity that reduces the amount of the RNA. In some embodiments the nucleic acid is a ribozyme that cleaves the RNA encoding a FAPP2 or a PATZ1 polypeptide. In certain embodiments the ribozyme is expressed by an expression vector administered to the cells. In some embodiments the ribozyme comprises RNA. The ribozyme may also comprise DNA or a combination of DNA and RNA. The ribozyme may comprise the nucleotide sequence:

```
                                          (SEQ ID NO: 1)
5'-NNNNNNNCUGAUGAGpdpdpdpdCGAANNNNNNNNN-3'
``` where A,G,C,T indicate DNA bases, A,G,C,U indicate RNA bases, A,G,C,U indicate 2' O methyl RNA, and pd indicates propanediol linkage.

Also provided herein is a method for inhibiting proliferation of tumor cells, which comprises administering to brain tumor cells a siNA agent that reduces the amount of RNA encoding a Fas/FasL gating polypeptide in an amount sufficient to inhibit proliferation of the tumor cells. In certain embodiments the composition comprises a nucleotide sequence complementary to a RNA encoding a FAPP2 polypeptide or a PATZ1 polypeptide having siNA activity that reduces the amount of the RNA. The nucleic acid may comprise RNA or DNA or any combination thereof. In some embodiments the nucleic acid may consist of RNA or DNA or any combination thereof. The reduction of FAPP2 polypeptide or PATZ1 polypeptide may sensitize the cells to Fas or FasL mediated apoptosis.

A FAPP2 targeted siRNA may comprise either or both of a phosphorothioate linkage and a 2'-O-methyl modification in some embodiments.

In certain embodiments a FAPP2 targeted siRNA may comprise one or both of the nucleotide sequences:

```
                                         (SEQ ID NO: 26)
               5'-GAUGGAUCUUGUUGGAAAUUU-3'

(SEQ ID NO: 27)
               5'-AUUUCCAACAAGAUCCAUCUU-3'.
```

In some embodiments a FAPP2 targeted siRNA comprises one or both of the nucleotide sequences:

```
                                         (SEQ ID NO: 28)
              5'-GAUGGAUCUUGUUGGAAAUUsU-3'

(SEQ ID NO: 29)
              5'-AUUUCCAACAAGAUCCAUCUsU-3'
``` where s is a phosphorothioate linkage.

In certain embodiments the FAPP2 targeted siRNA comprises one or both of the nucleotide sequences:

5'-Gauggaucuuguuggaaauusu-3' (SEQ ID NO: 30)

5'-AUUUCcAACAAGAUCcAUCUsU-3' (SEQ ID NO: 31)

where s is a phosphorothioate linkage and lowercase nucleotide designations designate a nucleotide having a 2'-O-methyl modification.

Provided also herein is an isolated FAPP2 ribozyme nucleic acid that in some embodiments comprises the nucleotide sequence:

5' ATACTGUCUGAUGAGpdpdpdpdCGAAACTATAATT 3'. (SEQ ID NO: 2)

where A,G,C,T indicate DNA bases, A,G,C,U indicate RNA bases, A,G,C,U indicate 2' O methyl RNA, and pd indicates propanediol linkage.

A PATZ1 targeted siRNA may comprise one or more of the nucleotide sequences:

5'-GUCUAUGGAAGAAAUAGUUUU-3' (SEQ ID NO: 32)

5'-UUACUACUACUACUACUACUU-3" (SEQ ID NO: 33)

In certain embodiments the PATZ1 targeted siRNAi comprises one or both of the nucleotide sequences:

5'-GUCUAUGGAAGAAAUAGUUUsU-3' (SEQ ID NO: 34)

5'-UUACUACUACUACUACUACUsU-3' (SEQ ID NO: 35)

where s is a phosphorothioate linkage.

In some embodiments the PATZ1 targeted siRNA comprises one or both of the nucleotide sequences:

5'-GucuAuGGAAGAAAuAGuuusU-3' (SEQ ID NO: 36)

5'-UuACuACuACuACuACuACUsU-3' (SEQ ID NO: 37)

where s is a phosphorothioate linkage and lowercase nucleotide designations designate a nucleotide having a 2'-O-methyl modification.

In certain embodiments the RNA encoding a FAPP2 polypeptide comprises the nucleotide sequence: (SEQ ID NO: 3)

gccgccugcgaccggcagcucguucgccgcacuuuggaggcuucggc
ugccccuccgacccacguagggcccggacccgggccuccuugugaac
agcgugccggcuucgcccacggguucaccggcuggcugggcuucaa
gcgccgaggccgccgcagugaccccgcccccgggccgaggaugugag
gcgggccgggcgucccacaccgggcccgggcgccgggagugggcgu
cugggcagcgccaggcgauggcccugcugcuggugcuccucgccucu
ugggcccuggggcagugaggggccggcgggcgugggccgaguggcc
gcgggcgccauggaggggugcuguacaaguggaccaacuaucugag
cgguuggcagccucgaugguuccuucucuguggggaauauuguccu
auuaugauucuccugaagaugccuggaaagguugcaaagggagcaua
caaauggcagucugugaaauucaaguucauucuguagauaauacacg
cauggaccugauaaucccuggggaacaguauuucuaccugaaggcca
gaagugggcugaaagacagcgguggcugguggcccugggaucagcc
aaggcuugccugacugacaguaggacccagaaggagaaagaguuugc
ugaaaacacugaaaacuugaaaaccaaaaugucagaacuaagacucu
acugugaccuccuuguucagcaaguagauaaaacaaaagaagugacc
acaacuggugugccaauucugaggagggaauugaugugggaacuuu
gcugaaaucaaccuguaauacuuuucugaagaccuuggaagaaugca
ugcagaucgcaaaugcagccuucaccucugagcugcucuaccgcacu
ccaccaggaucaccucagcuggccaugcucaaguccagcaagaugaa
acauccuauuauaccaauucauaauucauuggaaaggcaaauggagu
ugagcacuugugaaaauggaucuuuaaauauggaaauaaauggugag
gaagaaauccuaaugaaaaauaagaauuccuuauauuugaaaucugc
agagauagacugcagcauaucaagugaggaaaauacagaugauaaua
uaacaguccaaggugaaauaaggaaggaagauggaauggaaaccug
aaaaaucaugacaauaacuugacucagucuggaucagacucaaguug
cucuccggaaugccucugggaggaaggcaaagaaguuaucccaacuu
ucuuuaguaccaugaacacaagcuuuagugacauugaacuucuggaa
gacaguggcauucccacagaagcauucuuggcaucauguuaugcugu
gguuccaguauuagacaaacuuggcccuacaguguuugcuccuguua
agauggaucuuguuggaaauauuaagaaaguaaaucagaaguauaua
accaacaaagaagaguuuaccacucuccagaagauagugcugcacga
aguggaggcggauguagcccagguuaggaacucagcgacugaagccc
ucuuguggcugaagagaggucucaaauuuuugaagggauuuugaca
gaagugaaaauggggagaaggauauccagacagcccuaaauaaugc
auauggaaaacauugcggcaacaccauggcugggguaguucgagggg
uuuuugcgguguaggaaugugggguguagacggaacuccagaaaccau
cauggaccaugaggcaacucugaggauggaagccacacacuaaggac
gguaaagcagaaagaagagcugaaacccugaugauaaagaagcagcc
aauuccguccugcacugcccaccuccagaucucauucaugugaaaca
aagagaaacuuuaucuuguucaagucaaaaaaaaaaaaaaaaaaaaaa or a complement of the foregoing.

In some embodiments the RNA encoding a PATZ1 polypeptide comprises the nucleotide sequence identified by the PATZ1 cDNA accession number transcript variant 2 NM_032050 or a complement of the foregoing.

Further provided herein is a composition that may comprise one or both of the following nucleic acids:

```
                                        (SEQ ID NO: 26)
5'-GAUGGAUCUUGUUGGAAAUUU-3'

(SEQ ID NO: 27)
5'-AUUUCCAACAAGAUCCAUCUU-3'.
```

The term "consist essentially of," and grammatical variants thereof, as used herein with respect to nucleic acid compositions refers to compositions that include one or more materials other than the specified nucleic acid that do not materially affect the basic and novel characteristics of the specified nucleic acid. For example, one or more materials in a composition other than the specified nucleic acid that generally do not covalently modify the nucleic acid. In certain embodiments, one or more materials that do not materially affect the basic and novel characteristics of the specified nucleic acid include, without limitation, a salt, buffer or other like agent.

A composition may consist essentially of one or both of the following nucleic acids in some embodiments:

```
                                        (SEQ ID NO: 26)
5'-GAUGGAUCUUGUUGGAAAUUU-3'

(SEQ ID NO: 27)
5'-AUUUCCAACAAGAUCCAUCUU-3'.
```

In certain embodiments the composition consists of one or both of the following nucleic acids:

```
                                        (SEQ ID NO: 26)
5'-GAUGGAUCUUGUUGGAAAUUU-3'

(SEQ ID NO: 27)
5'-AUUUCCAACAAGAUCCAUCUU-3'.
```

Also provided herein is a composition that comprises one or both of the following nucleic acids:

```
                                        (SEQ ID NO: 28)
5'-GAUGGAUCUUGUUGGAAAUUsU-3'

(SEQ ID NO: 29)
5'-AUUUCCAACAAGAUCCAUCUsU-3'
``` where s is a phosphorothioate linkage.

In certain embodiments the composition consists essentially of one or both of the following nucleic acids:

```
                                        (SEQ ID NO: 28)
5'-GAUGGAUCUUGUUGGAAAUUsU-3'

(SEQ ID NO: 29)
5'-AUUUCCAACAAGAUCCAUCUsU-3'
``` where s is a phosphorothioate linkage.

In some embodiments the composition may consist of one or both of the following nucleic acids:

```
                                        (SEQ ID NO: 28)
5'-GAUGGAUCUUGUUGGAAAUUsU-3'

(SEQ ID NO: 29)
5'-AUUUCCAACAAGAUCCAUCUsU-3'
``` where s is a phosphorothioate linkage.

Herein provided is a composition that comprises one or both of the following nucleic acids:

```
                                        (SEQ ID NO: 30)
5'-GAuGGAucuuGuuGGAAAuusu-3'

(SEQ ID NO: 31)
5'-AUUUCcAACAAGAUCcAUCUsU-3'
``` where s is a phosphorothioate linkage and lowercase nucleotide designations designate a nucleotide having a 2'-O-methyl modification.

The composition may consist essentially of one or both of the following nucleic acids:

```
                                        (SEQ ID NO: 30)
5'-GAuGGAucuuGuuGGAAAuusu-3'

(SEQ ID NO: 31)
5'-AUUUCcAACAAGAUCcAUCUsU-3'
``` where s is a phosphorothioate linkage and lowercase nucleotide designations designate a nucleotide having a 2'-O-methyl modification.

In some embodiments the composition consists of one or both of the following nucleic acids:

```
                                        (SEQ ID NO: 30)
5'-GAuGGAucuuGuuGGAAAuusu-3'

(SEQ ID NO: 31)
5'-AUUUCcAACAAGAUCcAUCUsU-3'
``` where s is a phosphorothioate linkage and lowercase nucleotide designations designate a nucleotide having a 2'-O-methyl modification.

Herein provided is a composition that comprises one or both of the nucleic acids:

```
                                        (SEQ ID NO: 32)
5'-GUCUAUGGAAGAAAUAGUUUU-3'

(SEQ ID NO: 33)
5'-UUACUACUACUACUACUACUU-3'
```

In certain embodiments the composition consists essentially of one or both of the nucleic acids:

```
                                        (SEQ ID NO: 32)
5'-GUCUAUGGAAGAAAUAGUUUU-3'

(SEQ ID NO: 33)
5'-UUACUACUACUACUACUACUU-3'
```

In some embodiments the composition consists of one or both of the nucleic acids:

```
                                        (SEQ ID NO: 32)
5'-GUCUAUGGAAGAAAUAGUUUU-3'

(SEQ ID NO: 33)
5'-UUACUACUACUACUACUACUU-3'
```

Further provided herein is a composition that comprises one or both of the nucleic acids:

```
                                        (SEQ ID NO: 34)
5'-GUCUAUGGAAGAAAUAGUUUsU-3'

(SEQ ID NO: 35)
5'-UUACUACUACUACUACUACUsU-3'
``` where s is a phosphorothioate linkage.

The composition may consist essentially of one or both of the nucleic acids:

5'-GUCUAUGGAAGAAAUAGUUUsU-3' (SEQ ID NO: 34)

5'-UUACUACUACUACUACUACUsU-3' (SEQ ID NO: 35)

where s is a phosphorothioate linkage.

In some embodiments the composition consists of one or both of the nucleic acids:

5'-GUCUAUGGAAGAAAUAGUUUsU-3' (SEQ ID NO: 34)

5'-UUACUACUACUACUACUACUsU-3' (SEQ ID NO: 35)

where s is a phosphorothioate linkage.

Also provided herein is a composition that comprises one or both of the nucleic acids:

5'-GucuAuGGAAGAAAuAGuuusU-3' (SEQ ID NO: 36)

5'-UuACuACuACuACuACuACUsU-3' (SEQ ID NO: 37)

where s is a phosphorothioate linkage and lowercase nucleotide designations designate a nucleotide having a 2'-O-methyl modification.

In some embodiments the composition consists essentially of one or both of the nucleic acids:

5'-GucuAuGGAAGAAAuAGuuusU-3' (SEQ ID NO: 36)

5'-UuACuACuACuACuACuACUsU-3' (SEQ ID NO: 37)

where s is a phosphorothioate linkage and lowercase nucleotide designations designate a nucleotide having a 2'-O-methyl modification.

In certain embodiments the composition consists of one or both of the nucleic acids:

5'-GucuAuGGAAGAAAuAGuuusU-3' (SEQ ID NO: 36)

5'-UuACuACuACuACuACuACUsU-3' (SEQ ID NO: 37)

where s is a phosphorothioate linkage and lowercase nucleotide designations designate a nucleotide having a 2'-O-methyl modification.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 5 shows expression of FAS by nontransfected and siRNA-transfected cell lines.

DETAILED DESCRIPTION

Figure 1:
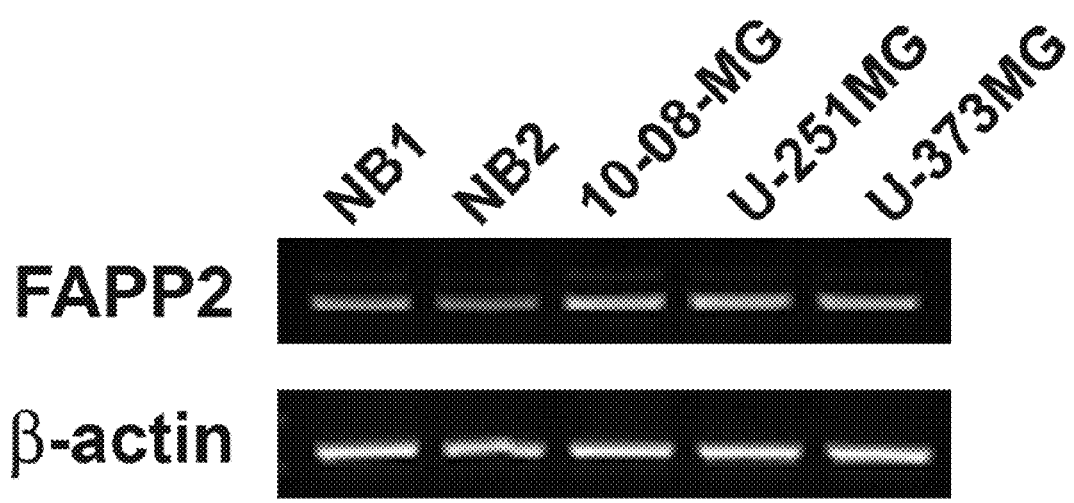
FIG. 1 shows FAPP2 mRNA levels for extracts from two different normal brain (NB) specimens (lanes 1 and 2) and three gliomas (10-08-MG, U-251MG, U-373MG in lanes 3-5, respectively). Beta actin loading controls are shown at the bottom.

Apoptosis is a distinctive form of cell death. It occurs in normal and pathological processes and can be induced by a number of stimuli. Fas (CD95) and Fas ligand (FasL) are members of the TNF death receptor/ligand family. FasL binding to Fas expressing cells can trigger apoptosis of such cells. A significant number of cancer cell types, including colon, breast and brain, coexpress Fas and FasL, yet are resistant to apoptosis induced by this death receptor ligand pair.

Disclosed herein are target genes and anti-tumor methods of targeting the genes. The gene for phosphatidylinositol-4-phosphate adaptor-2 (FAPP2) encodes a cytoplasmic lipid transferase with a plekstrin homology domain that has been implicated in vesicle maturation and transport from trans-Golgi to the plasma membrane. The gene for BTB/POZ AT 10 hook zinc finger protein (PATZ1) encodes a transcription inhibitor. Introduction of ribozymes targeting the FAPP2 gene in colon carcinoma cells can induce apoptosis in the presence of Fas agonistic antibody. Quantitative PCR shows that siRNA specific to FAPP2 and/or PATZ1 but not a randomized siRNA control reduced FAPP2 gene and/or PATZ1 gene expression in tumor cells. Transfection of FAPP2 siRNA and/or PATZ1 siRNA into human tumor cells incubated with FasL can result in reduction of viable cell numbers. Also, FAPP2 and or PATZ1 siRNA transfected glioma and breast tumor cells increasingly underwent apoptosis upon incubation with soluble FasL, but the apoptosis did not necessarily correlate with increased Fas expression. Downregulating the FAPP2 gene and/or the PATZ1 gene in a panel of tumor cells exhibited anti-tumor effects. These data show that FAPP2 and/or PATZ1 can be a target for cancer therapy, and in particular brain tumor therapy. Further disclosed herein is the discovery that downregulation of the overexpression of FAPP2 in brain tumor cells by ribozymes or downregulation of FAPP2 and/or PATZ1 expression by a specific FAPP2 and/or PATZ1 siRNA may be a useful therapeutic technique.

Accordingly, provided herein are therapeutic compositions and methods that can reduce levels of FAPP2 and/or PATZ1 RNA and polypeptide, and induce apoptosis of cancer cells. Such therapeutic compositions and methods are applicable to brain tumors, and gliomas, for example.

FAPP2 and PATZ1 Molecules

A FAPP2 or PATZ1 molecule includes a nucleic acid with significant homology to the defined FAPP2 or PATZ1 nucleic acid sequence elucidated below, and encoded polypeptides. A nucleic acid can be from any suitable source or composition, and can be DNA, cDNA (complementary DNA), gDNA (genomic DNA), RNA, siRNA (short inhibitory RNA), miRNA (micro RNA), RNAi (RNA inhibition or inhibitor), tRNA (transfer RNA) or mRNA (messenger RNA), in some embodiments. A nucleic acid can be in any suitable form (e.g., linear, circular, supercoiled, single-stranded, double-stranded, and the like). A nucleic acid also can comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides also are nucleic acids. Deoxyribonucleotides include deoxyadenosine, deoxycytidine, deoxyguanosine, deoxyinosine, and deoxythymidine. For RNA, the uracil base is uridine. A nucleic acid also may be referred to herein as nucleic acid agent, target nucleic acid, target nucleotide sequence, nucleic acid sequence of interest or nucleic acid region of interest.

A FAPP2 molecule includes any nucleic acid that comprises, encodes, or regulates production of a FAPP2 molecule. A PATZ1 molecule includes any nucleic acid that comprises, encodes, or regulates production of a PATZ1 molecule. A FAPP2 and/or PATZ1 molecule may be in a plasmid, phage, autonomously replicating sequence (ARS), centromere, artificial chromosome, yeast artificial chromosome (e.g., YAC) or other nucleic acid able to replicate or be replicated in a host cell in some embodiments. In certain embodiments a FAPP2 and/or PATZ1 nucleic acid can be from a library or can be obtained from enzymatically digested, sheared or sonicated genomic DNA (e.g., fragmented) from an organism of interest. In general a nucleic acid (e.g. subjected to fragmentation or cleavage) may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various known methods, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme, that can cleave a nucleic acid at one or more specific sites. Specific cleavage agents often will cleave specifically according to a particular nucleotide sequence at a particular site. Nucleic acid may also be cleaved by various other nucleic acids including antisense, nucleic acid analogues, ribozymes, and sRNA such as miRNA, siRNA, which bind to the subject sequence and act as cleavage agents as more fully discussed below.

In certain embodiments a FAPP2 nucleic acid comprises the following nucleotide sequence: (SEQ ID NO: 4)

```
gccgcctgcg accggcagct cgttcgccgc actttggagg cttcggctgc ccctccgacc cacgtagggc ccggacccgg
```

```
gcctccttgt gaacagcgtg ccggcttcgc cccacgggtt
caccggctgg ctgggcttca agcgccgagg ccgccgcagt
gaccccgccc ccgggccgag gatgtgaggc gggccgggcg
tccccacacc gggcccggc gccgggagtg ggcgtctggg
cagcgccagg cgatggccct gctgctggtg ctcctcgcct
cttggggcct ggggcagtga ggggccggc gggcgtgggc
cgagtggccg cgggcgccat ggaggggtg ctgtacaagt
ggaccaacta tctgagcggt tggcagcctc gatggttcct
tctctgtggg ggaatattgt cctattatga ttctcctgaa
gatgcctgga aaggttgcaa agggagcata caaatggcag
tctgtgaaat tcaagttcat tctgtagata atacacgcat
ggacctgata atccctgggg aacagtattt ctacctgaag
gccagaagtg tggctgaaag acagcggtgg ctggtggccc
tgggatcagc caaggcttgc ctgactgaca gtaggaccca
gaaggagaaa gagtttgctg aaaacactga aaacttgaaa
accaaaatgt cagaactaag actctactgt gacctccttg
ttcagcaagt agataaaaca aaagaagtga ccacaactgg
tgtgtccaat tctgaggagg gaattgatgt gggaactttg
ctgaaatcaa cctgtaatac ttttctgaag accttggaag
aatgcatgca gatcgcaaat gcagccttca cctctgagct
gctctaccgc actccaccag gatcacctca gctggccatg
ctcaagtcca gcaagatgaa acatcctatt ataccaattc
ataattcatt ggaaaggcaa atggagttga gcacttgtga
aaatggatct ttaaatatgg aaataaatgg tgaggaagaa
atcctaatga aaaataagaa ttccttatat ttgaaatctg
cagagataga ctgcagcata tcaagtgagg aaaatacaga
```

```
tgataatata acagtccaag gtgaaataag gaaggaagat
ggaatggaaa acctgaaaaa tcatgacaat aacttgactc
agtctggatc agactcaagt tgctctccgg aatgcctctg
ggaggaaggc aaagaagtta tcccaacttt ctttagtacc
atgaacacaa gctttagtga cattgaactt ctggaagaca
gtggcattcc cacagaagca ttcttggcat catgttatgc
tgtggttcca gtattagaca aacttggccc tacagtgttt
gctcctgtta agatggatct tgttggaaat attaagaaag
taaatcagaa gtatataacc aacaaagaag agtttaccac
tctccagaag atagtgctgc acgaagtgga ggcggatgta
gcccaggtta ggaactcagc gactgaagcc ctcttgtggc
tgaagagagg tctcaaattt ttgaagggat ttttgacaga
agtgaaaaat ggggagaagg atatccagac agccctaaat
aatgcatatg gtaaaacatt gcggcaacac catggctggg
tagttcgagg ggttttttgcg gtgtaggaat gtgggtgtag
acggaactcc agaaaccatc atggaccatg aggcaactct
gaggatgaa gccacacact aaggacggta aagcagaaag
aagagctgaa accctgatga taaagaagca gccaattccg
tcctgcactg cccacctcca gatctcattc atgtgaaaca
aagagaaact ttatcttgtt caagtcaaaa aaaaaaaaa
aaaaaaaa
``` and a complement of the foregoing. The foregoing sequence is for a particular isoform of FAPP (i.e., isoform 2), and a nucleic acid pertaining to any other isoform of FAPP2 can be utilized in methods and compositions described herein. Examples of FAPP2 cDNA or mRNA may be found at accession numbers AF380162, BC002838, BC053990, AK023180, and AF308300. A FAPP2 nucleic acid also may include a RNA version of the foregoing nucleotide sequence or complement thereof (e.g., T is substituted with U). Non-limiting examples of an RNA version of the foregoing sequence are: (SEQ ID NO: 3)

```
gccgccugcg accggcagcu cguucgccgc acuuuggagg cuucggcugc cccuccgacc
cacguagggc ccggacccgg gccuccuugu gaacagcgug ccggcuucgc cccacggguu
caccggcugg cugggcuuca agcgccgagg ccgccgcagu gaccccgccc ccgggccgag
gaugugaggc gggccgggcg uccccacacc gggcccgggc gccgggagug ggcgucuggg
cagcgccagg cgauggcccu gcugcuggug cuccucgccu cuuggggccu ggggcaguga
ggggccggc gggcguggc cgaguggccg cgggcgccau ggaggggug cuguacaagu
ggaccaacua ucugagcggu uggcagccuc gaugguuccu ucucuguggg ggaauauugu
ccuauuauga uucuccugaa gaugccugga aagguugcaa agggagcaua caaauggcag
ucugugaaau ucaaguucau ucuguagaua aacacgcau ggaccugaua auccugggg
aacaguauuu cuaccugaag gccagaagug uggcugaaag acagcggugg cugguggccc
ugggaucagc caaggcuugc cugacugaca guaggaccca gaaggagaaa gaguuugcug
aaaacacuga aaacuugaaa accaaaaugu cagaacuaag acucuacugu gaccuccuug
```

-continued

```
uucagcaagu agauaaaaca aaagaaguga ccacaacugg uguguccaau ucugaggagg gaauugaugu gggaacuuug cugaaaucaa ccuguaauac uuuucugaag accuuggaag aaugcaugca gaucgcaaau gcagccuuca ccucugagcu gcucuaccgc acuccaccag gaucaccuca gcuggccaug cucaagucca gcaagaugaa acauccuauu auaccaauuc auaauucauu ggaaaggcaa auggaguuga gcacuguga aaauggaucu uuaaauaugg aaauaaaugg ugaggaagaa auccaauga aaaauaagaa uuccuuauau uugaaaucug cagagauaga cugcagcaua ucaagugagg aaaauacaga ugauaauaua acaguccaag gugaaauaag gaaggaagau ggaauggaaa accugaaaaa ucaugacaau aacuugacuc agucuggauc agacucaagu ugcucuccgg aaugccucug ggaggaaggc aaagaaguua ucccaacuuu cuuuaguacc augaacacaa gcuuuaguga cauugaacuu cuggaagaca guggcauucc cacagaagca uucuuggcau cauguuaugc uguggguucca guauuagaca aacuuggccc uacaguguuu gcuccuguua agauggaucu uguuggaaau auuaagaaag uaaaucagaa guauauaacc aacaaagaag aguuuaccac ucuccagaag auagugcugc acgaagugga ggcggaugua gcccagguua ggaacucagc gacugaagcc cucuugugge ugaagagagg ucucaaauuu uugaagggau uuuugacaga agugaaaaau ggggagaagg auauccagac agcccuaaau aaugcauaug uaaaacauu gcggcaacac cauggcuggg uaguucgagg gguuuuugcg guguaggaau guggguguag acgaacucc agaaaccauc auggaccaug aggcaacucu gaggauggaa gccacacacu aaggacggua aagcagaaag aagagcugaa acccugauga uaaagaagca gccaauuccg uccugcacug cccaccucca gaucucauuc augugaaaca aagagaaacu uuaucuuguu caagucaaaa aaaaaaaaaa aaaaaaaa
``` and a complement of the foregoing.

A FAPP2 polypeptide can be from any suitable source or composition, and can comprise an amino acid sequence described herein. Any peptide fragment of a FAPP2 polypeptide also can be a FAPP2 molecule, and the peptide can be about 5 to about 80 amino acids in length (e.g., about 10, 15, 20, 25, 30, 35, 40, 45, 50, 55, 60, 65, 70 or 75 amino acids in length). A FAPP2 polypeptide comprises the following amino acid sequence in some embodiments: (SEQ ID NO: 10)

```
MEGVLYKWTNYLSGWQPRWFLLCGGILSYYDSPEDAWKGCKGSIQMAVC

EIQVHSVDNTRMDLIIPGEQYFYLKARSVAERQRWLVALGSAKACLTDS

RTQKEKEFAENTENLKTKMSELRLYCDLLVQQVDKTKEVTTTGVSNSEE

GIDVGTLLKSTCNTFLKTLEECMQIANAAFTSELLYRTPPGSPQLAMLK

SSKMKHPIIPIHNSLERQMELSTCENGSLNMEINGEEEILMKNKNSLYL
```

-continued

```
KSAEIDCSISSEENTDDNITVQGEIRKEDGMENLKNHDNNLTQSGSDSS

CSPECLWEEGKEVIPTFFSTMNTSFSDIELLEDSGIPTEAFLASCYAVV

PVLDKLGPTVFAPVKMDLVGNIKKVNQKYITNKEEFTTLQKIVLHEVEA

DVAQVRNSATEALLWLKRGLKFLKGFLTEVKNGEKDIQTALNNAYGKTL

RQHHGWVVRGVFAV
```

The foregoing amino acid sequence is for a particular isoform of FAPP2 (i.e., isoform 2) and other isoforms of FAPP2 can be utilized for compositions and methods described herein. Non-limiting examples of FAPP2 polypeptides can be found under the accession numbers AAK55424.1, AAH02838.1, AAH53990.1, BAB14449.1, and AAG48267.1.

In certain embodiments a PATZ1 nucleic acid comprises PATZ1 variant 2 cDNA sequence transcript variant 2 NM_032050: (SEQ ID NO: 16)

```
  1 gggcctactc tgccgccgcc gccgcccgcc cgctccagcc gccgccgccg ccgccaccgc 61 cctccaggct ccgggacccg gcccgcgcca ccgcccccgt gcgcgcccg ccgccgccgc 121 cttcgccttc gccttttgtt tcctccgctc cggcgccccc gccccggctc gcgctttgca 181 ggggacgcag cgcgcgcccc cagcgggccc gggaaaagcc gcggcgcgcg cgcgcgcctg 241 cgcggcggac ccctccttct cctcccccgcg tgcgcgtgcc cttcttggct gcgcgccggc 301 gccgcctggc gggcgggagg ggaggtggca ggcgcgtttg caggaggggc gcacctcttc
```

-continued

```
 361 gctcgcgcac ccccccggaa ggtagaccgg aaggggagg cgggcgggcg gagaggagag
 421 agtggcgcgc agtccagcga gggcggggt tggctatgtg ggggtggtg caccccgcag
 481 tctagacagt ctgatccggg ctggggcgt gtacactcgg cgcacctgcg agactacaga
 541 gcctcgggcc ggcacgtgtg gggagtgtgg acacgtctgc tgcgccccgc ttctcgctgc
 601 tgagggaag ggaggggcg ggcaggtgca gcggccgggc tagtgggagg gggcggcggc
 661 catggagcgg gtgaacgacg cttcgtgcgg cccgtctggc tgctacacat accaggtgag
 721 cagacacagc acggagatgc tgcacaacct gaaccagcag cgcaaaaacg gcgggcgctt
 781 ctgcgacgtg ctcttgcggg taggcgacga gagcttccca gcgcaccgcg ccgtgctggc
 841 cgcctgcagc gagtactttg agtcggtgtt cagcgcccag ttgggcgacg gcggagctgc
 901 ggacggggt ccggctgatg taggggcgc gacggcagca ccaggcggcg gggccggggg
 961 cagccgggag ctggagatgc acactatcag ctccaaggta tttgggggaca ttctggactt
1021 cgcctacact tcccgcatcg tggtgcgctt ggagagcttt cccgaactca tgacggccgc
1081 caagttcctg ctgatgaggt cggttatcga gatctgccag gaagtcatca acagtccaa
1141 cgtacagatc ctggtacccc ctgcccgcgc cgatataatg ctctttcgcc ccctgggac
1201 ctcggacttg ggcttccctt tggacatgac caacgggca gccttggcag ccaacagcaa
1261 tggcatcgcc ggcagcatgc agccagagga ggaggcagct cgggcggctg gtgcagccat
1321 tgcaggccaa gcctctttgc ctgtgttacc tggggtggac cgcttgccca tggtggctgg
1381 accctatcc ccccaactgc tgacttcccc attccccagt gtggcatcca gtgcccctcc
1441 cctgactggc aagcgaggcc ggggccgccc aaggaaggcc aacctgctgg actcaatgtt
1501 tgggtcccca gggggcctga gggaggcagg catccttcca tgcggtctat gtggtaaggt
1561 gttcactgat gccaaccggc tccggcagca cgaggccag cacgtgtca ccagcctcca
1621 gctgggctac atcgaccttc ctcctccgag gctgggtgag aatgggctac ccatctctga
1681 agaccccgac ggcccccgaa agaggagccg gaccaggaag caggtggctt gtgagatctg
1741 cggcaagatc ttccgtgatg tgtatcatct taaccggcac aagctgtccc actctgggga
1801 gaagccctac tcctgccctg tgtgtgggtt gcggttcaag agaaaagacc gcatgtccta
1861 ccatgtgcgg tcccatgatg ggtccgtggg caagccttac atctgccaga gctgtgggaa
1921 aggcttctcc aggcctgatc acttgaacgg acatatcaag caggtgcaca cttctgagcg
1981 gcctcacaag tgtcagacct gcaatgcttc ttttgccacc cgagaccgtc tgcgctccca
2041 cctggcctgt catgaagaca aggtgccctg ccaggtgtgt gggaagtact tgcgggcagc
2101 atacatggca gaccacctga agaagcacag cgaggggccc agcaacttct gcagtatctg
2161 taaccgagaa ggccagaaat gctcacatca ggatccgatt gagagctctg actcctatgg
2221 tgacctctca gatgccagcg acctgaagac gccagagaag cagagtgcca atggctcttt
2281 ctcctgcgac atggcagtcc ccaaaaacaa aatggagtct gatggggaga agaagtaccc
2341 atgccctgaa tgtgggagct tcttccgctc taagtcctac ttgaacaaac acatccagaa
2401 ggtgcatgtc cgggctctcg ggggcccct gggggacctg gccctgccc ttggctcacc
2461 tttctctcct cagcagaaca tgtctctcct cgagtccttt gggtttcaga ttgttcagtc
2521 ggcatttgcg tcatctttag tagatcctga ggttgaccag cagcccatgg ggcctgaagg
2581 gaaatgaggc agctgctgtg tccccacgga aacaaccatc tggggactgc tgggaaatgc
2641 tgtgaatgcg gagggaagtg atgtttgggt tctgtagctg agagatttt attcatttt
2701 aactgccccc caaccccact ccaactcctt ctccaccacc cattctccca atggtcttta
2761 gaaatagatt ttcatctgat attctgcaga aatatcaatg agacttggta tgggacaggg
```

```
2821 gcagaaaaca ctacataggc ctccaaggca aaaccagtcc cagtttcttt aatgggaaga 2881 agctggaatt cctggtgctc aattcttagt gaccccaatc ctatacccaa atctatgata 2941 ttctgggacc tcagtgattt tggtcccctc ccacttctct agttcgtcat cctcccttcc 3001 catatccttc aaaagaacca cactagggtc tccacctact tatacaatgc ggatgcccaa 3061 ctgtttttaa ggaagccaga agcatcccat ggaccatggg gtgagtgtcc tccaagagcc 3121 ccctgagctc agccctctgc ctggagggct ccagacccttt ctgagccctg cttggaggcg 3181 agcattttca ctgctaggac aagctcagct gttgaggaca cccccaccccc aaatttcagt 3241 tcttacgtga ttttaaccat tcaacatgct gttgggtttt aattctctaa ttattattat 3301 tattgttatt attttttagg accagttgta gtgaattgct actgaaagct atcccaggtg 3361 atacagagct ctttgtaaac cgcagtcaca cattagggtt agtattaaac tttgtttaga
``` or a complement of the foregoing. The foregoing sequence is for a particular isoform of PATZ1. Brain and brain tumors express transcript variant 2, and other isoforms include NM_014323, NM_032052 and NM_03205. A nucleic acid pertaining to any other isoform of PATZ1 can be utilized in methods and compositions described herein. Examples of PATZ1 cDNA or mRNA may be found at accession numbers NM_014323, NM_032052, NM_03205 and BC021091.

A PATZ1 nucleic acid also may include a RNA version of the foregoing nucleotide sequence or complement thereof (e.g., T is substituted with U). Non-limiting examples of an RNA version of the foregoing sequence include the following PATZ1 variant 2 mRNA in which U substitutes for T: (SEQ ID NO: 17)

```
gggccuacucugccgccgccgccgcccgcuccagccgccgccgcc
cgccaccgccuccaggcucccgggacccggcccgcgccaccgccccccgugc
gcgccccgccgccgccgccuucgccuucgccuuugccuuuccuccgcuccgg
cgcccccgcccggcucgcgcuuugcaggggacgcagcgcgcgcccccagc
gggcccgggaaaagccgcggcgcgcgcgcgcgccugcgcggcggacccccuc
cuucuccucccgcgugcgcgugcccuucuuggcugcgcgccggcgccgcc
uggcgggcgggaggggaggugggcaggcgcguuugcaggagggggcgcaccuc
uucgcucgcgcaccccccggaagguagaccgggaaggggaggcgggcggg
cggagaggagagaguggcgcgcaguccagcgagggcgggguuggcuaugu
gggggguggugcacccccgcagucuagacagucugauccgggcuggggggcgu
guacacucgcgcaccugcgagacuacagagccucggccggcacgugugg
ggagugggacacgucugcugcgccccgcuucucgcugcugaggggaaggg
agggggcgggcaggugcagcggccgggcuaggggagggggcggcggccau
ggagcggggugaacgacgcuucgugcggcccgucuggcugcuacacauacca
ggugagcagacacagcacggagaugcugcacaaccugaaccagcagcgcaa
aaacggcgggcgcuucugcgacgugcucuugcgggugaggcgacgagagcuu
cccagcgcaccgcgccgugcuggccgccugcagcgaguacuuugagucggc
guucagcgcccaguuggggcgacggcggagcugcggacggggguccggcuga
uguagggggcgcgacggcagccaccaggcggcggggccgggggcagccggga
gcuggagaugcacacuaucagcuccaagguauuuggggacauucuggacuu
```

```
cgccuacacuucccgcaucguggugcgcuuggagagcuuucccgaacucau
gacggccgccaaguuccugcugaugaggucgguuaucgagaucugccagga
agucaucaaacaguccaacguacagauccugguaccccccugcccgcgccga
uauaaugcucuuucgccccccuggaccucggacuuggggcuucccuuugga
caugaccaacggggcagccuuggcagccaacagcaauggcaucgccggcag
caugcagccagaggaggaggcagcucgggcggcuggugcagccauugcagg
ccaagccucuuugccuguguuaccuggggguggaccgcuugcccaugguggc
uggaccccuauccccccaacugcugacuucccccuucccagucugggcauc
cagugccccucccccugacuggcaagcgaggccgggggccgcccaaggaaggc
caaccugcuggacucaauguuuggguccccaggggggccugaggggaggcagg
cauccuuccaugcggucuaugugguaaggguguuacugaugccaaccggcu
ccggcagcacgaggcccagcacggugucaccagccuccagcuggggcuacau
cgaccuuccuccuccgaggcugggugagaauggggcuacccaucucugaaga
cccccgacggccccccgaaagaggagccggaccaggaagcagguggccuugugu
gaucugcggcaagaucuuccgugaugguguaucaucuuaaccggcacaagcu
gucccacucuggggagaagcccuacuccugcccugugugugggguugcgguu
caagagaaaagaccgcaugucccuaccaugugcggucccaugauggguccgu
gggcaagccuuacaucugccagagcugugggaaaggcuucuccaggccuga
ucacuugaacggacauaucaagcaggugcacacuucugagcggccucacaa
gugucagaccugcaaugcuucuuuugccacccgagaccgucugcgcuccca
ccuggccugucaugaagacaagguguccugccaggugugugggaaguacuu
gcgggcagcauacauggcagaccaccugaagaagcacagcgagggccccag
caacuucugcaguaucuguaaccgagaaggccagaaaugcucacaucagga
uccgauugagagcucugacuccuauggugaccucucagaugccagcgaccu
gaagacgccagagaagcagagugccaaggcucuuucuccgcgacauggc
aguccccaaaaacaaaauggagucugauggggagaagaaguacccaugccc
ugaaugugggagcuucuuccgcucuaaguccuacuugaacaaacacaucca
gaaggugcaugccgggcucucgggggccccuggggggacccugggcccugc
```

```
ccuuggcucaccuuucucuccucagcagaacaugucucuccucgaguccuu ugggugguuucagauuguucagucggcauuugcgucaucuuuaguagauccuga gguugaccagcagcccauggggccugaagggaaaugaggcagcugcugugu ccccacggaaacaaccaucuggggacugcugggaaaugcugugaaugcgga gggaagugauguuugggguucuguagcugagagauuuuuauucauuuuuaac ugccccccaaccccacuccaacuccuucuccaccacccauucucccaaugg ucuuuagaaauagauuuucaucugauauucugcagaaauaucaaugagacu ugguauggacagggcagaaaacacuacauaggccuccaaggcaaaacca gucccaguuucuuuaaugggaagaagcuggaauuccuggugcucaauucuu
```

```
acauuguguaccucaguugugucacaugugagcaagcccagguugaccuug ugaugugaauugaucugaucagacuguauuaaaaauguuaguacauuacuc ua
``` and a complement of the foregoing.

A PATZ1 polypeptide can be from any suitable source or composition, and can comprise an amino acid sequence described herein. Any peptide fragment of a PATZ1 polypeptide also is included as a PATZ1 molecule, and the peptide can be about 5 to about 80 amino acids in length (e.g., about 10, 15, 20, 25, 30, 35, 40, 45, 50, 55, 60, 65, 70 or 75 amino acids in length). In some embodiments a PATZ2 polypeptide comprises the amino acid sequence associated with Peptide Accession Number: NP_114439.1 Transcript variant 2: (SEQ ID NO: 21)

```
  1 MERVNDASCG PSGCYTYQVS RHSTEM-
    LHNL NQQRKNGGRF CFVLLRVGDE SFPAHRAVLA

61 ACSEYFESVF SAQLGDGGAA DGGPADVG-
    GA TAAPGGGAGG SRELEMHTIS SKVFGDILDF

121 AYTSRIVVRL ESFPELMTAA KFLLMRS-
    VIE ICQEVIKQSN VQILVPPARA DIMLFRPPGT

181 SDLGFPLDMT NGAALAANSN GIAGSM-
    QPEE EAARAAGAAI AGQASLPVLP GVDRLPMVAG

241 PLSPQLLTSP FPSVASSAPP LTGKRGR-
    GRP RKANLLDSMF GSPGGLREAG ILPCGLCGKV

301 FTDANRLRQH EAQHGVTSLQ LGYIDLPP-
    PR LGENGLPISE DPDGPRKRSR TRKQVACEIC

361 GKIFRDVYHL NRHKLSHSGE KPY-
    SCPVCGL RFKRKDRMSY HVRSHDGSVG KPYICQSCGK

421 GFSRPDHLNG HIKQVHTSER PHKCQTC-
    NAS FATRDRLRSH LACHEDKVPC QVCGKYLRAA

481 YMADHLKKHS EGPSNFCSIC NREGQKC-
    SHQ DPIESSDSYG DLSDASDLKT PEKQSANGSF

541 SCDMAVPKNK MESDGEKKYP CPECGSF-
    FRS KSYLNKHIQK VHVRALGGPL GDLGPALGSP

601 FSPQQNMSLL ESFGFQIVQS AFASSLVDPE VDQQPMGPEG K
```

```
agugacccaauccuauacccaaaucuaugauauucugggaccucagugau uuuggucccucccacuucucuaguucgucauccucccuucccauauccuu caaaagaaccacacuagggucuccaccuacuuuauacaaugcggaugcccaa cuguuuuuaaggaagccagaagcaucccauggaccauggggugaguguccu ccaagagcccccugagcucagcccucgccuggagggcuccagaccuuucu gagcccugcuuggaggcgagcauuuucacugcuaggacaagcucagcuguu gaggacaccccccacccccaaauuucaguucuuacgugauuuuaaccauucaa caugcuguuggguuuuaauucucaauuauuauuauuguuauuauuuu uuaggaccaguugaugugaauugcuacugaaagcuaucccaggugauacag agcucuuugaaaccgcagucacacauuagggguaguauuaaacuuuguuu agauguaccauaauuaacuuggcuaguugauuguuugaagucuauggaaga aauaguuuuaugcaaaauuuuaaaaaaugccagucuggucagggaaguagg ggguuucaaugcuguuggaaccaggaagguggacagccggcagguaggg
```

The foregoing amino acid sequence is for a particular isoform of PATZ1 (e.g., variant). Brain and brain tumors express transcript variant 2. Other transcript variant peptides include NP_055138.2, NP_114441.1, and NP_114440.1. These and other isoforms of PATZ1 can be utilized for compositions and methods described herein. An additional non-limiting example of a PATZ1 polypeptide can be found under accession number AAH21091.

A FAPP2 or PATZ1 molecule includes, without limitation, a nucleic acid that encodes a polypeptide having, respectively, a FAPP2 or PATZ1 activity. A FAPP2 molecule can be a polypeptide having a FAPP2 activity (e.g., vesicle maturation, transport from trans-Golgi to the plasma membrane). A PATZ1 molecule can be a polypeptide having a PATZ1 activity (e.g. chromatin modeling and transcription regulation, possibly including repression of androgen receptor biosynthesis).

A FAPP2 or PATZ1 nucleic acid can have 80% or more sequence identity to the respective FAPP2 and PATZ1 nucleic acid sequence described herein. A FAPP2 or PATZ1 nucleic acid nucleotide sequence can be 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical respectively to a FAPP2 or PATZ1 nucleotide sequence described herein. A FAPP2 or PATZ1 polypeptide can have 80% or more sequence identity respectively to the FAPP2 or PATZ1 polypeptide sequence described herein. A FAPP2 or PATZ1 polypeptide amino acid sequence can be 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical, respectively, to a FAPP2 or PATZ1 amino acid sequence described herein. The global term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

A calculation of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Another manner for determining whether two nucleic acids are substantially identical is to assess whether a polynucleotide homologous to one nucleic acid will hybridize to the other nucleic acid under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

Fas/FasL Gating Molecules

Fas, also known as CD95 or APO-1, is a transmembrane cell surface receptor that functions in the transduction of apoptotic signals in response to its ligand FasL. Reduced Fas expression is a common mechanism of cells to decrease the sensitivity to FasL-mediated cell death. Similarly, many different cancer types show lost or decreased Fas expression levels. In colorectal carcinoma, Fas expression is progressively reduced in the transformation of normal epithelium to benign neoplasm, adenocarcinomas and metastases. Thus, despite expression of FasL, tumor cells may escape the FasL induced apoptotic signal.

Fas/FasL gating molecules affect apoptosis by impacting the expression and/or action of either or both of Fas and FasL including by sensitizing cells to the apoptotic influence of the Fas FasL ligand pair. For example, a Fas/FasL gating molecule may upregulate or downregulate the expression of Fas and/or FasL. A Fas/FasL gating molecule may enhance or interfere with the migration of Fas to the cell membrane and/or the binding properties of FasL. A Fas/FasL gating molecule may also enable or impair various steps of the Fas/FasL associated apoptotic signal transduction through co-factor binding, substrate competition, inhibition, or other mechanisms. In some embodiments a Fas/FasL interfering gating molecule may be downregulated, resulting in an increase in Fas/FasL mediated apoptosis. In certain embodiments a Fas/FasL enhancing gating molecule may be upregulated, causing a corresponding increase in Fas/FasL mediated apoptosis.

As herein presented, cells that are resistant to apoptosis induction may be rendered susceptible to apoptosis induction by methods described herein, and the cells may then be contacted with an apoptosis inducing agent so as to induce apoptosis in the cell. This method is particularly useful for treating cancer cells such as leukemia cells, as well as other cancer cells such as bladder brain, lung, colon, pancreatic, breast, ovarian, cervical, liver pancreatic, stomach, lymphatic, prostate and the like. Any of a variety of well-known apoptosis inducing agents can be used for this purpose. An embodiment of an apoptosis inducing agent that can be used is one that triggers a "death receptor" type cell surface protein (Baker et al. (1996) Oncogene. 12:1-9), which includes Fas, TNF-alpha receptor, the TRAIL receptor, and the like. In certain embodiments an apoptosis inducing agent triggers the FAS receptor, such as an antibody to the FAS receptor. Other suitable apoptosis inducing agents include adamantyl derivatives (see U.S. Pat. No. 6,127,415 to Pfahl et al.), 2-nitroimidazole derivatives (see U.S. Pat. No. 5,929,014 to Ohyama), benzamidine riboside (see U.S. Pat. No. 5,902,792 to Jayaram), branched apogenic peptide (see U.S. Pat. No. 5,591,717 to Rojko et al.), chemotherapeutic agents such as 5-FU, cisplatin, vincristine, methotrexate, doxirubicin, and the like.

Also provided herein is a method of facilitating the induction of apoptosis in a cell resistant to induction of apoptosis, comprising reducing the level of a protein expressed in the cell which is involved in inhibiting apoptosis induction, and then contacting the cell with an apoptosis inducing agent, such as an agent described above, to induce the cell to undergo apoptosis. The step of reducing the level of the protein involved in apoptosis inhibition sometimes is carried out by reducing the level of the RNA in the cell encoding the protein. In certain embodiments this reduction is accomplished by transducing the cell with an expression vector encoding a ribozyme having a substrate binding sequence that enables the ribozyme to cleave the RNA encoding the protein. In some embodiments the RNA reducing agent is a siNA.

Tumor Cells and Cell Proliferative Diseases

FAPP2 and/or PATZ1 are expressed by brain tumor, breast tumor, and colon tumor cells and also may be implicated in leukemia cells, as well as other cancer cells including bladder, lung, pancreatic, ovarian, cervical, liver pancreatic, stomach, lymphatic, and prostate.

As used herein a tumor cell can exist in vitro or in vivo and can originate from any suitable source organism, such as a mammal (e.g., human or non-human) or other animal (e.g., canine, feline, ungulate (e.g., equine, bovine, ovine, caprine, porcine and the like), reptilian, avian, amphibian, fish), for example. A tumor cell can come from any type of tumor in any portion of the body, for example, sarcomas (e.g., rhabdomyosarcoma, osteosarcoma, for example), lymphomas, blastomas (e.g., hepatocblastoma, retinoblastoma, and neuroblastom, for example), germ cell tumors (e.g., choriocarcinoma, and endodermal sinus tumor, for example), endocrine tumors, and carcinomas (e.g., adrenocortical carcinoma, colorectal carcinoma, hepatocellular carcinoma, for example).

A tumor cell can come from or exist within a brain tumor. A brain tumor can be an abnormal growth of cells within the brain or inside the skull, which can be cancerous or non-cancerous (benign). A brain tumor can be any intracranial tumor having (and/or arising from) abnormal and uncontrolled cell division, often in the brain itself (neurons, glial cells, astrocytes, oligodendrocytes, ependymal cells, lymphatic tissue, blood vessels), in the cranial nerves (myelin-producing Schwann cells), in the brain envelopes (meninges), skull, pituitary and pineal gland, or spread from cancers primarily located in other organs (metastatic tumors). Primary brain tumors sometimes are located infratentorially in the posterior cranial fossa (often in children) and in the anterior two-thirds of the cerebral hemispheres or supratentorial (often in adults), although they can affect any part of the brain. Non-limiting types of brain tumors include glioma (e.g., mixed glioma), glioblastoma (e.g., glioblastoma multiforme), astrocytoma (e.g., anaplastic astrocytoma), oligodendroglioma, medulloblastoma, ependymoma, brain stem tumors, primitive neural ectodermal tumor, and pineal region tumors.

A tumor cell can be from or exist within a breast tumor. A breast tumor can be an abnormal growth of cells within the breast. A breast tumor can be any tumor located or originating in the breast having (and/or arising from) abnormal and uncontrolled cell division, often in the epithelial cells lining the milk ducts. Non-limiting types of breast cancers include ductal carcinoma, which accounts for about 70% of all breast cancer, lobular carcinoma, and Medullary carcinoma which accounts for about 15% of breast cancer. Genetic modifications, including to the BRCA1 and BRCA 2 tumor suppresser genes, may confer susceptibility to breast cancer. The breast cancer can be any form of breast cancer and may be associated with one or more prognostic markers or features, including, but not limited to, estrogen receptor expression, progesterone receptor expression, lymph node metastasis, high proliferative index, detectable p53 expression, advanced tumor stage, and high vascular invasion. Identification of tumor type often is based on a variety of prognostic parameters, including an analysis of specific tumor markers.

A tumor cell can be from or exist within a colon tumor. A colon tumor can be any tumor located in the colon having (and/or arising from) abnormal and uncontrolled cell division. Non-limiting types of colon cancers include adenocarcinoma, which originates in the epithelial cells of the colon, leiomoysarcoma, lymphoma, melanoma, and neuroendocrine tumors. Specific genetic modifications can result in Familial Adenomatous Polyposis (FAP) and Hereditary Non-polyposis Colorectal Cancer (HNPCC). Some colon cancers present as polyps within the colon. For example, individuals with FAP may develop hundreds, or even thousands of intestinal polyps. Other colon cancers, such as HNPCC, do not exhibit polyps.

A tumor cell can be a cultured cell. Suitable culture conditions are known and described in the Examples section herein. Tumor or "neoplastic" cells are particularly suitable for culturing as the same genetic modifications which interfere with apoptosis and allow the tumor cells to survive and proliferate in vivo often render the cells functionally immortal in culture. Therefore, a tumor cell may be almost any cell that has been cultured.

Tumor cells can be isolated from tissues for ex vivo culture in several manners. Cells can be purified from blood, and white blood cells are capable of growth in culture. Mononuclear cells can be released from soft tissues by enzymatic digestion with enzymes such as collagenase, trypsin, or pronase, which break down the extracellular matrix. Alternatively, pieces of tissue can be placed in growth media, and the cells that grow out are available for culture. This latter method is known as explant culture.

Cells cultured directly from a subject are known as primary cells. With the exception of some derived from tumors, most primary cell cultures have limited lifespan. After a certain number of population doublings cells undergo the process of senescence and stop dividing, while generally retaining viability.

Additional examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in Oncol./Hemotol. 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In a particular embodiment, the cell proliferative disorder is pancreatic cancer, including non-endocrine and endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

Cellular proliferation can also cause disease in contexts other than cancer. Additional cell proliferative conditions include, but are not limited to inflammatory conditions, such as inflammation conditions of the skin, including, for example, eczema, discoid lupus erythematosus, lichen planus, lichen sclerosus, mycosis fungoides, photodermatoses, pityriasis rosea, psoriasis. Also included are cell proliferative conditions related to obesity, such as proliferation of adipocytes, for example.

Cell proliferative conditions additionally may include viral diseases, including for example, Acquired Immunodeficiency Syndrome, Adenoviridae Infections, Alphavirus Infections, Arbovirus Infections, Borna Disease, Bunyaviridae Infections, Caliciviridae Infections, Chickenpox, Coronaviridae Infections, Coxsackievirus Infections, Cytomegalovirus Infections, Dengue, DNA Virus Infections, Eethyma, Contagious, Encephalitis, Arbovirus, Epstein-Barr Virus Infections, Erythema Infectiosum, Hantavirus Infections, Hemorrhagic Fevers, Viral, Hepatitis, Viral, Human, Herpes Simplex, Herpes Zoster, Herpes Zoster Oticus, Herpesviridae Infections, Infectious Mononucleosis, Influenza in Birds, Influenza, Human, Lassa Fever, Measles, Molluscum Contagiosum, Mumps, Paramyxoviridae Infections, Phlebotomus Fever, Polyomavirus Infections, Rabies, Respiratory Syncytial Virus Infections, Rift Valley Fever, RNA Virus Infections, Rubella, Slow Virus Diseases, Smallpox, Subacute Sclerosing Panencephalitis, Tumor Virus Infections, Warts, West Nile Fever, Virus Diseases and Yellow Fever. For example, Large T antigen of the SV40 transforming virus acts on UBF, activates it and recruits other viral proteins to Pol I complex, and thereby stimulates cell proliferation to ensure virus propagation. Cell proliferative conditions also include conditions related to angiogenesis (e.g., cancers) and obesity caused by proliferation of adipocytes and other fat cells.

Cell proliferative conditions also include cardiac conditions resulting from cardiac stress, such as hypertension, balloon angioplasty, valvular disease and myocardial infarction. For example, cardiomyocytes are differentiated muscle cells in the heart that constitute the bulk of the ventricle wall, and vascular smooth muscle cells line blood vessels. Although both are muscle cell types, cardiomyocytes and vascular smooth muscle cells vary in their mechanisms of contraction, growth and differentiation. Cardiomyocytes become terminally differentiated shortly after heart formation and thus loose the capacity to divide, whereas vascular smooth muscle cells are continually undergoing modulation from the contractile to proliferative phenotype. Under various pathophysiological stresses such as hypertension, balloon angioplasty, valvular disease and myocardial infarction, for example, the heart and vessels undergo morphologic growth-related alterations that can reduce cardiac function and eventually manifest in heart failure.

Agents

An agent may have one or more activities. An agent may reduce the amount of full length FAPP2 RNA that encodes a FAPP2 polypeptide and/or the amount of full length PATZ1 RNA that encodes a PATZ1 polypeptide. This activity may be performed by various agents including, but not limited to, those that block RNA transcription, those that block transcription though competitive complimentary binding to DNA, those that bind to mRNA and block translation, those that bind to RNA and inhibit processing into mRNA, and those that facilitate digestion of RNA into two or more fragments and those that interfere with tRNA.

An agent may also reduce an amount of FAPP2 and/or PATZ1 polypeptide by interfering with the production, processing and/or stability of FAPP2 and/or PATZ1 RNA or by binding to, cleaving, or otherwise damaging a FAPP2 and/or PATZ1 polypeptide. For example an agent such as an antibody may reduce an amount of active FAPP2 and/or PATZ1 polypeptide by blocking the ability of the polypeptide to interact with a binding partner or a pathway member. Through these and other mechanisms an agent may inhibit cell proliferation and/or induce apoptosis.

Certain types of agents can be useful for conducting methods provided herein. A nucleic acid agent can be from any source or composition, and can be of any suitable type or in any suitable form, such as the types and forms described herein, for example. Nucleic acid agents may be selected for their ability to bind to and cleave or otherwise alter a nucleic acid sequence and/or to bind to the nucleic acid sequence and interfere with transcription, RNA processing, RNA stability or translation, in some embodiments.

A nucleic acid agent can comprise certain elements often selected according to the intended use of the nucleic acid. A nucleic acid agent may be of any length. Any of the following elements can be included in or excluded from a nucleic acid agent. A nucleic acid agent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and a selection element. A nucleic acid agent is provided with one or more of such elements and other elements may be inserted into the nucleic acid before the template is contacted with an in vitro transcription and/or translation system. In some embodiments, a provided nucleic acid agent comprises a promoter, 5'UTR, optional 3'UTR and insertion element(s) by which a target nucleotide sequence is inserted (i.e., cloned) into the template. In certain embodiments, a provided nucleic acid agent comprises a promoter, insertion element(s) and optional 3'UTR, and a 5' UTR/target nucleotide sequence is inserted with an optional 3'UTR. The elements can be arranged in any order suitable for in vitro transcription and/or translation, and in some embodiments a nucleic acid agent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element often is required for DNA synthesis and/or RNA synthesis. A promoter often interacts with a RNA polymerase. A polymerase is an enzyme that catalyses synthesis of nucleic acids using a preexisting nucleic acid agent. When the template is a DNA template, an RNA molecule is transcribed before protein is synthesized. Enzymes having polymerase activity suitable for use in the present methods include any polymerase that is active in the chosen system with the chosen template to synthesize protein. A system can include any suitable polymerase, such as RNA polymerase II, SP6 RNA polymerase, T3 RNA polymerase, T7 RNA polymerase, RNA polymerase III or phage derived RNA polymerase, for example. These and other polymerases are known and nucleic acid sequences with which they interact are known. Such sequences are readily accessed in the art, such as by searching one or more public or private databases, for example, and the sequences are readily adapted to nucleic acid agents described herein.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the transcription and/or translation system being utilized. A 5' UTR sometimes comprises one or more of the following elements known to the artisan: translational enhancer sequence, transcription initiation site, transcription factor binding site, translation regulation site, translation initiation site, translation factor binding site, ribosome binding site, replicon, enhancer element, internal ribosome entry site (IRES), and silencer element.

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the transcription and/or translation system being utilized. A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR sometimes includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

Agents that interact with FAPP2 and/or PATZ1 nucleic acid include, but are not limited to, antisense nucleic acid, ribozymes, siNAs (e.g., including siRNA and miRNA), and antibodies. An antisense nucleic acid agent may be DNA or RNA and is complementary to the sequence of the messenger RNA (mRNA) that codes for a protein. An antisense nucleic acid agent therefore binds to the mRNA, interfering with the expression of the FAPP2 or PATZ1 gene. An antisense nucleic acid agent may also include features that cause stearic blocking such as 2'-0 alkyl, peptide nucleic acid (PNA), locked nucleic acid (IRNA), and Morpholino antisense.

Ribozyme agents are catalytic RNA nucleic acid molecules that bind to the target nucleic acid molecules and cleave them, thereby impairing their ability to function as inhibitors of apoptosis induction. Ribozymes provided herein can be identified and selected by methods described. They may be "hairpin" ribozymes, "hammerhead" ribozymes, in certain embodiments, or any other type of ribozyme known in the art.

A hairpin ribozyme may consist of an approximately 50 to 54 nucleotide RNA molecule. It folds into a 2-dimensional structure that resembles a hairpin, consisting of helical domains, loops and additional helixes that may form between the ribozyme and the substrate. Recognition of the substrate nucleotides by the ribozyme occurs via Watson-Crick base pairing. In some embodiments a ribozyme may be about 5 to about 60 nucleotides in length (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44 45 46 47 48, 49, 50, 51, 52, 53, 54, 55, 56, 57, 58 or 59 nucleotides). A ribozyme sometimes may exceed 60 nucleotides.

Additionally, hammerhead ribozymes including chimeric hammerhead ribozymes (i.e., RNA/DNA hybrids) may be designed to recognize the appropriate sequence for cleavage. Most or all of the binding arms and stem loop may comprise DNA with the catalytic domain between the binding arms and stem loop comprising RNA. Modification of the base composition at the stem loop or catalytic domain regions can increase the catalytic activity of the ribozyme, as assayed by in vitro cleavage. Modification at the 2-position of the sugar of the base, for example, substituting —OCH.sub.3 at this position of an RNA base, can increase the stability of the ribozyme. Other stabilizing substitutions include —OC.sub.1-6Alkyl, -F or other halogens, amino, azido, nitro and phenyl (e.g., U.S. Pat. No. 5,298,612).

The term, "substrate binding sequence" of a ribozyme, as used herein, refers to that portion of the ribozyme that base pairs with a complementary sequence (referred to herein as a "ribozyme sequence tag" or "RST") of a target nucleic acid. Because of the basic similarity in the structure of all hairpin ribozymes, they can be modified to obtain a ribozyme having a specific substrate binding sequences of choice. Once the substrate binding sequence of a specific hairpin ribozyme has been identified, it is relatively easy to engineer an equivalent substrate binding sequence for a hammerhead ribozyme. The general structure of the substrate binding sequence of a hammerhead includes six to nine bases at the 5' end of the ribozyme's binding arm and six to nine bases at the 3' end of the other binding arm. The following approach, for example, may be used to: 1) identify the ribozyme sequence tag (RST) of the RNA target of the specific hairpin ribozyme of interest; 2) specify the first six to nine nucleotides at the 5' end of the hammerhead as complementary to the first six to nine nucleotides at the 3' end of the RST; 3) specify the first 5 nucleotides at the 3' end of the hammerhead as complementary to nucleotides at the 5' end of the RST; and 4) specify nucleotides at positions 6 and 7 from the 3' end of the hammerhead as complementary to the RST, while base 8 from the 3' end is an A.

RNA interference (RNAi) refers to a process of sequence-specific post-transcriptional gene silencing in animals, which can be mediated by short interfering RNAs (siRNAs) and micro RNAs (miRNAs). Without being limited by theory, the process of post-transcriptional gene silencing is thought to be an evolutionarily-conserved cellular defense mechanism used to prevent the expression of foreign genes and is commonly shared by diverse flora and phyla. RNAi molecules are referred to herein as siNA agents.

An siNA agent includes a nucleic acid molecule capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, or epigenetics. For example, siNA molecules herein provided can be used to epigenetically silence genes at both the post-transcriptional level or the pre-transcriptional level. In a non-limiting example, epigenetic regulation of gene expression by siNA molecules of the technology can result from siNA mediated modification of chromatin structure to alter gene expression.

An siNA agent may be a double-stranded polynucleotide molecule comprising self-complementary sense and antisense regions, where the antisense region comprises nucleotide sequence that is complementary to nucleotide sequence in a target nucleic acid molecule or a portion thereof and the sense region having nucleotide sequence corresponding to the target nucleic acid sequence or a portion thereof. An siNA can be assembled from two separate oligonucleotides, where one strand is the sense strand and the other is the antisense strand, where the antisense and sense strands are self-complementary. In some embodiments, each strand comprises nucleotide sequence that is complementary to nucleotide sequence in the other strand; such as where the antisense strand and sense strand form a duplex or double stranded structure, for example where the double stranded region is about 19 base pairs. The antisense strand can comprise a nucleotide sequence that is complementary to nucleotide sequence in a target nucleic acid molecule or a portion thereof and the sense strand comprises nucleotide sequence corresponding to the target nucleic acid sequence or a portion thereof. In some embodiments, an siNA can be assembled from a single oligonucleotide, where the self-complementary sense and antisense regions of the siNA are linked by means of a nucleic acid based or non-nucleic acid-based linker (s). An siNA can be a polynucleotide with a hairpin secondary structure, having self-complementary sense and antisense regions, where the antisense region comprises nucleotide sequence that is complementary to nucleotide sequence in a separate target nucleic acid molecule or a portion thereof and the sense region having nucleotide sequence corresponding to the target nucleic acid sequence or a portion thereof. An siNA can be a circular single-stranded polynucleotide having two or more loop structures and a stem comprising self-complementary sense and antisense regions, where the antisense region comprises nucleotide sequence that is complementary to nucleotide sequence in a target nucleic acid molecule or a portion thereof and the sense region having nucleotide sequence corresponding to the target nucleic acid sequence or a portion thereof, and where the circular polynucleotide can be processed either in vivo or in vitro to generate an active siNA molecule capable of mediating RNAi.

In some embodiments an siNA comprises two strands of RNA. In certain embodiments an siNA comprises two strands of DNA. An siNA may sometimes be a hybrid, comprising one strand of RNA and one strand of DNA. One or both strands may also comprise mixed RNA and DNA. In some embodiments a strand of a siNA (e.g., a strand of a siRNA) may be about 5 to about 60 nucleotides in length (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44 45 46 47 48, 49, 50, 51, 52, 53, 54, 55, 56, 57, 58 or 59 nucleotides). A siNA strand sometimes may exceed 60 nucleotides.

An siNA may also comprise a single-stranded polynucleotide having a nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), where the single stranded polynucleotide can further comprise a terminal phosphate group, such as a 5'-phosphate or 5',3'-diphosphate.

In certain embodiments, an siNA molecule may comprise separate sense and antisense sequences or regions, where the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, an siNA molecule comprises a nucleotide sequence that is complementary to nucleotide sequence of a target gene. In some embodiments, the siNA molecule interacts with nucleotide sequence of a target gene in a manner that causes inhibition of expression of the target gene. An siNA typically is not, and does not function as, a ribozyme.

siNA molecules need not be limited to those molecules containing only RNA or DNA, but further encompass chemically-modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%). In certain embodiments, siNA lack 2'-hydroxy (2'-OH) containing nucleotides. In certain embodiments siNA do not require the presence of nucleotides having a 2'-hydroxy group for mediating RNAi and as such, siNA may include no ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Sometimes siNA molecules can comprise ribonucleotides at about 5,10, 20, 30, 40, or 50% of the nucleotide positions.

siNA agents also may comprise non-standard nucleotides, such as non-naturally occurring nucleotides or chemically synthesized nucleotides or deoxynucleotides. Various modifications to nucleic acid siNA structure can be made to enhance the utility of these molecules. These altered nucleic acids can be referred to as nucleotide analogs. Some non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others. By "modified bases" is meant nucleotide bases other than adenine, guanine, cytosine and uracil at a 1' position, or their equivalents.

In some embodiments an siNA agent may comprise modified siNA molecules, with phosphate backbone modifications. Non-limiting examples of backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions.

"Unmodified nucleoside" as used herein means one of the bases adenine, cytosine, guanine, thymine, or uracil joined to the 1' carbon of beta-D-ribo-furanose. Conversely, "modified nucleoside" means any nucleotide base that contains a modification in the chemical structure of an unmodified nucleotide base, sugar and/or phosphate. In some embodiments the 2'—$NH_2$ or 2'-O—$NH_2$, can be modified or unmodified. Such modified groups are described, for example, in Eckstein et al., U.S. Pat. No. 5,672,695; and Matulic-Adamic et al., U.S. Pat. No. 6,248,878.

A nucleotide analog may also include a "locked" nucleic acid. Certain compositions can be used to essentially "anchor" or "lock" an endogenous nucleic acid into a particular structure. Anchoring sequences serve to prevent disassociation of a nucleic acid siNA complex, and thus not only can prevent copying but will also enable labeling, modification, and/or cloning of the endogeneous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

In addition, chemical substituents, for example cross-linking agents, may be used to add further stability or irreversibility to the reaction. Suitable crosslinking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N- maleimido-1,8-octane and agents such as methyl-3-[(p-azidophenyl) dithio]propioimidate.

In some embodiments FAPP2 and/or PATZ1 may be down-regulated by a targeting polynucleotide agent that interferes with cellular DNA. For example, the targeting polynucleotide may comprise at least one substituent, such as a protein or chemical substituent. This may be done for any number of reasons, including, but not limited to, labeling the targeting probe (and thus the target sequence); increasing the stability of the heteroduplexes including the locks, for example via the use of cross-linking moieties; contributing to gene inactivation, for example by the incorporation of nucleic acid scission moieties. Exogenous targeting polynucleotides that have been modified with appended substituents may be introduced along with recombinase (e.g., RecA) into a target cell to homologously pair with a predetermined endogenous DNA target sequence in the cell. The exogenous targeting polynucleotides may be derivatized, and additional substituents attached, either during or after polynucleotide synthesis, respectively, and are thus localized to a specific endogenous target sequence where they produce an alteration, effect or chemical modification to a local DNA sequence. Attached substituents may be proteins and chemical substituents, and include, but are not limited to: cross-linking agents, both of which are hereby incorporated by reference; nucleic acid cleavage agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, photoactive moieties, nucleic acid modification moieties, labels, purification tags, base-modification agents, agents which normally bind to nucleic acids such as labels, immunoglobulin chains, oligonucleotides and the like. Iron/EDTA chelates often are utilized as chemical substituents where local cleavage of a DNA sequence is desired. Further useful groups prevent hybridization of the complementary single stranded nucleic acids to each other but not to unmodified nucleic acids. 2'-O methyl groups also can be utilized. Additional chemical substituents that can be utilized include labeling moieties, such as fluorescent labels, and purification tags, for example to facilitate purification of target sequences. The substituent group may be directly or indirectly attached to the targeting polynucleotides, for example using linking moieties. Attachment chemistries include: direct linkage, e.g., via an appended reactive amino group and other direct linkage chemistries, although streptavidin/biotin and digoxigenin/antidigoxigenin antibody linkage methods may also be used. Methods for linking chemical substituents are provided in U.S. Pat. Nos. 5,135,720; 5,093,245; and 5,055,556. Other linkage chemistries may be used at the discretion of the practitioner; the particular linking group is not critical, but one may be selected over another for synthetic convenience, to provide solubility, flexibility, hydrophobicity, enhanced activity or to remove secondary structure. Linking groups generally span from about 1 (or zero, when direct linkage is used) to a chain of about 50 atoms, where the atoms can include carbon, nitrogen, oxygen, sulfur, phosphorus and particularly alkyl and heteroalkyl linkers.

An agent as used herein may be in some embodiments an antibody, antibody fragment or a small molecule (e.g., small organic molecule) that specifically interacts with (e.g. binds to) a FAPP2 polypeptide. A variety of antibodies and antibody fragments are available to and can be generated by the artisan for use as a specific binding agent. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. Polyclonal and monoclonal antibodies that bind specific antigens are commercially available, and methods for generating such antibodies are known. In general, polyclonal antibodies are produced by injecting an isolated antigen (e.g., FAPP2 or PATZ1 protein or fragment) into a suitable animal (e.g., a goat or rabbit); collecting blood and/or other tissues from the animal containing antibodies specific for the antigen and purifying the antibody.

Methods for generating monoclonal antibodies, in general, include injecting an animal with an isolated antigen (e.g., often a mouse or a rat); isolating splenocytes from the animal; fusing the splenocytes with myeloma cells to form hybridomas; isolating the hybridomas and selecting hybridomas that produce monoclonal antibodies which specifically bind the antigen.

Methods for generating chimeric and humanized antibodies also are known (see, e.g., U.S. Pat. No. 5,530,101 (Queen, et al.), U.S. Pat. No. 5,707,622 (Fung, et al.) and U.S. Pat. Nos. 5,994,524 and 6,245,894 (Matsushima, et al.)), which generally involve transplanting an antibody variable region from one species (e.g., mouse) into an antibody constant domain of another species (e.g., human). Antigen-binding regions of antibodies (e.g., Fab regions) include a light chain and a heavy chain, and the variable region is composed of regions from the light chain and the heavy chain. Given that the variable region of an antibody is formed from six complementarity-determining regions (CDRs) in the heavy and light chain variable regions, one or more CDRs from one antibody can be substituted (i.e., grafted) with a CDR of another antibody to generate chimeric antibodies. Also, humanized antibodies are generated by introducing amino acid substitutions that render the resulting antibody less immunogenic when administered to humans.

A specific binding reagent sometimes is an antibody fragment, such as a Fab, Fab', F(ab)'2, Dab, Fv or single-chain Fv (ScFv) fragment, and methods for generating antibody fragments are known (see, e.g., U.S. Pat. Nos. 6,099,842 and 5,990,296). In some embodiments, a binding partner in one or more hybrids is a single-chain antibody fragment, which sometimes are constructed by joining a heavy chain variable region with a light chain variable region by a polypeptide linker (e.g., the linker is attached at the C-terminus or N-terminus of each chain) by recombinant molecular biology processes. Such fragments often exhibit specificities and affinities for an antigen similar to the original monoclonal antibodies. Bifunctional antibodies sometimes are constructed by engineering two different binding specificities into a single antibody chain and sometimes are constructed by joining two Fab' regions together, where each Fab' region is from a different antibody (e.g., U.S. Pat. No. 6,342,221). Antibody fragments often comprise engineered regions such as CDR-grafted or humanized fragments. In certain embodiments the binding partner is an intact immunoglobulin, and in other embodiments the binding partner is a Fab monomer or a Fab dimer.

The artisan may optimize a binding agent for a specific use or identify new binding agents using a variety of procedures. For example, binding partners may be identified by lysing cells and analyzing cell lysates by electrophoretic techniques. Alternatively, a two-hybrid assay or three-hybrid assay can be utilized (e.g., U.S. Pat. No. 5,283,317). A two-hybrid system is based on the modular nature of most transcription factors, which consist of separable DNA-binding and activation domains. The assay often utilizes two different DNA constructs. In one construct, a FAPP2 or PATZ1 nucleic acid (sometimes referred to as the "bait") is fused to a gene encoding the DNA binding domain of a known transcription factor (e.g., GAL-4). In another construct, a DNA sequence from a library of DNA sequences that encodes a potential binding partner (sometimes referred to as the "prey") is fused to a gene that encodes an activation domain of the known transcription factor. Sometimes, a FAPP2 and/or PATZ1 nucleic acid is close to the activation domain. If the "bait" and the "prey" molecules interact in vivo, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to identify the potential binding partner.

Small molecule agents can be assayed for interaction with FAPP2 and/or PATZ1 using known methods. Peptide agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; spatially addressable parallel solid phase or solution phase libraries; synthetic library methods requiring deconvolution; "one-bead one-compound" library methods; and synthetic library methods using affinity chromatography selection. Biological library and peptoid library approaches are typically limited to peptide libraries, while the other approaches are applicable to peptide, non-peptide oligomer or small molecule libraries of compounds (Lam, Anticancer Drug Des. 12: 145, (1997)). Examples of methods for synthesizing molecular libraries are known.

An agent can be provided in any suitable form, including, but not limited to, isolated nucleic acid, an expression vector that encodes the agent, a cell having a suitable expression vector, and an isolated protein such as an antibody. The forgoing may be presented as a liquid, gel, powder, paste, or cell culture and may be fresh, frozen, or dried.

An agent can also be provided in a kit. Kits often comprise one or more containers that contain one or more components described herein. A kit comprises one or more components in any number of separate containers, packets, tubes, vials, multiwell plates and the like, or components may be combined in various combinations in such containers. For example, a kit may contain one or more amplification primers for amplifying a nucleotide sequences. In some embodiments a kit may contain amplification nucleic acids, buffers, solvents, and other reagents.

A kit sometimes is utilized in conjunction with a method, and can include instructions for performing one or more methods and/or a description of one or more compositions. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions (e.g., a URL for the World-Wide Web).

Thus, provided herein is a kit that comprises one or more amplification primers for amplifying a nucleotide sequence included for ribozymes and siNAs. In some embodiments, one or more primers in the kit are selected from those described here. In some embodiments, a kit comprises reagents and/or components for performing an amplification reaction (e.g., polymerase, nucleotides, buffer solution, thermocycler, oil for generating an emulsion) and executable instructions. Also included are kits that comprise a nucleic acid agent described herein, and optionally, instructions for using such an agent. A component of a kit may be convenient provided in a convenient form of packaging (e.g., tube, vial, microtiter plate and the like), and instructions may be provided in physical form (e.g., on paper) or in electronic form (e.g., on a computer readable medium (e.g., disk) or via an internet or the World Wide Web).

Nucleic Acid Materials and Manufacture

A nucleic acid agent described herein may be prepared and formulated in a variety of suitable manners known in the art. A nucleic acid agent in some embodiments comprises or consists of DNA, RNA, nucleotide derivatives or combination thereof.

A nucleic acid agent can be generated (e.g., replicated or transcribed) from a polynucleotide that integrates into a genome of a host cell, and methods for stably integrating a subsequence from such a polynucleotide are known. In some embodiments, a nucleic acid agent can be generated from a polynucleotide that does not integrate into a host genome. Such a polynucleotide may be a non-replicating DNA sequence, or a specific replicating sequence genetically engineered to lack the genome-integration ability in certain embodiments. In some embodiments, a polynucleotide is a plasmid. A plasmid may contain any suitable regulatory elements and subsequences known in the art in addition to the subsequence that encodes a nucleic acid agent.

When a nucleic acid agent is expressed from a plasmid in mammalian cells, expression plasmid regulatory elements sometimes are derived from viral regulatory elements. For example, commonly utilized promoters are derived from polyoma, Adenovirus 2, Rous Sarcoma virus, cytomegalovirus, and Simian Virus 40. A plasmid may include an inducible promoter operably linked to the nucleic acid-encoding nucleotide sequence. In addition, a plasmid sometimes is capable of directing nucleic acid expression in a particular cell type by use of a tissue-specific promoter operably linked to the nucleic acid-encoding sequence, examples of which are albumin promoters (liver-specific; Pinkert et al., Genes Dev. 1: 268-277 (1987)), lymphoid-specific promoters (Calame & Eaton, Adv. Immunol. 43: 235-275 (1988)), T-cell receptor promoters (Winoto & Baltimore, EMBO J. 8: 729-733 (1989)), immunoglobulin promoters (Banerji et al., Cell 33: 729-740 (1983) and Queen & Baltimore, Cell 33: 741-748 (1983)), neuron-specific promoters (e.g., the neurofilament promoter; Byrne & Ruddle, Proc. Natl. Acad. Sci. USA 86: 5473-5477 (1989)), pancreas-specific promoters (Edlund et al., Science 230: 912-916 (1985)), and mammary gland-specific promoters (e.g., milk whey promoter; U.S. Pat. No. 4,873,316 and European Application Publication No. 264, 166). Developmentally-regulated promoters also may be utilized, which include, for example, murine hox promoters (Kessel & Gruss, Science 249: 374-379 (1990)) and alpha-fetopolypeptide promoters (Campes & Tilghman, Genes Dev. 3: 537-546 (1989))).

With the availability of automated nucleic acid synthesis apparatus, a nucleic acid agent can be synthesized in vitro. Nucleic acid (e.g., DNA, RNA and derivatives and combinations thereof) can be synthesized directly when the nucleotide sequence is known, or by a combination of PCR cloning and fermentation, for example. When the sequence of a desired polypeptide is known, a suitable coding sequence for a polynucleotide can be inferred. When the polynucleotide is siRNA, it can be readily prepared from corresponding RNA or DNA in vitro. In certain embodiments, siRNA can be prepared in commercially-available nucleotide synthesis apparatus. Alternatively, mRNA in circular form can be prepared. Exonuclease-resistant RNAs such as circular mRNA, chemically blocked mRNA, and mRNA with a 5' cap are preferred, because of their greater half-life in vivo. In certain methods, for example, phage RNA polymerases SP6, T3, or T7 are used to prepare RNA from DNA templates in the presence of the individual ribonucleoside triphosphates. An appropriate phage promoter, such as a T7 origin of replication site is placed in the template DNA immediately upstream of the gene to be transcribed.

In certain embodiments RNA may be chemically blocked at the 5' and/or 3' end to prevent access by RNAse. (This enzyme is an exonuclease and therefore does not cleave RNA in the middle of the chain.) Such chemical blockage can substantially lengthen the half life of the RNA in vivo. Two agents which may be used to modify RNA are available from Clonetech Laboratories, Inc., Palo Alto, Calif.: C2 Amino-Modifier (Catalog #5204-1) and Amino-7-dUTP (Catalog #K1022-1). These materials add reactive groups to the RNA. After introduction of either of these agents onto an RNA molecule of interest, an appropriate reactive substituent can be linked to the RNA according to the manufacturer's instructions. By adding a group with sufficient bulk, access to the chemically modified RNA by RNAse can be prevented.

Nucleic Acid Formulations and Delivery

A nucleic acid may be prepared as a formulation or medicament and may be used as a therapeutic. Any suitable formulation of a nucleic acid can be prepared for administration. Nucleic acid can be isolated and prepared in a composition for use and administration. In some embodiments involving a nucleic acid agent, such as in gene therapies, antisense therapies or siRNA or RNAi therapies, the nucleic acid may integrate with a host genome or not integrate.

A composition can be prepared for any suitable mode of administration, including nasal, topical, oral, pulmonary, parenteral, intrathecal, and intranutrical administration. Naked nucleic acid may be administered to a system, or nucleic acid may be formulated with one or more other molecules. A nucleic acid agent may be naked in the sense that it is free from any delivery vehicle that can act to facilitate entry into the cell, for example, the polynucleotide sequences are free of viral sequences, particularly any viral particles which may carry genetic information. Such nucleic acid is similarly free from, or naked with respect to, any material that promotes transfection, such as liposomal formulations, charged lipids such as Lipofectin™ or precipitating agents such as $CaPO_4$. In some embodiments, a nucleic acid agent can be formulated in any suitable manner known in the art.

Pharmaceutical dosage forms suitable for injection or infusion can include sterile aqueous solutions or dispersions or sterile powders comprising an agent that are adapted for the extemporaneous preparation of sterile injectable or infusible solutions or dispersions, optionally encapsulated in liposomes. In the case of sterile powders for the preparation of sterile injectable solutions, methods of preparation include vacuum drying and the freeze-drying techniques, which yield a powder of the active ingredient plus any additional desired ingredient present in the previously sterile-filtered solutions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Suitable fluidity can be maintained, for example, by the formation of liposomes, by the maintenance of the required particle size in the case of dispersions or by the use of surfactants. Appropriate prevention of the action of microorganisms can be brought about by various antibacterial and antifungal agents, for example, parabens, chlorobutanol, phenol, sorbic acid, thimerosal, and the like. In many cases, an isotonic agent, for example, a sugar, a buffer or salt (e.g., sodium chloride) is included. Prolonged absorption of an injectable compositions can be brought about by use in the compositions of an agent that delays absorption, for example, aluminum monostearate and/or gelatin.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients. Pharmaceutical compositions of a nucleic acid agent provided here include, but are not limited to, solutions, emulsions, and liposome-containing formulations. These compositions may be generated from a variety of components that include, but are not limited to, preformed liquids, self-emulsifying solids and self-emulsifying semisolids.

A solution of a nucleic acid molecule or its salt may be prepared in a buffered solution, sometimes phosphate buffered saline, optionally mixed with a nontoxic surfactant. Dispersions also can be prepared in glycerol, a liquid polyethylene glycol, triacetin, and mixtures thereof and in oils. Under ordinary conditions of storage and use, these preparations sometimes contain a preservative to prevent growth of microorganisms.

Nucleic acid described herein can encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds presented here, pharmaceutically acceptable salts of such prodrugs, and other bioequivalents. In cases where a nucleic acid molecule is sufficiently basic or acidic to form stable nontoxic acid or base salts, administration of the nucleic acid as a salt may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts. Pharmaceutically acceptable salts can be obtained using standard procedures known in the art, for example by reacting a sufficiently basic candidate molecule such as an amine with a suitable acid affording a physiologically acceptable anion. Alkali metal (e.g., sodium, potassium or lithium) or alkaline earth metal (e.g., calcium) salts of carboxylic acids also are made.

Nucleic acid compositions may include one or more pharmaceutically acceptable carriers, excipients, penetration enhancers, and/or adjuncts. Choosing a combination of pharmaceutically acceptable salts, carriers, excipients, penetration enhancers, and/or adjuncts in the composition depends in part upon the mode of administration. Guidelines for choosing the combination of components for a nucleic acid are known, and examples are set forth in U.S. Pat. Nos. 6,455,308 (Freier), 6,455,307 (McKay et al.), 6,451,602 (Popoff et al.), and 6,451,538 (Cowsert).

Nucleic acid may be formulated with a solid carrier, for example a finely divided solid such as talc, clay, microcrystalline cellulose, silica, alumina and the like. Useful liquid carriers include water, alcohols or glycols or water-alcohol/ glycol blends, in which the present candidate molecules can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. A carrier sometimes is isotonic, hypotonic, or weakly hypertonic, and has a relatively low ionic strength, such as provided by a sucrose solution. A preparation may further advantageously comprise a source of a cytokine incorporated into a liposome in the form of a polypeptide or as a polynucleotide.

Pharmaceutical formulations of a nucleic acid described herein may conveniently be presented in unit dosage form, which may be prepared according to conventional techniques well known in the pharmaceutical industry. Such techniques include the step of bringing into association the active ingredients with pharmaceutical carrier(s) and/or excipient(s). In general the formulations can be prepared by uniformly and intimately bringing into association the active ingredients with liquid carriers or finely divided solid carriers or both, and then, if necessary, shaping the product.

In some embodiments, a composition may comprise a plasmid that encodes a nucleic acid described herein. Many of the composition components described above for oligonucleotide compositions, such as carrier, excipient, penetration enhancer, and adjunct components, can be utilized in a composition containing an expression plasmid. Also, a nucleic acid expressed by a plasmid may include one or more of the modifications described above that can be incorporated with or in a nucleic acid after expression by a plasmid. A recombinant plasmid sometimes is designed for nucleic acid expression in microbial cells (e.g., bacteria (e.g., *E. coli.*), yeast (e.g., *S. cerviseae*), or fungi), and often a plasmid is designed for nucleic acid expression in eukaryotic cells (e.g., human cells). Suitable host cells are discussed further in Goeddel, Gene Expression Technology: Methods in Enzymology 185, Academic Press, San Diego, Calif. (1990). A plasmid may be delivered to the system or a portion of the plasmid that contains the nucleic acid encoding nucleotide sequence may be delivered.

Nucleic acid can be translocated into cells via conventional transformation or transfection techniques. As used herein, the terms "transformation" and "transfection" refer to a variety of standard techniques for introducing an nucleic acid into a host cell, which include calcium phosphate or calcium chloride co-precipitation, transduction/infection, DEAE-dextran-mediated transfection, lipofection, electroporation, and iontophoresis. Also, liposome or micelle compositions described herein can be utilized to facilitate nucleic acid administration. A nucleic acid composition may be administered to an organism in a number of manners, including topical administration including ophthalmic, nasal, and mucous membrane delivery, pulmonary administration (e.g., inhalation or insufflation of powders or aerosols, including by nebulizer; intratracheal, intranasal, epidermal and transdermal), oral administration, and parenteral administration (e.g., intravenous, intraarterial, subcutaneous, intraperitoneal injection or infusion, intramuscular injection or infusion; and intracranial (e.g., intrathecal or intraventricular)). The polynucleotide may be introduced into tissues of the body using the injectable carrier alone; liposomal preparations are preferred for methods in which in vitro transfections of cells obtained from the vertebrate are carried out.

A nucleic acid may be modified by chemical linkages, moieties, or conjugates that reduce toxicity, enhance activity, cellular distribution, or cellular uptake of the nucleic acid. Examples of such modifications are set forth in U.S. Pat. Nos. 6,455,308 (Freier), 6,455,307 (McKay et al.), 6,451,602 (Popoff et al.), and 6,451,538 (Cowsert).

Certain aspects of liposomes and other polymatrices, penetration enhancers, surfactants, fatty acids, bile salts, carriers, excipients and other agents are described in greater detail hereafter.

Liposomes and Other Polymatrices

A composition comprising a nucleic acid can be prepared as a solution, emulsion, or polymatrix-containing formulation (e.g., monolayers, micelles, bilayers and vesicles (e.g., liposome, microsphere, micelle)). Examples of such compositions are set forth in U.S. Pat. Nos. 6,455,308 (Freier), 6,455,307 (McKay et al.), 6,451,602 (Popoff et al.), and 6,451,538 (Cowsert), and examples of liposomes also are described in U.S. Pat. No. 5,703,055 (Feigner et al.) and Gregoriadis, Liposome Technology vols. I to III (2nd ed. 1993). A nucleic acid can be formulated in a liposome, micelle or other lipid-containing structure, in some embodiments. Examples of compositions for particular modes of administration are set forth in U.S. Pat. Nos. 6,455,308 (Freier), 6,455,307 (McKay et al.), 6,451,602 (Popoff et al.), 6,451,538 (Cowsert), and 5,703,055 (Feigner, et al.) and in Gregoriadis, Liposome Technology vols. I to III (2nd ed. 1993). Thus, nucleic acid agents here provided may be encapsulated within liposomes or may form complexes thereto, in particular to cationic liposomes. Alternatively, nucleic acid agents may be complexed to lipids, in particular to cationic lipids. Fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof.

As here provided, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Further advantages of liposomes include: liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are lipid surface charge, vesicle size and aqueous volume of liposomes.

Liposomes are useful for transfer and delivery of an agent to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomes often fall into two broad classes. Cationic liposomes are positively charged liposomes that interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes that are pH-sensitive or negatively-charged, entrap nucleic acid rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Such liposomes can include without limitation one or more of monosialoganglioside $G_{M1}$; galactocerebroside sulfate; galactocerebroside sulfate ester; phosphatidylinositol; sphingomyelin; ganglioside $G_{M1}$; and 1,2-sn-dimyristoylphosphatidylcholine.

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Examples of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates. Transfersomes may be described as lipid droplets that are so highly deformable that they are easily able to penetrate through pores smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. Transfersome-mediated delivery of serum albumin has been shown to be as effective as subcutaneous injection of a solution containing serum albumin.

Penetration Enhancers

In one embodiment, various penetration enhancers can be used to effect efficient delivery of nucleic acids. Non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Agents that enhance uptake of oligonucleotides at the cellular level may be added to pharmaceutical compositions. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), can enhance cellular uptake of oligonucleotides. Other agents may be utilized to enhance the penetration of an administered nucleic acid in a composition, including glycols such as ethylene glycol and propylene glycol, pyrrols such as 2-pyrrol, azones, and terpenes such as limonene and menthone.

Surfactant, fatty acid and bile salt penetration enhancers are described in greater detail hereafter.

Surfactants

Surfactants (or "surface-active agents") as here provided are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Surfactants find wide application in formulations such as emulsions (including microemulsions) and liposomes. A common classification and ranking of the properties of different types of surfactants, both natural and synthetic, is by the use of the hydrophile/lipophile balance (HLB). The nature of the hydrophilic group (also known as the "head") provides a useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. Polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. Members of the anionic surfactant class include alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts of this class often are utilized.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Fatty Acids

Various fatty acids and their derivatives that act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654). The use of surfactants in drug products, formulations and in emulsions has been reviewed (Rieger, in Pharmaceutical Dosage Forms, Marcel Dekker, Inc., New York, N.Y., 1988, p. 285).

Bile Salts

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Carriers

Certain compositions that comprising a nucleic acid agent also may incorporate a carrier compound. As used herein, "carrier compound" or "carrier" can refer to a nucleic acid, or analog thereof, that is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. Coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal.

The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration that do not deleteriously react with nucleic acids also can be used to formulate a nucleic acid agent. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acid may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

Certain embodiments provide a composition containing (a) one or more nucleic acid agents and (b) one or more other chemotherapeutic agents that function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds presented here, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of nucleic acid agents. See, generally, The Merck Manual of Diagnosis and Therapy, 15th Ed., Berkow et al., eds., 1987, Rahway, N.J., pages 2499-2506 and 46-49, respectively). Two or more combined compounds may be used together or sequentially.

In another related embodiment, compositions may contain one or more nucleic acid agents, particularly oligonucleotides, targeted to a first nucleic acid and one or more additional nucleic acid agents targeted to a second nucleic acid target. Two or more combined compounds may be used together or sequentially.

Nucleic acids described herein may also be admixed, encapsulated, conjugated or otherwise associated with other molecules, molecule structures or mixtures of compounds, as for example, liposomes, receptor targeted molecules, or other formulations, for assisting in uptake, distribution and/or absorption.

Therapeutic Methods

Provided herein are methods for treating cancer in a subject, where at least one FAPP2 and/or PATZ1 gene product is downregulated in the cancer cells of the subject. The method comprises in some embodiments administering to the subject an effective amount of at least one agent for inhibiting expression of the at least one FAPP2 and/or PATZ1 gene or the activity of the FAPP2 and/or PATZ1 polypeptide such that proliferation of cancer cells is inhibited. In some embodiments other death receptor related molecules are modulated.

In some embodiments, a nucleic acid is utilized to treat a cell proliferative condition. In such treatments, the terms "treating," "treatment" and "therapeutic effect" can refer to reducing or stopping a cell proliferation rate (e.g., slowing or halting tumor growth), reducing the number of proliferating cancer cells (e.g., ablating part or all of a tumor) and alleviating, completely or in part, a cell proliferation condition. An agent described herein can be administered to a subject in need thereof in an amount effective to treat a tumor. The terms "treat" and "treating" as used herein refer to (i) preventing a disease or condition from occurring (e.g. prophylaxis); (ii) inhibiting the disease or condition or arresting its development; (iii) relieving the disease or condition; and/or (iv) ameliorating, alleviating, lessening, and removing symptoms of the disease or condition. The terms also can refer to reducing or stopping a cell proliferation rate (e.g., slowing or halting tumor growth) or reducing the number of proliferating cancer cells (e.g., removing part or all of a tumor).

Any type of symptom associated with a tumor can be treated. The time point of symptom onset in the course of disease correlates in many cases with the nature of the tumor ("benign", i.e. slow-growing/late symptom onset, or malignant, fast growing/early symptom onset). Symptoms of brain tumors, for example, can depend on two factors: tumor size (volume) and tumor location. Large tumors or tumors with extensive perifocal swelling edema often lead to elevated intracranial pressure (intracranial hypertension), which translates clinically into headaches, vomiting (sometimes without nausea), altered state of consciousness (somnolence, coma), dilatation of the pupil on the side of the lesion (anisocoria), papilledema (prominent optic disc at funduscopic examination). However, even small tumors obstructing the passage of cerebrospinal fluid (CSF) may cause early signs of increased intracranial pressure. Increased intracranial pressure may result in herniation (i.e. displacement) of certain parts of the brain, such as the cerebellar tonsils or the temporal uncus, resulting in lethal brainstem compression. In young children, elevated intracranial pressure may cause an increase in the diameter of the skull and bulging of the fontanelles. Depending on the tumor location and the damage it may have caused to surrounding brain structures (e.g., through compression or infiltration), any type of focal neurologic symptoms may occur, such as cognitive and behavioral impairment, personality changes, hemiparesis, hypesthesia, aphasia, ataxia, visual field impairment, facial paralysis, double vision, tremor and the like. A bilateral temporal visual field defect (bitemporal hemianopia) can occur, sometimes due to compression of the optic chiasm. Such a visual defect often is associated with endocrine disfunction (e.g., hypopituitarism or hyperproduction of pituitary hormones and hyperprolactinemia).

An agent may be administered in conjunction with another therapy, in some embodiments. An agent may be administered before, after or concurrently with another therapy. Other therapies include, without limitation, chemotherapies, surgeries, radiotherapies and cell therapies. Non-limiting examples of chemotherapeutic agents include, without limitation, alkylating agents (e.g., cisplatin); antimetabolites (e.g., purine, pyrimidine); plant alkaloids and terpenoids (e.g., taxanes); vinca alkaloids and topoisomerase inhibitors. Surgeries sometimes are tumor removal or cytoreduction, the latter of which is removal of as much tumor as possible to reduce the number of tumor cells available for proliferation. Surgeries include, without limitation, surgery through the nasal cavity (trans-nasal), surgery through the skull base (trans-sphenoidal), and craniotomy (opening of the skull). Radiotherapies include, without limitation, external beam radiotherapy (EBRT or XBRT) or teletherapy, brachytherapy or sealed source radiotherapy, systemic radioisotope therapy or unsealed source radiotherapy, virtual simulation, 3-dimensional conformal radiotherapy, intensity-modulated radiotherapy, particle therapy and radioisotope therapy. Conventional external beam radiotherapy (2DXRT) often is delivered via two-dimensional beams using linear accelerator machines. Stereotactic radiotherapy is a type of external beam radiotherapy that focuses high doses of radiation within the body (e.g., cyberknife, gamma knife and Novalis Tx). Cell therapies include, without limitation, administration alone or in combination of dendritic cells, alloreactive cytotoxic T-lymphocytes, stem cells, and monocytes.

The transport of most bioactive materials from the systemic circulation to the brain is impeded by the mechanical and metabolic barrier known as the blood-brain-barrier. Blood-brain barrier disruption can include, without limitation, osmotic disruption; use of vasoactive substances (e.g., bradykinin); exposure to high intensity focused ultrasound (HIFU); use of endogenous transport systems, including carrier-mediated transporters such as glucose and amino acid carriers, for example; receptor-mediated transcytosis for insulin or transferrin; blocking of active efflux transporters such as p-glycoprotein, for example; intracerebral implantation; convection-enhanced distribution; use of a liposome, and combinations of the foregoing. Desirable blood levels may be maintained by continuous infusion to provide about 0.01-5.0 mg/kg/hr or by intermittent infusions containing about 0.4-15 mg/kg of the active ingredient(s). A desired dose may conveniently be presented in a single dose or as divided doses administered at appropriate intervals, for example, as two, three, four or more sub-doses per day. A sub-dose itself may be further divided, e.g., into a number of discrete loosely spaced administrations. Lipid-soluble molecules often are the only types of molecules able to enter the central nervous system in sufficient amounts, unless there are certain transport systems available. Due to this problem many drugs, which do not cross this barrier, need to be injected directly into the subarachnoid space by lumbar puncture or cysternal puncture (Allison & Stach. Drug Intell. Clin. Pharm. 12; 347:1978).

An agent may in certain embodiments be administered to the nasal cavity of a patient affected with brain cancer. Targeting delivery of an agent to a portion of the nasal epithelium that includes or overlies a nerve structure (i.e., an intranasal nerve structure or InNS) directs delivery of the agent to the central nervous system (CNS), including cranial nerves, the brain, the spinal cord, and cerebrospinal fluid. Dorsonasal nerve structures (DnNSs) such as the sphenopalatine ganglion (SPG) are able to take up pharmaceutical agents delivered to portions of the nasal epithelium that overlie them (or are located in close anatomical proximity thereto) and to serve as a conduit for delivery of such agents to the CNS.

Evidence for a pathway between the olfactory mucosa and the central nervous system came in part from experiments with dyes, injected into the subarachnoid space of the brain passing into the nasal mucous membrane in low concentration (Yoffey. J. Laryng. 43; 166:1949). Other substances were studied, which supported this theory, such as .sup.32 P labelled phosphoric acid (Orosz et al. Acta. Physiol. Acad. Sci. Hung. 11; 75:1957), colloidal gold (.sup.198 Au) (Czerniawska. Acta Otolaryng. 70; 58:1970) and wheat germ agglutinin conjugated to horseradish peroxidase (Kristensen. Acta Neuropath. 19; 145:1971). Additionally, the olfactory region has been the port for certain infections as well as organic solvents, causing meningitis and brain damage, respectively. It has been shown that viruses, such as neurovirulent viruses, have been transported into the brain through the olfactory fibres and into the central nervous system. Other infections have been caused by Human erpetic encephalitis or the bacteria *Hemophilus influenzae*. Parasites such as *Naegleria fowleri* also can be transported across this area into the brain, causing death within 72 hours after infection (Lund et al. J. Neuropath. Exp. Neurol. 47; 497:1988; Kristensson & Olsson. Acta Neuropath. 19; 145:1971).

Formulations suitable for nasal administration using a solid carrier include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient. The agent may be applied alone or in combination with other substances. Particular formulations may include the agent in combination with a pharmaceutically-acceptable carrier and/or components that may facilitate the transfer of the neurologic agent through the nasal mucosa and/or along the olfactory neural pathway to damaged nerve cells of the brain. The agent may be administered intranasally as a powder, spray, gel, ointment, infusion, injection, or drops. Alternatively, the neurologic agent may be administered as eye drops.

A method provided may employ transneuronal anterograde and retrograde transport of the neurologic agent entering through the olfactory system of the brain. Once the agent is dispensed into the nasal cavity, the agent may transport through the nasal mucosa by means of the peripheral olfactory neurons into the olfactory bulb and interconnected areas of the brain such as the hippocampal formation, amygdaloid nuclei, nucleus basalis of Meynert, locus ceruleus, and the brainstem raphe nuclei. The agent alone may facilitate this movement into the brain. Alternatively, the carrier and/or other transfer-promoting factors may assist in the transport of the neurologic agent into and along the olfactory neural pathway. Lipophilic substances in the form of micelles or liposomes (lipid vesicles) may be added to the pharmaceutical composition to enhance absorption of the agent across the olfactory epithelium. To augment such absorption, the agent may be contained within or bound to the surface of the micelles or liposomes. Among those substances that are potential additives are gangliosides such as GM-1, and phospholipids such as phosphatidylserine (PS), which may be combined with the agent either alone or in combination. Liposome additives may include those that provide vesicles bounded by one or more lipid bilayers and are readily soluble in fats, and have an internal cavity filled with a solvent such as water. Suitable liposome additives include those that provide unilamellar, multilamellar or paucilamellar lipid vesicles.

The term "therapeutically effective amount" refers to an amount of an agent used to treat or prevent a disease or disorder, or to treat a symptom of the disease or disorder, in a subject or patient. Nucleic acids generally are used in amounts effective to achieve the intended purpose of reducing the number of targeted cells; detectably eradicating targeted cells; treating, ameliorating, alleviating, lessening, and removing symptoms of a disease or condition; and preventing or lessening the probability of the disease or condition or reoccurrence of the disease or condition. The terms "subject" and "patient" generally refer to an individual who will receive or who has received treatment (e.g., administration of a compound described herein) according to a method described herein. A subject or patient may be any type of organism including animals such as mammals, including but not limited to, primates, cows, sheep, goats, horses, dogs, cats, rabbits, guinea pigs, rats, mice or other bovine, ovine, equine, canine, feline, rodent, or murine species. In some embodiments, the animal is a human.

An effective amount of an agent for administration to a subject can be determined by taking into account factors, such as the size and weight of the subject; the extent of disease penetration; the age, health and sex of the subject; the route of administration; and whether the administration is regional or systemic. For example, an effective amount of an siNA or other FAPP2 and/or PATZ1 inhibitory agent can be based on the approximate weight of a tumor mass to be treated. The approximate weight of a tumor mass can be determined by calculating the approximate volume of the mass, where one cubic centimeter of volume is roughly equivalent to one gram. An effective amount of the FAPP2 and/or PATZ1 inhibitory agent based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of a FAPP2 and/or PATZ1 inhibitory agent can also be based on the approximate or estimated body weight of a subject to be treated. For example, an effective amount of the FAPP2 and/or PATZ1 inhibitory agent that is administered to a subject can range from about 5-3000 micrograms per kilogram of body weight, from about 700-1,000 micrograms per kilogram of body weight, or greater than about 1000 micrograms/kg of body weight. Further examples of doses include about 1 microgram per kilogram to about 500 milligrams per kilogram, about 100 micrograms per kilogram to about 5 milligrams per kilogram, or about 1 microgram per kilogram to about 50 micrograms per kilogram. Dosage may also be from 0.01 ug to 100 g per kg of body weight. A therapeutically effective amount sometimes is determined in part by analyzing samples from a subject, cells maintained in vitro and experimental animals. For example, a dose can be formulated and tested in assays and experimental animals to determine an IC50 value for killing cells. Such information can be used to more accurately determine useful doses.

A useful nucleic acid dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938, 949). Such systems can be used for determining the LD50 (the dose lethal to 50% of the population) and the ED50 (the dose therapeutically effective in 50% of the population) of a nucleic acid. The dose ratio between a toxic and therapeutic effect is the therapeutic index and it can be expressed as the ratio ED50/LD50. The nucleic acid dosage often lies within a range of circulating or tissue concentrations for which the ED50 is associated with little or no toxicity. The dosage may vary within this range depending upon the dosage form employed and the route of administration utilized. For any candidate molecules or nucleic acids used in the methods described herein, the therapeutically effective dose can be estimated initially from cell culture assays.

Another example of effective dose determination for a subject is the ability to directly assay levels of "free" and "bound" nucleic acid in the serum of the test subject. Such assays may utilize antibody mimics and/or "biosensors" generated by molecular imprinting techniques. The nucleic acid is used as a template, or "imprinting molecule", to spatially organize polymerizable monomers prior to their polymerization with catalytic reagents. Subsequent removal of the imprinted molecule leaves a polymer matrix which contains a repeated "negative image" of the nucleic acid and is able to selectively rebind the nucleic acid molecule under biological assay conditions (see, e.g., Ansell, et al., Current Opinion in Biotechnology 7: 89-94 (1996) and in Shea, Trends in Polymer Science 2: 166-173 (1994)). Through the use of isotope-labeling, "free" concentration of nucleic acid can be readily monitored and used in calculations of IC50. Such "imprinted" affinity matrixes can also be designed to include fluorescent groups whose photon-emitting properties measurably change upon local and selective binding of nucleic acid. These changes can be readily assayed in real time using appropriate fiber optic devices, in turn allowing the dose in a test subject to be quickly optimized based on its individual IC50. An example of such a "biosensor" is discussed in Kriz, et al., Analytical Chemistry 67: 2142-2144 (1995).

A FAPP2 and/or PATZ1 inhibitory agent can be administered to achieve peak plasma concentrations of an active compound, in some embodiments, of from about 0.01 to about 100 pM, about 0.5 to about 75 pM, about 1 to 50 pM, or about 2 to about 30 pM. Such concentrations may be achieved, for example, by the intravenous injection of a 0.05 to 5% solution of an active ingredient, optionally in saline. A dose can be administered by any suitable method, including, but not limited to, systemic administration, intratumoral administration, bolus injection, infusion, convection enhanced delivery, blood-brain barrier disruption, intracarotid injection, nasal administration, and combinations thereof (e.g., blood-brain barrier disruption followed by intracarotid injection).

A nucleic acid agent can be administered according to any suitable time course. Methods are known for determining an appropriate dosage regimen for the administration of a FAPP2 and/or PATZ1 inhibitory agent to a given subject. For example, a FAPP2 and/or PATZ1 inhibitory agent can be administered to the subject once (e.g., as a single injection or deposition). Alternatively, a FAPP2 and/or PATZ1 inhibitory agent can be administered once or twice daily to a subject for a period of from about one to about twenty-eight days, and sometimes from about seven to about ten days. In a particular dosage regimen, a FAPP2 and/or PATZ1 inhibitory agent is administered once a day for seven days or more. In certain embodiments that nucleic acid agent may be administered daily, weekly, monthly or yearly, or even once every 2 to 20 years. Where a dosage regimen comprises multiple administrations, the effective amount of an agent administered to the subject can comprise the total amount of agent administered over the entire dosage regimen in some embodiments.

Methods are known in the art for estimating repetition rates for dosing based on measured residence times and concentrations of the drug in bodily fluids or tissues. Following successful treatment, it may be desirable to have a patient undergo maintenance therapy to prevent the recurrence of the disease state, wherein the oligonucleotide is administered in maintenance doses, ranging from 0.01 ug to 100 g per kg of body weight, once or more daily, to once every 20 years. It is understood that appropriate doses of an agent depend upon the potency of the agent with respect to the expression or activity to be modulated. When one or more agents is to be administered to an animal (e.g., a human) to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific candidate molecule employed, the age, body weight, general health, gender, and diet of the subject, the time of administration, the route of administration, the rate of excretion, any drug combination, and the degree of expression or activity to be modulated.

EXAMPLES

The examples set forth below illustrate certain embodiments and do not limit the technology.

Example 1

Cell Lines and Tissues for FAPP2 Analyses

Human glioma cell lines, T98G, U-87MG, U-251MG U-373MG, and 10-08-MG, the metastatic breast cell line, MDA-MB-231-1833 (1833), and DLD1 colon carcinoma cells were cultured in Dulbecco's modified essential medium (DMEM) supplemented with 10% fetal bovine serum (FBS). The cells were chosen for these experiments because they displayed resistance to FasL induced (10 to 150 ng/ml) or Fas agonistic CH11 antibody induced (160 ng/ml) cell death, but gained sensitivity to apoptosis when also placed in the presence of low concentration actinomycin D (actD, 0.02 to 0.1 µg/ml, Alexis), as similarly determined. Freshly-resected human brain specimens, collected under IRB-approved guidelines, were obtained from adult patients undergoing lobectomies for seizures.

Example 2

Ribozymes, siRNA and Primers for FAPP2 Analyses

Templates for the target validation hairpin ribozymes were synthesized by IDT containing the restriction enzyme sites Bam HI and Mlu I. RzFAPP-1: sense 5'-AATAAAGGATC-CATTTCACAAGAAGCCAACCAGAGAAACACACGTT GTGGTATATTACCTGGT ACGCGTAACAAT-3'; antisense 5'-(SEQ ID NO: 38) ATTGTTACGCGTACCAGG-TAATATACCACAACGTGTGTTTCTCTG-GTTGGCTTCTTGTGAAATG GATCCTTTATT-3'; RzFAPP-5: sense 5'-(SEQ ID NO: 39) AATAAAGGATCCT-TAGATTTAGAAACTTACCAGAGAAACACACGTTGT GGTATATTACCTGGTA CGCGTAACAAT-3'; antisense 5'-(SEQ ID NO: 40) ATTGTTACGCGTACCAGGTAATATAC-CACAACGTGTGTTTCTCTGGTAAGTTTCTAAATCTA AG GATCCTTTATT. (SEQ ID NO: 41) The disabled ribozyme (dRz) has a three nucleotide change that is underlined in the following sequence: dRz sense 5'-AATAAAG-GATCCTTAGATTTAGAAACTTACCAGAGCGTCACAC GTTGTGGTATATTACCTGGTA CGCGTAACAAT-3'; antisense 5'-(SEQ ID NO: 42) ATTGTTACGCGTACCAGG-TAATATACCACAACGTGTGACGCTCTGGTAAGTTTC TAAATCTAAG GATCCTTTATT-3". (SEQ ID NO: 43) Templates were annealed in 10 mM Tris buffer (pH 8.0) and 25 mM NaCl by heating to 90° C. for 10 min, then slowly cooling to room temperature. Templates were digested with Bam HI and Mlu I (New England Biolabs) and ligated into the LHPM vector. The siRNAs targeting the FAPP2 gene were designed using the siRNA target finder web site at AMBION-.com. Potential target sites of these siRNAs were subjected to a homology search as previously described. siRNA targeting FAPP2, and as controls, randomized siRNA and siRNA targeting luciferase (luc) were synthesized, purified, and annealed in phosphate buffered saline (PBS, Ambion). siRNA sequences with chemical modifications follow: lower case letters indicate 2'-O-methyl modification at that position. S indicates phosphorothioate linkage. dT indicates deoxythymidine. FAPP2 siRNA: sense 5'-GAuGGAucuuGuuG-GAAAuusu-3' (SEQ ID NO: 30); antisense 5'-AUUUCcAA-cAAGAUCcAUCUsU-3' (SEQ ID NO: 31); randomized control siRNA: sense 5'-GuAGuAGuAGuAGuAGuAAusU-3' (SEQ ID NO: 44; antisense 5'-UuACuACuACuACuAC-uACUsU-3' (SEQ ID NO: 45); luc siRNA: sense 5'-cu-uAcGcuGAGuAcuucGAdTsdT-3' (SEQ ID NO: 46); antisense 5'-UCGAAGuACUcAGCGuAAGdTsdT-3' (SEQ ID NO: 47). The primers for quantitative real time-polymerase chain reaction (qPCR) were synthesized by IDT. The FAPP2 primer set: Fwd 5'ACATCAGGATCCGATTGAGA3' (SEQ ID NO: 48); Rev 5'ATGCACCTTCTGGATGTGTT3' (SEQ ID NO: 49); a GAPDH primer set was obtained from RealTime Primers: Fwd 5' GAGTCAACGGATTTGGTCGT 3' (SEQ ID NO: 50); Rev 5' TTGATTTTGGAGGGATCTCG 3' (SEQ ID NO: 51).

Example 3

Transfection of Ribozyme Plasmids and siRNA for FAPP2 Analyses

For plasmid transfection, DLD1 cells were seeded at 2×10⁶ cells/well in DMEM with 10% FBS in 6-well plates the day prior to transfection. The next day the medium was aspirated and replaced with serum-free DMEM. Lipofectamine/ribozyme plasmid complexes were formed in Opti-MEM (Invitrogen) by adding 10 µg DNA to 4 µl Lipofectamine/well according to the manufacturer protocol. The DNA/lipid complexes were added to the appropriate wells of the 6-well plate and incubated for 6 hr at 37° C. An equal volume of DMEM with 10% FBS was added and the plates were incubated overnight at 37° C. At 48 hr post-transfection, stable cell lines were selected by the addition of 400 µg/ml of G418 (active fraction, Sigma).

For transfection of siRNA, cells were seeded at $2.5 \times 10^4$ cells/well in DMEM with 10% FBS in 24-well plates the day prior to transfection. Oligofectamine/siRNA complexes were formed in serum-free DMEM by adding siRNA (50 nM) to 2 microliters of Oligofectamine (Invitrogen) per well. Complexes were formed at 25° C. for 10 min and then added to the cells in serum-free DMEM (50 microliters per well). Cells were incubated for 18 hr at 37° C. The transfection medium was aspirated and replaced with DMEM with 10% FBS.

Example 4

Quantitative PCR for FAPP2 mRNA for FAPP2 Analyses

RNA was isolated from nontransfected glioma cells, or siRNA-transfected cells at 48 hr post-transfection, using the Absolutely RNA kit (Stratagene) according to the manufacturer protocol. The RNA was reverse transcribed into cDNA using the iScript cDNA kit (BioRad). The FAPP2 mRNA levels were quantitated by the SYBR green method on the iQ5 ribocycler (BioRad) in a 96-well format. Standard curves were obtained for FAPP2 and the internal control glyceraldehyde-3-phosphate dehydrogenase (GAPDH) with template dilutions from 1:50 to 1:6750. Triplicate samples were quantified when run at template dilutions of 1:200 along with minus RT and minus template controls. Amplification was continued for 40 cycles as follows: 94° C.-10s, 55° C.-15s, 65° C.-30s.

Example 5

Flow Cytometry for Fas Expression for FAPP2 Analyses

Cells were harvested with PBS containing 2 mM EDTA, washed and stained with a FITC-conjugated monoclonal antibody specific to Fas (CD95, DX2, BD Pharmingen, San Diego, Calif.). The stained cells were washed, resuspended and analyzed on an LSR II flow cytometer and the mean fluorescence intensities (MFI) of Fas were determined using BD-DIVA software.

Example 6

Cell Death ELISA for FAPP2 Analyses

DLD-1 cells were transfected and treated with CH-11 Fas agonistic antibody as described earlier. Cells in the 24-well plate were trypsinized, pelleted by centrifugation at 2000 g min, washed with PBS and counted on a hemocytometer. Two hundred cells were transferred into each of triplicate wells and lysed according to the manufacturer protocol, then 50 µl were placed into the wells of a cell death ELISA plate. The ELISA, a one-step sandwich immunoassay that uses anti-histone and anti-DNA to detect nucleosomes, was run according to the manufacturer protocol (Roche). The absorbances at 405 nm read from wells containing substrate alone were used as blanks, and the fold differences in absorbances from the experimental versus control wells in which total nucleosome accumulation occurred was determined. Experiments were performed twice.

Example 7

MTT Assays for Viable Cell Number for FAPP2 Analyses

Control or siRNA transfected cells were plated in DMEM with 10% FBS in 24-well plates for 48 hr post-transfection. FasL (SuperFasLigand, Alexis) was added and the cells were incubated at 37° C. for 18 hr. The medium was aspirated and replaced with serum-free DMEM. MTT assay was done as previously described. The data were presented as the percentage reduction in viable cell numbers of the treated cells from those in untreated control wells, calculated as 100-[(A570-A650 sample/A570-A650NT)×100]. Duplicate samples were analyzed and experiments were performed at least twice.

Example 8

Acridine Orange/Ethidium Bromide Staining to Morphologically Identify Apoptotic Cells By Fluorescence Microscopy for FAPP2 Analyses Cells were seeded and transfected as described for the MTT assay. FasL was added 48 hr post-transfection and the cells incubated for 18 hr. Cells were stained with Acridine orange/ethidium bromide (32 µl, Sigma Aldrich) at 100 µg/ml in PBS as previously described. The percentages of apoptotic cells were determined by counting the apoptotic cells from a total of 400 cells (i.e., 200 cells counted in each of two high fields).

Example 9

Statistical Calculations for FAPP2 Analyses

Data were analyzed by 2-way ANOVA using the Prism statistics package (GraphPad Software Inc). Bonferroni post-tests were done to compare treatment groups and to determine statistical significance. The p values are indicated in the figures by asterisk number: $*p<0.05$, $p<0.01$, $*p<0.001$.

Example 10

Validation of the FAPP2 Gene Target by Transfection of Ribozyme Expression Vectors The FAPP2 gene was identified as one of several potential therapeutic targets after phenotypically screening the DLD1 colon carcinoma cell line transfected with a proapoptotic ribozyme library in the presence of Fas agonistic antibody. In brief, ribozymes RzFAPP-1 and RzFAPP-5 were designed, along with a disabled version of RFAPP-5 (dRz) to use as a negative control, and cloned into ribozyme expression vectors. DLD1 cells were transfected with each of the three vectors and stably-transfected cell populations were selected with G418. The transfected cells were exposed to the CH-11 Fas agonistic antibody before assessing for apoptosis by a cell death ELISA that quantitates DNA fragmentation. Both target validation ribozymes seemingly conferred sensitivity to the Fas agonistic antibody relative to those transfected with the control dRz. Quantitation of DNA fragmentation in cells transfected with RFAPP-1 and RFAPP-5 was 1.5+0.21 and 2.1+0.23 fold greater than that of dRz transfected cells. A Bonferroni post-test comparing RzFAPP-1 or -5 with the dRz control group showed statistical significance was obtained with RzFAPP-5 (* p<0.05).

Example 11

FAPP2 mRNA is Slightly Overexpressed in Glial Tumor Cells Compared to Normal Brain Two different normal brain (NB) cell specimens and three different glioma cell lines, 10-08-MG, U-251MG, and U-373MG were analyzed for FAPP2 mRNA expression (FIG. 1). Samples were normalized to the expression of beta-actin by densitometric readings and then the fold change in expression for each glioma was compared to the average reading for normal brain. The fold changes for 10-08-MG, U-251 MG, and U-373MG were 1.5, 1.4, and 1.2, respectively. Thus, the FAPP2 mRNA is slightly overexpressed in glioma cells relative to normal brain.

Example 12

Figure 2:
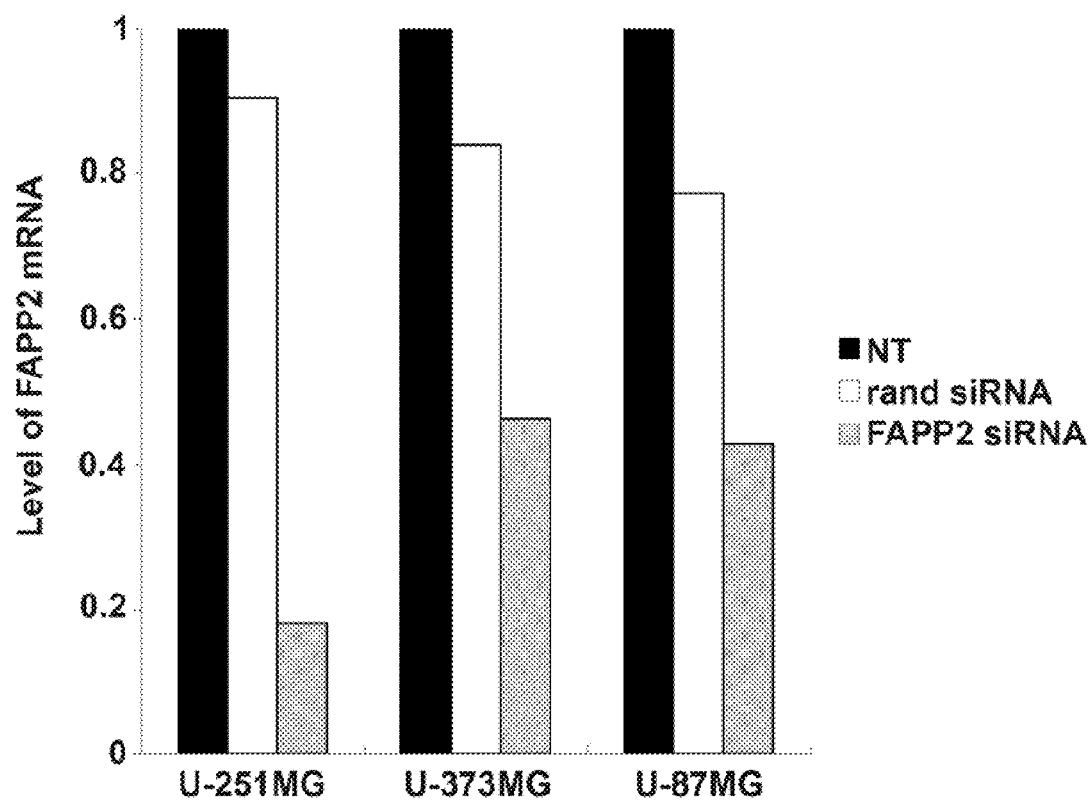
FIG. 2 shows quantitative results of RT-PCR analysis of FAPP2 gene knockdown in glioma cells after transfection with siRNA to FAPP2.

FAPP2 siRNA Decreases FAPP2 Expression and Increases Sensitivity to FasL-Mediated Apoptosis in Several Tumor Types A randomized siRNA and one specific to FAPP2, were designed and then examined for the ability of the transfected siRNA at reducing FAPP2 mRNA expression in tumor cells compared to control nontransfected cells. After transfection of the randomized siRNA into glioma cell lines, U-251 MG, U-373MG and U-87MG, the expression of FAPP2 mRNA was reduced 10 to 20%, whereas if they were transfected with the FAPP2 siRNA the expression of FAPP2 was reduced 50 to 80% (FIG. 2).

Example 13

Selection of FasL-Resistant Tumor Cell Lines for FAPP2 Analyses

As noted previously, the panel of tumor cell lines chosen for this work had to be resistant to FasL-induced apoptosis, or actD induced apoptosis, but exhibit sensitivity when in the presence of both. Five glioma cell lines, T98G, U-87MG, U-251MG, U-373MG, and 10-08-MG, as well as the breast carcinoma metastatic subline 1833 met these criteria. The concentration of FasL for each particular cell line (listed in the legend to FIG. 3) that resulted in >30% killing in the presence of actD was chosen for use in subsequent experiments that tested sensitivity to FasL-induced apoptosis when FAPP2 gene expression was reduced with siRNA.

Example 14

Figure 3:
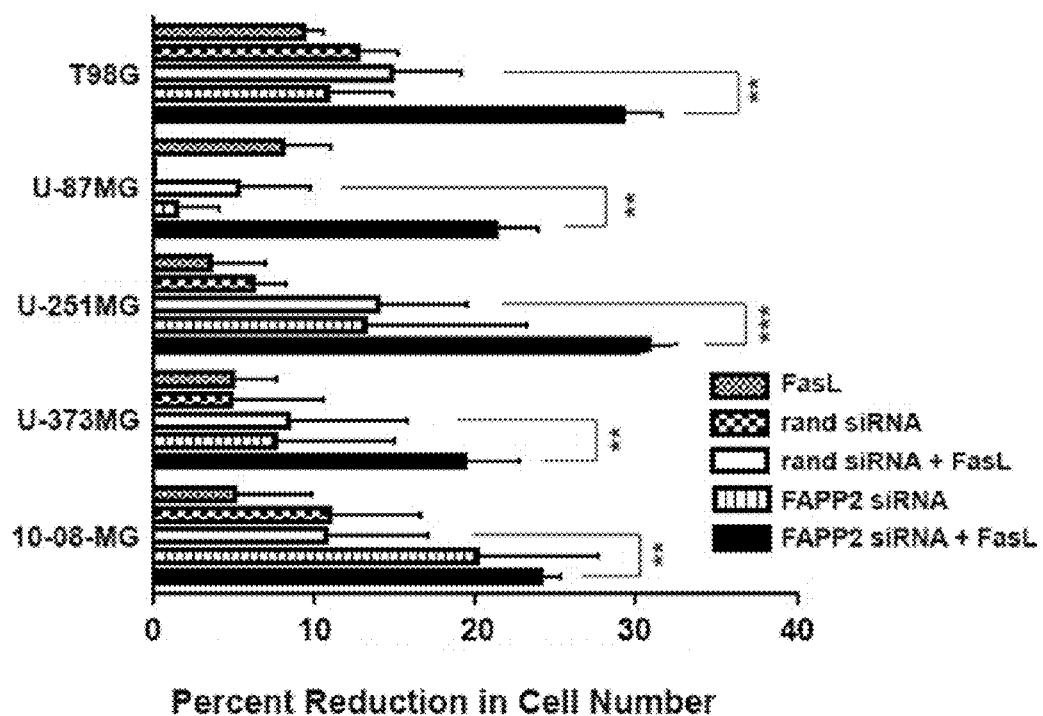
FIG. 3 shows reduction in viable cell number for (A) glioma cells and (B) 1833 breast carcinoma cells following downregulation of FAPP2 in human tumor cell lines exposed to FasL.
Figure 3:
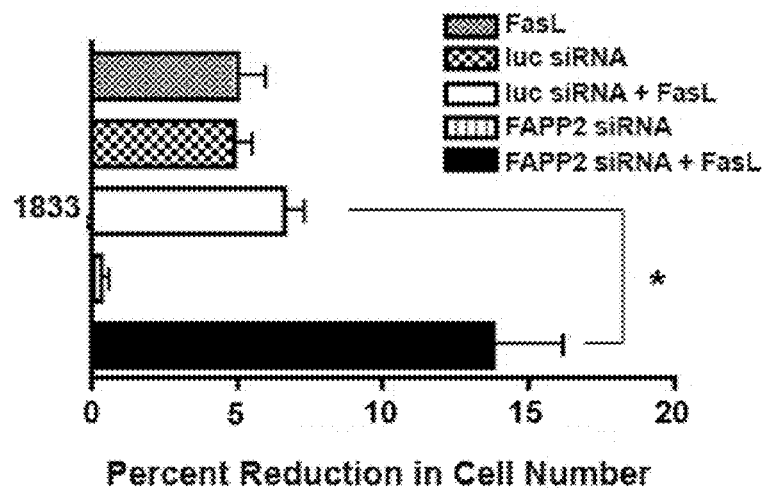
Figure 4:
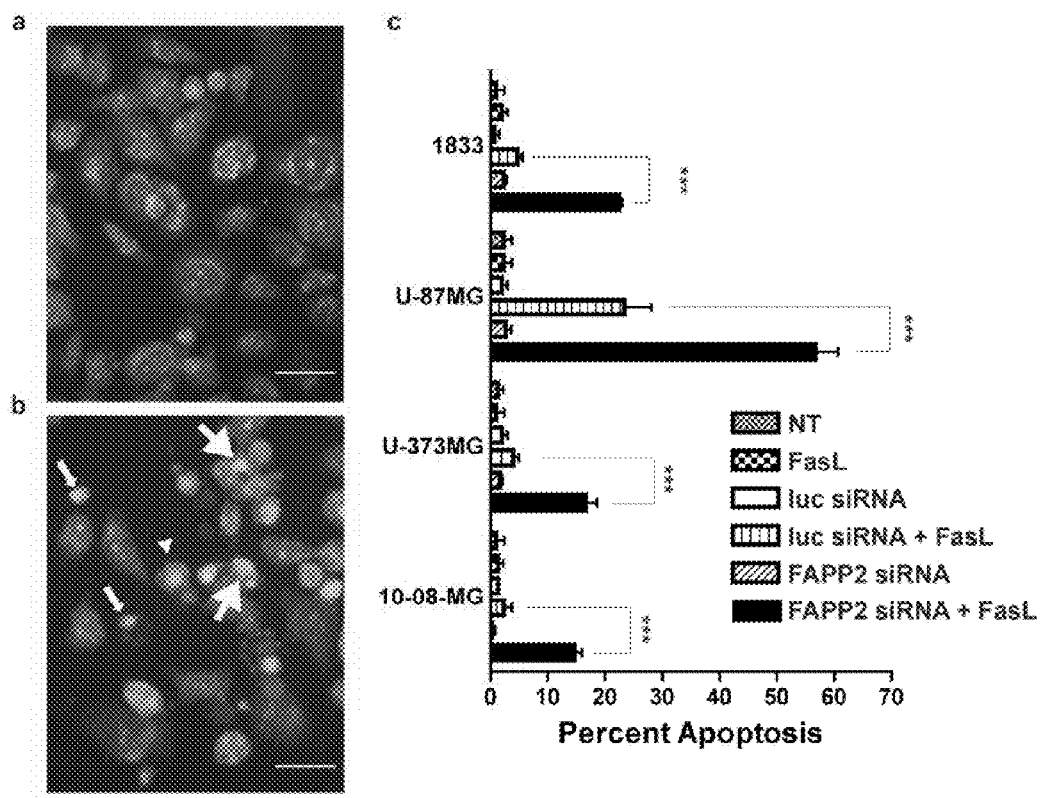
FIG. 4 shows fluorescence microscopy of 1833 breast carcinoma cells after morphologic assay for apoptosis by acridine orange/ethidium bromide staining in (A) 1833 cells transfected with control lucificerase and (B) 1833 cells transfected with FAPP2 siRNA+Fas. Panel (C) represents percentages of apoptotic glioma or breast tumor cells quantified from the morphologic assays.

Downregulation of FAPP2 Sensitizes FasL-Resistant Tumor Cell Lines to Apoptosis MTT assays were performed with the glioma cell lines T98G, U-87MG, U-251 MG, U-373MG, and 10-08-MG (FIG. 3a), and the metastatic breast carcinoma cell line 1833 (FIG. 3b). The cells were either treated with FasL, transfected with randomized or FAPP2 siRNA, or both treated and transfected. Compared to the respective untreated, nontransfected cells, only a 5-10% reduction in viable cell number occurred upon their exposure to FasL, indicating that this treatment had little cytoreductive effect. Likewise, transfection of each cell type with randomized siRNA, with or without FasL treatment, was not effective (<10%) in reducing cell numbers. Downregulation of FAPP2 by siRNA transfection was also largely uneventful for all cells with the exception of 10-08-MG cells where viable cell numbers were reduced approximately 20%. However, when the cells were transfected with FAPP2 siRNA and exposed to FasL, significant reductions in viable cell numbers (18-32%) were observed (*$p<0.05$, $p<0.01$, *$p<0.001$) compared to the most relevant of controls, randomized siRNA transfected tumor cells exposed to FasL (FIG. 3). Three gliomas and the 1833 breast carcinoma cell line were assessed for apoptosis by the acridine orange/ethidium bromide morphologic assay. The control and experimental groups were similar to those used for the MTT assays, except we incorporated the use of a siRNA targeting luciferase, offering validation with a different control that could be used for imaging studies later. Representative fluorescent photomicrographs of 1833 cells transfected with luciferase siRNA and treated with FasL show low basal levels of apoptotic cells (FIG. 4a) that can be compared to the higher numbers of apoptotic cells observed in those transfected with FAPP2 siRNA and treated with FasL (FIG. 4b). The FAPP2 siRNA transfected 1833 cells exposed to FasL demonstrate representative apoptotic cells (bright green) that appear as smaller cells with condensed nuclei (small arrow), membrane blebbing (arrowhead), and fragmented nuclei (large arrow). The percentages of apoptotic cells from the morphologic assay were determined by counting the number of condensed or disintegrated nuclei for 200 cells in each of two different high power fields (FIG. 4c). The apoptotic percentages for all of the cell lines transfected with siRNA to FAPP2 and exposed to FasL were significantly higher (***$p<0.001$) compared to the counterpart control cells transfected with luc siRNA and treated with FasL, with U-87MG glioma cells exhibiting the most dramatic effect.

Example 15

Sensitization to Fas-Induced Apoptosis By FAPP2 Downregulation does not Correlate with Increased Fas Expression Transfection with FAPP2 siRNA resulted in no to small increases in Fas expression compared to luc siRNA transfected or nontransfected tumor cells. For instance, Fas increased 1.1 to 1.2 fold in the U-87MG, U-251 MG, and T98G cell lines, whereas there was no change in the U-373MG and 1833 cell lines (FIG. 5). Transfection with control luc siRNA caused an up- or down-regulation of Fas expression compared to nontransfected cells. These data suggest that the changes in Fas expression following downregulation of FAPP2 by siRNA and incubation with FasL are cell line specific. Furthermore, the inconsistent induction of Fas expression in cells with down-regulated FAPP2 suggests other mechanisms are operational for engendering apoptosis than mere upregulation of Fas itself.

Example 16

Analysis of FAPP2 Results

Screening a retroviral ribozyme library for proapoptotic genes that would activate FasL-induced apoptosis in tumor cells that exhibited resistance to Fas/FasL-induced apoptosis has been previously reported. Herein provided is a role for the FAPP2 gene (also known as PLEKHA8) in conferring sensitivity of glioma cells to apoptotic stimuli. The protein product of the FAPP2 gene contains a plekstrin homology (PH) domain; it binds phosphatidylinositol-4-phosphate (PtdIns(4) P) and localizes the protein to the Golgi complex. The PH domain also facilitates interaction of FAPP2 with ADP-ribosylation factor, which along with PtdIns(4)P binding, allows FAPP2 to control the transport of cargo from the Golgi to the cell surface. The FAPP2 protein additionally contains a domain found in glycolipid transport proteins and functions in the synthesis of sphingolipids. FAPP2 reversibly transports glucosylceramide from the ER to the Golgi and facilitates the production of ceramides in the cell. Although FAPP2 has not previously been functionally associated with FasL-induced apoptosis or any other part of the known apoptotic pathways, ceramides are sensory signaling molecules known to be involved in apoptotic pathways.

It was observed that the FAPP2 gene, when down-regulated, promotes death receptor induced apoptosis in tumor cells. Further described is the in vitro efficacy of a FAPP2 targeted siRNA when transfected into tumor cells in exhibiting anti-tumor effects including the activation of apoptosis by FasL or by Fas agonistic antibodies, or anti-proliferative responses. Since downregulation of FAPP2 sensitizes cells to Fas-induced apoptosis even in the absence of increased Fas expression, it is likely that FAPP2 is contributing to an as yet undescribed, compensatory pathway that results in apoptotic induction in the presence of FasL. Deciphering the pathway mechanism of the FAPP2 gene in conferring Fas resistance to tumor cells should increase our understanding of tumor cell resistance to death receptor triggered apoptosis. This may be especially relevant for breast cancer as the FAPP2 gene has been tentatively identified serologically as a potential breast cancer antigen.

In conclusion, the gene for phosphatidylinositol-4-phosphate adaptor-2 (FAPP2) encodes a cytoplasmic lipid transferase with a plekstrin homology domain that has been implicated in vesicle maturation and transport from trans-Golgi to the plasma membrane. The introduction of ribozymes targeting the FAPP2 gene in colon carcinoma cells induced their apoptosis in the presence of Fas agonistic antibody. Furthermore, quantitative PCR showed that a siRNA specific to FAPP2, but not a randomized siRNA control, reduced FAPP2 gene expression in tumor cells. Transfection of FAPP2 siRNA into human tumor cells then incubated with FasL resulted in reduction of viable cell numbers. Also, FAPP2 siRNA transfected glioma and breast tumor cells showed significant increases in apoptosis upon incubation with soluble FasL, but the apoptosis did not necessarily correlate with increased Fas expression. These data demonstrate a previously unknown role for FAPP2 in conferring resistance to apoptosis and indicate that FAPP2 may be a target for cancer therapy.

Citations for Examples 1-16

1. J. Yanagisawa, M. Takahashi, H. Kanki, H. Yano-Yanagisawa, T. Tazunoki, E. Sawa, T. Nishitoba, M. Kamishohara, E. Kobayashi, S. Kataoka, and T. Sato, The molecular interaction of Fas and FAP-1. A tripeptide blocker of human Fas interaction with FAP-1 promotes Fas-induced apoptosis. J Biol Chem 272 (1997) 8539-45.
2. B. C. Barnhart, P. Legembre, E. Pietras, C. Bubici, G. Franzoso, and M. E. Peter, CD95 ligand induces motility and invasiveness of apoptosis-resistant tumor cells. Embo J 23 (2004) 3175-85.
3. R. Tritz, C. Habita, J. M. Robbins, G. G. Gomez, and C. A. Kruse, Catalytic nucleic acid enzymes for the study and development of therapies in the central nervous system: Review Article. Gene Ther Mol Biol 9A (2005) 89-106.
4. S. Fulda, E. Meyer, and K. M. Debatin, Metabolic inhibitors sensitize for CD95 (APO-1./Fas)-induced apoptosis by down-regulating Fas-associated death domain-like interleukin 1-converting enzyme inhibitory protein expression. Cancer Res 60 (2000) 3947-56.
5. A. Zisman, C. P. Ng, A. J. Pantuck, B. Bonavida, and A. S. Belldegrun, Actinomycin D and gemcitabine synergistically sensitize androgen-independent prostate cancer cells to Apo2L/TRAIL-mediated apoptosis. J Immunother 24 (2001) 459-71.
6. Y. Kang, P. M. Siegel, W. Shu, M. Drobnjak, S. M. Kakonen, C. Cordon-Cardo, T. A. Guise, and J. Massague, A multigenic program mediating breast cancer metastasis to bone. Cancer Cell 3 (2003) 537-49.
7. R. Tritz, B. M. Mueller, M. J. Hickey, A. H. Lin, G. G. Gomez, P. Hadwiger, D. Sah, L. Muldoon, E. A. Neuwelt, and C. A. Kruse, siRNA Down-regulation of the PATZ1 Gene in Human Glioma Cells Increases Their Sensitivity to Apoptotic Stimuli. Cancer Ther 6 (2008) 867-878.
8. Q. X. Li, J. M. Robbins, P. J. Welch, F. Wong-Staal, and J. R. Barber, A novel functional genomics approach identifies mTERT as a suppressor of fibroblast transformation. Nucleic Acids Res 28 (2000) 2605-12.
9. T. Yamaji, K. Kumagai, N. Tomishige, and K. Hanada, Two sphingolipid transfer proteins, CERT and FAPP2: Their roles in sphingolipid metabolism. IUBMB Life (2008).
10. A. Godi, A. Di Campli, A. Konstantakopoulos, G. Di Tullio, D. R. Alessi, G. S. Kular, T. Daniele, P. Marra, J. M. Lucocq, and M. A. De Matteis, FAPPs control Golgi-to-cell-surface membrane traffic by binding to ARF and PtdIns(4)P. Nat Cell Biol 6 (2004) 393-404.
11. S. Zollman, D. Godt, G. G. Prive, J. L. Couderc, and F. A. Laski, The BTB domain, found primarily in zinc finger proteins, defines an evolutionarily conserved family that includes several developmentally regulated genes in *Drosophila*. Proc Natl Acad Sci USA 91 (1994) 10717-21.
12. V. J. Bardwell, and R. Treisman, The POZ domain: a conserved protein-protein interaction motif. Genes Dev 8 (1994) 1664-77.
13. O. V. Vieira, P. Verkade, A. Manninen, and K. Simons, FAPP2 is involved in the transport of apical cargo in polarized MDCK cells. J Cell Biol 170 (2005) 521-6.
14. T. Mastrangelo, P. Modena, S. Tornielli, F. Bullrich, M. A. Testi, A. Mezzelani, P. Radice, A. Azzarelli, S. Pilotti, C. M. Croce, M. A. Pierotti, and G. Sozzi, A novel zinc finger gene is fused to EWS in small round cell tumor. Oncogene 19 (2000) 3799-804.
15. T. P. Levine, A lipid transfer protein that transfers lipid. J Cell Biol 179 (2007) 11-3.
16. D. Halter, S, Neumann, S. M. van Dijk, J. Wolthoorn, A. M. de Maziere, O. V. Vieira, P. Mattjus, J. Klumperman, G. van Meer, and H. Sprong, Pre- and post-Golgi translocation of glucosylceramide in glycosphingolipid synthesis. J Cell Biol 179 (2007) 101-15.
17. Q. Wang, J. Jolly, J. Surmeier, B. Mullah, M. Lidow, C. Bergson, and J. Robishaw, Differential dependence of the D1 and D5 dopamine receptors on the G protein gamma 7 subunit for activation of adenylylcyclase. J Biol Chem 276 (2001) 39386-39393.
18, R. J. Bleicher, and M. C. Cabot, Glucosylceramide synthase and apoptosis. Biochim Biophys Acta 1585 (2002) 172-8.
19. M. J. Knight, C. D. Riffkin, A. M. Muscat, D. M. Ashley, and C. J. Hawkins, Analysis of FasL and TRAIL induced apoptosis pathways in glioma cells. Oncogene 20 (2001) 5789-98.
20. M. J. Scanlan, I. Gout, C. M. Gordon, B. Williamson, E. Stockert, A. O. Gure, D. Jager, Y. T. Chen, A. Mackay, M. J. O'Hare, and L. J. Old, Humoral immunity to human breast cancer: antigen definition and quantitative analysis of mRNA expression. Cancer Immun 1 (2001) 4.
21. S. Xia, Y. Li, E. M. Rosen, and J. Laterra, Ribotoxic stress sensitizes glioblastoma cells to death receptor induced apoptosis: requirements for c-Jun NH2-terminal kinase and Bim. Mol Cancer Res 5 (2007) 783-92.

Example 17

Cell Lines and Tissues for PATZ1 Analyses

Human glioma cell lines 10-08-MG, U-251MG, U-373MG, U-87MG, and T98G were cultured in Dulbecco's modified essential medium (DMEM) supplemented with 10% fetal bovine serum (FBS).

Example 18 siRNA and Primers for PATZ1 Analyses

The siRNAs targeting the PATZ1 gene were designed using the siRNA target finder web site at AMBION.com. Potential target sites of these siRNAs were subjected to a homology search with megablast algorithm against the genome plus transcript database at NCBI to identify siRNAs that avoid potential human off target transcripts. siRNA targeting PATZ1 and—as controls—randomized siRNA and siRNA targeting luciferase (luc) were synthesized on an AB13900 DNA synthesizer using standard procedures, purified by AEX HPLC, and annealed in phosphate buffered saline (PBS, Ambion). siRNA sequences with chemical modifications follow: Lower case letters indicate 2'-O-methyl modification at that position. S indicates phosphorothioate linkage. dT indicates deoxythymidine. PATZ1 siRNA: sense 5'-GUCUAUG-GAAGAAAUAGUUUU-3'(SEQ ID NO: 52); antisense 5'-AACUAUUUCUUCCAUAGACUU-3' (SEQ ID NO:53); randomized control siRNA: sense 5'-CUAUAUC-CUAGUAUGAGUCAAUU-3' (SEQ ID NO: 54); antisense 5'-GACUCAUACUAGGAUAUAGUU-3' (SEQ ID NO: 55); luc siRNA: sense 5'-cuuAcGcuGAGuAcuucGAdTsdT-3' (SEQ ID NO: 46); antisense 5'-UCGAAGuACU-cAGCGuAAGdTsdT-3' (SEQ ID NO: 47). Primers for quantitative real time-polymerase chain reaction (qPCR) were synthesized by IDT (Coralville, Iowa). PATZ1 primer set: Fwd 5'ACATCAGGATCCGATTGAGA3' (SEQ ID NO: 48); Rev 5'ATGCACCTTCTGGATGTGTT3'(SEQ ID NO: 49); a GAPDH primer set was obtained from RealTime Primers: Fwd 5' GAGTCAACGGATTTGGTCGT 3' (SEQ ID NO: 50); Rev 5' TTGATTTTGGAGGGATCTCG 3' (SEQ ID NO: 51).

Example 19

Transfection of siRNA for PATZ1 Analyses

Glioma cells were seeded at $2.5 \times 10^4$ cells/well in DMEM with 10% FBS in 24-well plates the day prior to transfection. Oligofectamine/siRNA complexes were formed in serum free DMEM by adding siRNA (50 nM final concentration) to 2 μl of Oligofectamine (Invitrogen, Carlsbad, Calif.) per well. Complexes were allowed to form at 25° C. for 10 min and added to wells (50 μl per well) containing attached glioma cells in the 24-well plates and incubated for 16-18 hr at 37° C. in 0.5 ml of DMEM. The transfection medium was then aspirated from the wells and replaced with 0.5 ml DMEM with 10')/0 FBS.

Example 20

Quantitative PCR for PATZ1 Analyses

RNA was isolated from nontransfected glioma cells or siRNA transfected cells at 48 hr post-transfection using the Absolutely RNA kit (Stratagene, San Diego, Calif.) according to the manufacturer's protocol. The RNA was reverse transcribed into cDNA using the iScript cDNA kit (Bio Rad, Hercules, Calif.). The PATZ1 mRNA level was quantitated by the SYBR green method on the iQ5 ribocycler (Bio Rad) in a 96-well format. Briefly, standard curves were obtained for PATZ1 and the internal control glyceraldehyde-3-phosphate dehydrogenase (GAPDH) with template dilutions from 1:50 to 1:6750. Samples to be quantitated were run at a template dilution of 1:200 along with minus RT and minus template controls. Amplification was continued for 40 cycles as follows: 94° C.-10s, 55° C.-15s, 65° C.-30s.

Example 21

MTT Assay for PATZ1 Analyses

Nontransfected glioma cells or siRNA transfected cells in DMEM with 10% FBS were incubated with FasL (SuperFas-Ligand, Alexis, Lausen, Switzerland) or TRAIL (Cell Sciences Inc., Sharon, Mass.) starting 48 hr post-transfection. Initial experiments were performed with the addition of actD (0.02 μg/ml to 0.1 μg/ml, Alexis) to determine cell sensitivity to Fas/FasL- or TRAIL-induced apoptosis. Cells were incubated at 37° C. for 18 hr, then medium was aspirated and replaced with serum free DMEM. The yellow tetrazole, 3-(4, 5-dimethylthiazole-2-yl)-2,5-diphenyltetrazolium bromide (MTT, EMD Chemicals, Inc., Gibbstown, N.J.) was added at a final concentration of 1 mg/ml and incubated at 37° C. for 30 min. Blue formazon, solubilized by adding 100% DMSO to the wells, produced by viable cells was quantified from spectrophotometer readings at 570 nm after subtracting the background reading at 650 nm. The data were presented as the percentage reduction in viable cell numbers of the treated cells from those in untreated control wells, calculated as 100-[(A570-A650 sample/A570-A650NT)×100].

Example 22

Acridine Orange Staining for PATZ1 Analyses

Cells were seeded and transfected as described for the MTT assay. FasL was added 48 hr post-transfection and the cells incubated for 18 hr. Acridine orange/ethidium bromide (32 μl, Sigma Aldrich, St. Louis, Mo.) at 100 μg/ml in PBS were added to cells for 15 min at 37° C. The plates were then centrifuged for 5 min. Staining medium was aspirated and replaced with 0.5 ml of PBS. Cells were photographed on an Olympus CKX41 fluorescent microscope. Two high field magnifications were photographed for each treatment. The percentages of apoptotic cells were determined by counting the apoptotic cells from a total of 400 cells (i.e., 200 cells counted in each of two high fields).

Example 23

PATZ1 Gene Expression Microarray Analysis

The gene expression profiles of siRNA transfected and nontransfected glioma cells were analyzed using the GEArray Q Series Human Apoptosis Gene Array (SuperArray Bio-science Corp., Frederick, Md.). The array contains 96 apoptosis-related gene specific cDNA fragments and 4 housekeeping genes for normalization of the data. Total RNA (5 g) was reverse transcribed and the resulting cDNA probes amplified (GeneAmp PCR System 9700, Applied Biosystems, Foster City, Calif.) according to the manufacturer. Prior to hybridization, biotin-labeling efficiency of the probes was determined by manufacturer instructions. Hybridization of the probes to the membranes was detected by chemiluminescence and the hybridization signals captured on X-ray film. Images were scanned and converted to grayscale TIF files. The hybridization signals were converted into numerical data using the ScanAlyze software program (http://rana.lbl.gov/EisenSoftware.htm). The raw intensity signals were corrected for background by subtracting the minimum value of the data set and normalized to the housekeeping gene RPL13A (ribosomal protein L13A). Gene expression changes between the treated or untreated gliomas were determined with the GEArray Analyzer software program.

Example 24

Selection of FasL-Resistant Glioma Cell Lines for PATZ1 Analyses

Human glioma cells were required to meet three defined criteria in order to be selected for inclusion on the panel to be screened for activation of Fas/FasL-induced apoptosis with the PATZ1 siRNA: i) resistance to FasL-induced apoptosis, ii) increased FasL induced apoptosis in the presence of low concentrations actD, and iii) expression of PATZ1 mRNA.

Figure 12:
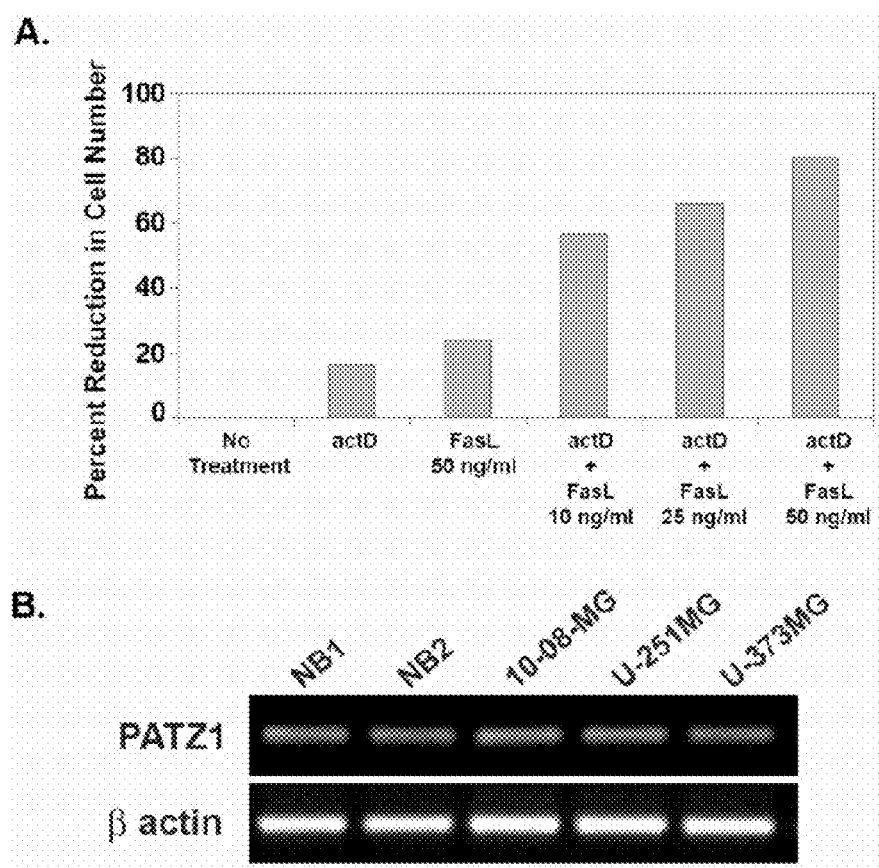
FIG. 12 shows screening data collected with glioma cells to demonstrate their resistance to FasL-induced apoptosis and the presence of PATZ1 mRNA. (A) Relative to those given no treatment, the percentage reduction in viable cell number by MTT assay is shown for U-87MG glioma cells when treated with actinomycin D (actD), FasL, or both. Percentage reductions in U-87MG viable cell number are given for treatments with actD (0.02 µg/ml), FasL (50 ng/ml), or both with FasL titrated from 10 to 50 ng/ml. (B) PATZ1 mRNA levels are shown for extracts from two different normal brain (NB) specimens (lanes 1, 2) and three gliomas (10-08-MG, U-251MG, U-373MG in lanes 3-5, respectively). Beta-actin loading controls are shown at the bottom.

A panel of 5 glioma cell lines, 10-08-MG, U-87MG, U-251MG, U-373MG, and T98G, met these criteria and was used for the subsequent studies. All 5 cell lines displayed resistance to apoptosis in vitro when FasL (10-150 ng/ml) was added to the supernatants, but the resistance was not noted upon the simultaneous addition of low concentrations of actD (0.02-0.1 ug/ml) (FIG. 12A). The 10-08-MG cell line was the most resistant, and U-87MG and T98G cell lines were the least resistant (FIG. 12A). The concentration of FasL for each particular glioma cell line that resulted in >30% killing in the presence of actD was chosen for use in the subsequent experiments testing the downregulation of PATZ1 with siRNA. Additionally, three glioma cell lines were found to express transcript variant 2 of the PATZ1 gene (NM_032050) and the gene was not over expressed compared to normal human brain tissue (FIG. 12B). PATZ1 siRNA decreases PATZ1 expression and increases sensitivity to FasL-mediated apoptosis in glioma cells.

Figure 6:
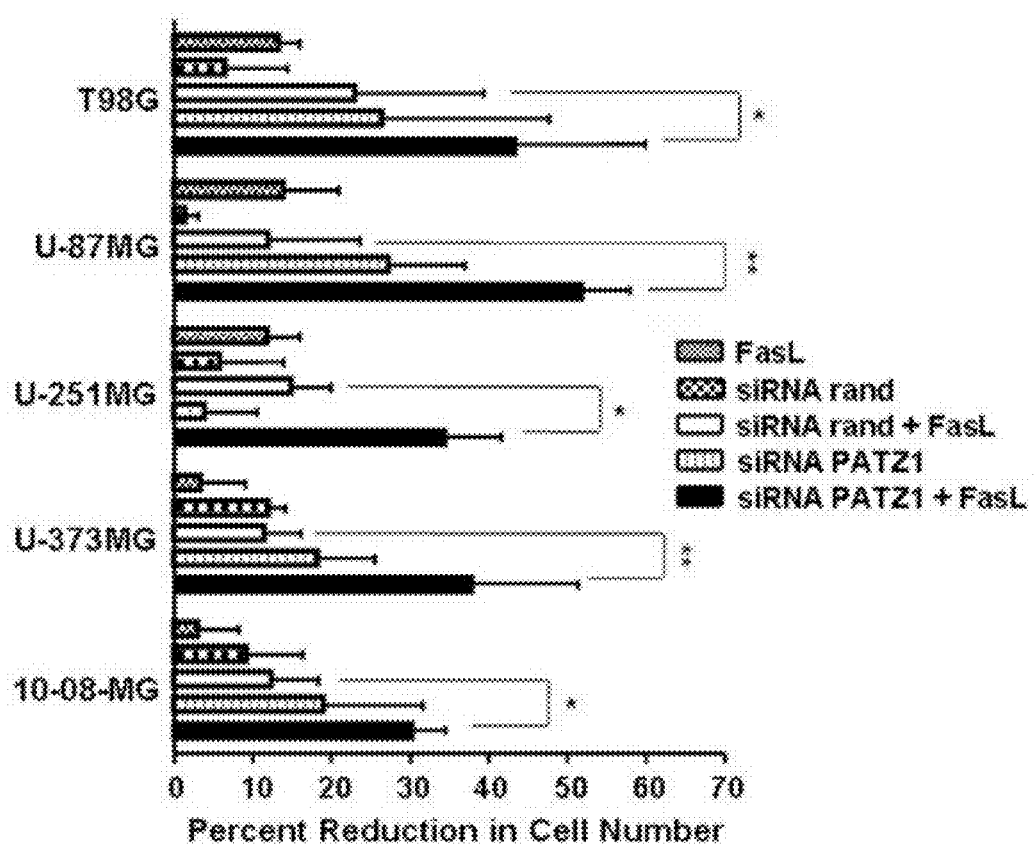
FIG. 6 shows reductions in viable cell number by MTT assay following siRNA-mediated downregulation of PATZ1 in human glioma cell lines and exposure to FasL.
Figure 7:
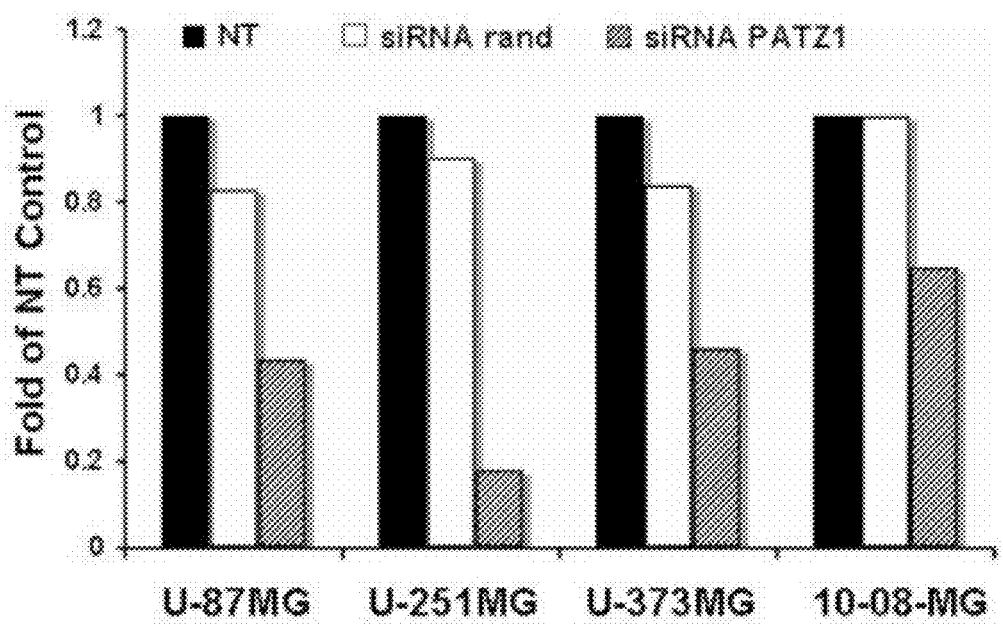
FIG. 7 shows a RT-PCR analysis of PATZ1 gene knockdown in glioma cells after transfection with siRNA.

The effect of PATZ1 siRNA on PATZ1 mRNA was determined for initial validation. When glioma cell lines were transfected with PATZ1 siRNA, expression of PATZ1 mRNA was reduced 2-3 fold compared to cells transfected with control siRNA or to nontransfected cells (FIG. 6). The effect of PATZ1 siRNA on FasL-mediated cell death was tested. Initial MTT assays showed that glioma cell lines transfected with PATZ1 siRNA and treated with FasL exhibited significantly reduced cell numbers (FIG. 7). The approximate 30% to 50% reductions in cell number differed significantly from those of the most relevant control, cells transfected with randomized control siRNA. There was also an observed reduction in cell numbers in those populations transfected with PATZ1 siRNA with no FasL added. The randomized control with FasL treatment.

Figure 8:
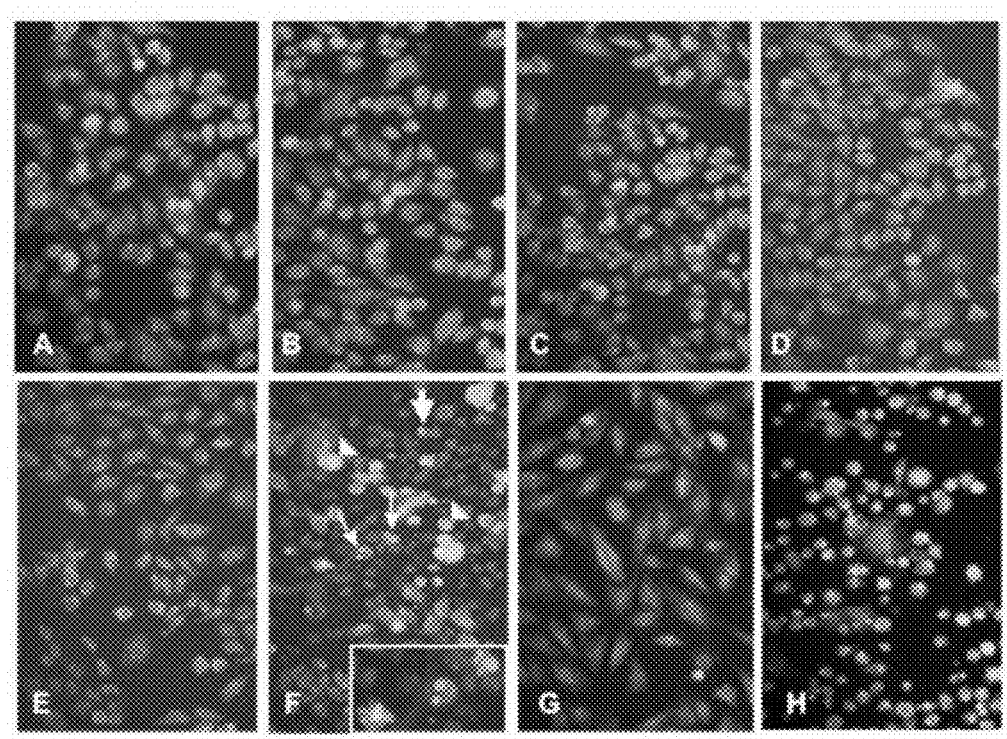
FIG. 8 shows Glioma cells detected by fluorescence microscopy after undergoing a morphologic assay for apoptosis by acridine orange/ethidium bromide staining.

Glioma cells were then assessed for apoptosis by the acridine orange/ethidium bromide morphologic assay. FIG. 8 shows fluorescent photomicrographs demonstrating low basal levels of apoptotic cells within the nontransfected U-251 MG cells in the presence or absence of FasL and in U-251MG cells transfected with the control Luc siRNA in the presence or absence of FasL. Similarly U-251 MG cells transfected with PATZ1 siRNA alone show very few cells with condensed or disintegrated nuclei. In contrast, PATZ1 siRNA transfected U-251MG cells exposed to FasL demonstrate many apoptotic cells. An even larger number of apoptotic cells was visible in U-87MG cells transfected with PATZ1 siRNA exposed to FasL, whereas U-373MG glioma cells similarly transfected with PATZ1 siRNA and exposed to FasL were seemingly resistant to apoptosis.

Figure 9:
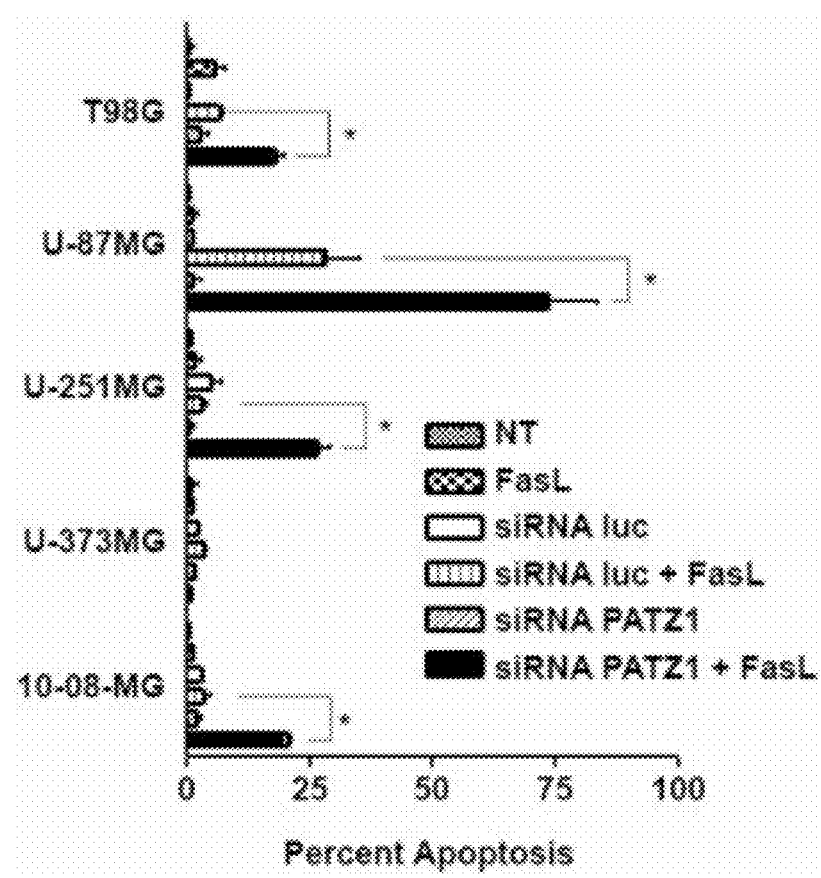
FIG. 9 shows percentages of apoptotic glioma cells from nontransfected (NT) or siRNA-transfected glioma cells (luc or PATZ1), treated or untreated with FasL.

The percentages of apoptotic cells were determined by counting the number of condensed or disintegrated nuclei for 200 cells in each of two different high power fields (FIG. 9). The apoptotic percentages for three other glioma cell lines were similar to that for U-251 MG and correspond to about two thirds of the effect seen in the MTT assays (see FIG. 6). In contrast to 10-08-MG, U-251MG, U-87MG, and T98G the U-373MG cell line appeared resistant to FasL-induced apoptosis after transfection with the PATZ1 siRNA but showed a significant reduction in cell number by MTT assay. This result suggested that the downregulation of PATZ1 and treatment with FasL in the U-373MG cell line is anti-proliferative. This result prompted investigations to determine whether downregulation of the PATZ1 gene in U-373MG had any effect on the expression levels of genes involved with death receptor mediated apoptosis.

Example 25

Figure 10:
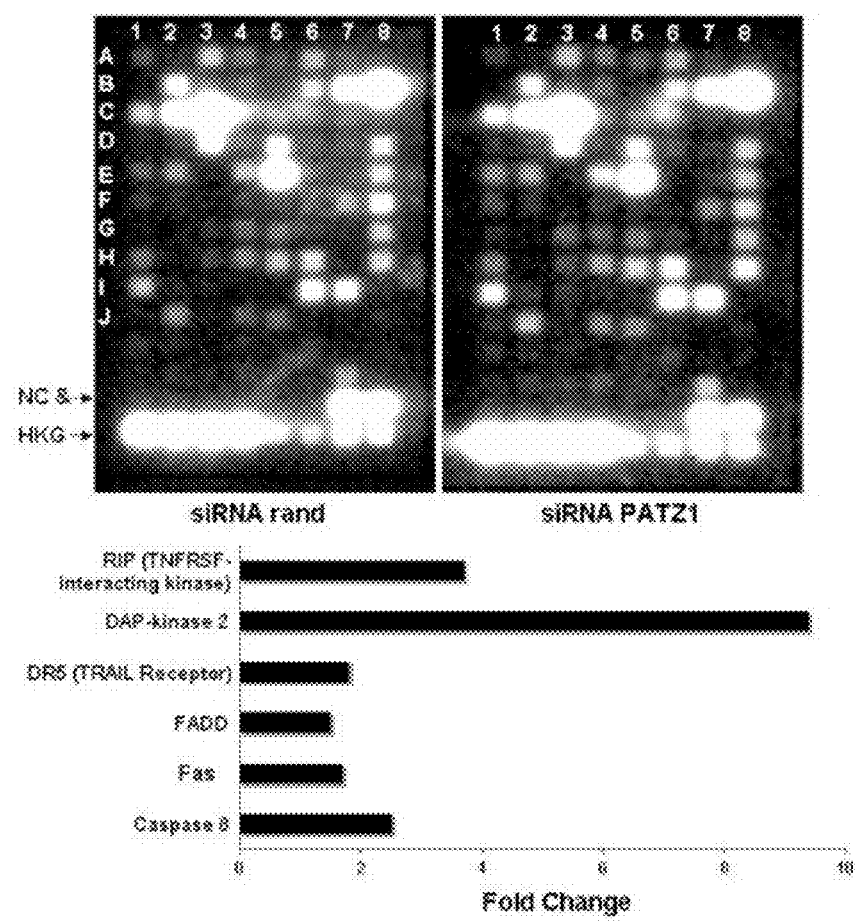
FIG. 10 shows apoptotic-pathway specific microarrays of U-373MG gliomas cells transfected with a randomized siRNA or siRNA to PATZ1.

Downregulation of PATZ1 Increases the Expression of Several Genes Associated with the Extrinsic Apoptosis Pathway PATZ1 has been identified as a transcriptional repressor. Therefore, downregulation of this gene should cause an increase in the expression level of genes it normally represses. The effect of PATZ1 on the expression level of other genes involved in death receptor apoptosis was tested using an apoptosis pathway-specific cDNA microarray which was probed with total RNA isolated from U-373MG cells transfected with either siRNA against PATZ1 or to the randomized control sequence (FIG. 10). The microarray data indicate six genes normally linked to the death receptor apoptosis pathway were up-regulated in the PATZ1 siRNA-transfected cells compared to the control. The six genes include RIP, DAP-kinase 2, FADD, Fas receptor, caspase 8, and DR5, which is the TRAIL receptor (Knight et al, 2001). None of the members of the Bcl-2 or inhibitor of apoptosis (IAP) gene families showed changes in their expression levels.

Example 26

Downregulation of PATZ1 Decreases Cell Growth/Increases Apoptosis by Trail

Figure 11:
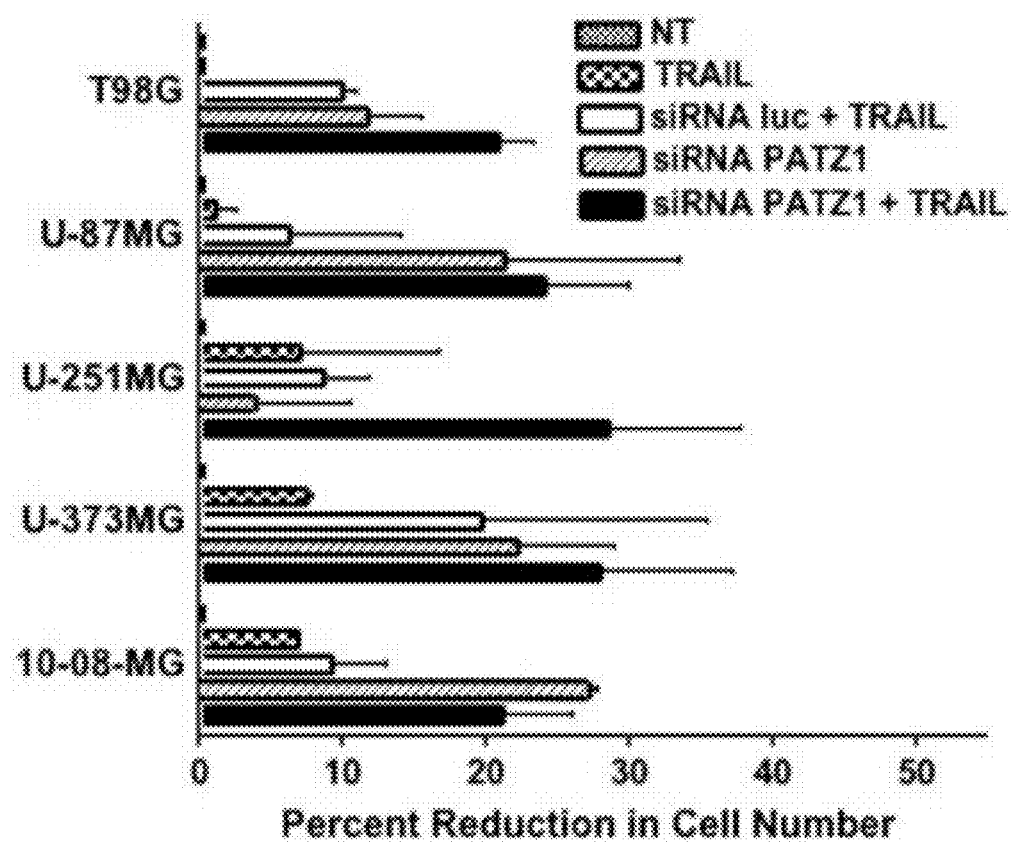
FIG. 11 shows anti-proliferative effects following downregulation of PATZ1 in human glioma cell lines and exposure to TRAIL.
Figure 13:
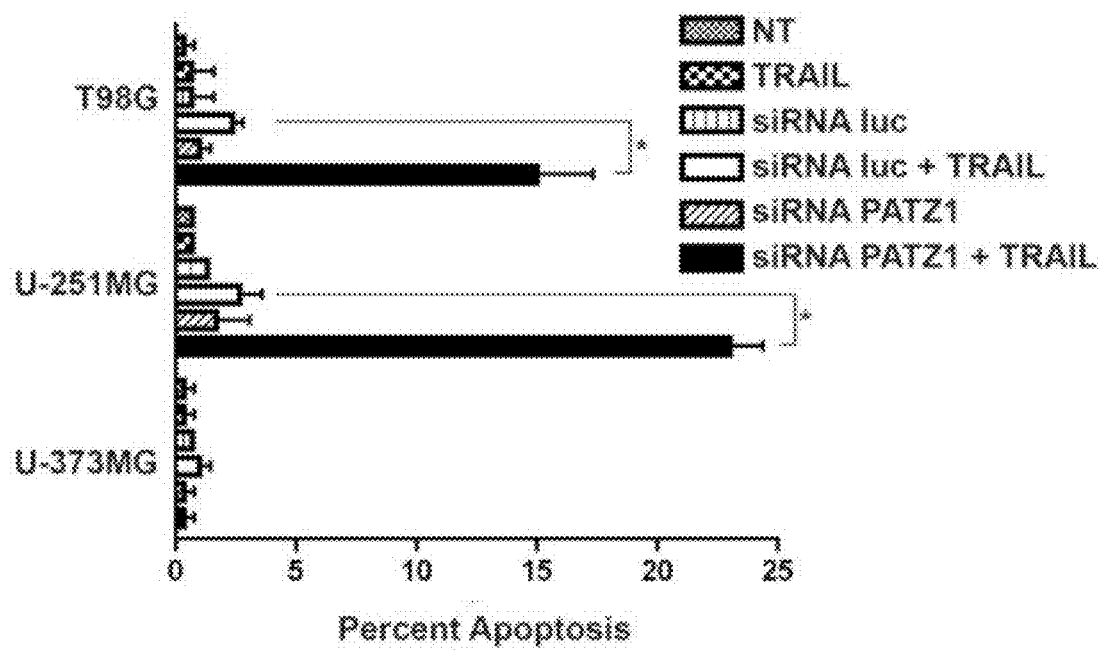
FIG. 13 shows percentages of apoptotic glioma cells from nontransfected (NT) or siRNA-transfected glioma cells (luc or PATZ1), treated or untreated with TRAIL as determined from apoptotic cells counted by fluorescence microscopy after staining with acridine orange/ethidiium bromide. Nontransfected T98G, U-251 MG and U-373MG glioma cells were or were not exposed to TRAIL, or the cells were transfected with a luciferase (luc) control siRNA or siRNA targeting the PATZ1 gene that were or were not exposed to TRAIL. At 48 hr post transfection TRAIL ligand was added at 200 ng/ml for T98G or 300 ng/ml for U-373MG and U-251 MG. The percentage of apoptotic cells are given plus or minus the standard error of the mean. Statistical differences at $*p \leq 1.0.001$ were obtained between TRAIL-treated siRNA transfected PATZ1 cells vs the TRAIL-treated siRNA luc transfected cells where shown, after the data were analyzed by a 2 way-ANOVA and Bonferroni post-hoc tests.

The effect of downregulation of PATZ1 on cell proliferation by TRAIL was determined using an MTT assay. The gliomas from the cell panel were transfected with the siRNA to PATZ1 or with the siRNA to the control luc sequence. The concentration of TRAIL for each particular glioma cell line (FIG. 11) that resulted in >30% killing in the presence of actD was selected for testing the downregulation of PATZ1 with siRNA. Two of the five cell lines, T98G and U-251 MG showed decreased cell proliferation when TRAIL was added to the PATZ1 siRNA transfected cells (FIG. 11). The U-87MG, U-373MG and 10-08-MG cell lines remained resistant to TRAIL. The acridine orange/ethidium bromide morphologic assay similarly confirmed the findings of the MTT assay with three of the cell lines tested. The U-251 MG and T98G cell lines showed sensitivity to TRAIL induced apoptosis when the PATZ1 gene was downregulated, while the U-373MG cell line remained resistant to TRAIL induced apoptosis (FIG. 13).

Example 27

Discussion of PATZ1 Results

Previous studies in glioma cells indicated that glioma cell lines could vary in their resistance to apoptosis induced by FasL or TRAIL (Knight et al., 2001). Data here confirms those findings. Fas/FasL-resistant glioma cells were shown to be activated to undergo apoptosis after cotreatment with actD and FasL. This finding demonstrated the feasibility of identifying a panel of glioma cells that were resistant to apoptosis upon addition of FasL, but still had the ability to undergo apoptosis after Fas ligation. It also indicated that the cells were likely resistant to apoptosis due to the synthesis of inhibitors. Such inhibitors could be targeted.

Provided herein is a novel target gene, that when downregulated, sensitized Fas/FasL-resistant glioma cells to killing by FasL. This gene is the BTB/POZ AT hook zinc finger protein 1 (PATZ1) and was identified after screening a ribozyme library for targets that when down-regulated converted Fas-resistant to Fas-sensitive cells (Tritz et al, 2005). Glioma cells express transcript variant 2 of the PATZ1 gene and this gene is not overexpressed in tumor cell lines versus normal brain tissue (FIG. 12B).

The downregulation of PATZ1 by siRNA exhibited anti-tumor effects on a panel of glioma cell lines. Cells transfected with PATZ1 siRNA and treated with FasL showed a 30-50% reduction in cell number and viability by MTT assay. The activation of apoptosis by FasL was observed in cells transfected with PATZ siRNA for 4 out of 5 cell lines. The random siRNA transfected cells with or without FasL showed a much lower level of apoptosis compared to the reduction in numbers seen in the MTT assay. This could be due to background in the MTT assay caused by an acute transfection toxicity that is not detected in the subsequent apoptosis assay because of the medium change after transfection.

A luciferase siRNA was selected as a negative control for the morphology and TRAIL studies in anticipation of using the luc siRNA in future animal studies. The background activity was comparable between the random and luciferase controls.

The apoptotic index calculated for four of the cell lines could account for approximately 65% of the effect detected in the MTT assay. The PATZ1 only transfected cells showed a greater effect in the MTT assay than the control+FasL although the apoptotic index was very low. This indicates that the downregulation of PATZ1 may also have an anti-proliferative component. This was further reinforced by the results obtained with the U-373MG cell line. The U-373MG cell line showed a significant reduction in cell number and viability in the MTT assay but showed little to no apoptosis in the acridine orange/ethidium bromide morphology assay. It is possible that the U-373MG cell number was reduced by a mechanism for programmed cell death other than apoptosis. Triggering the Fas receptor in Fas-resistant cells has also been shown to cause cells to die by necrosis (Hetz et al., 2002). These studies, however, did not indicate an increase in cell death by trypan blue dye staining (data not shown). It has also recently been shown that engaging the Fas receptor in cells that are resistant to Fas-induced apoptosis can enhance cellular proliferation (Barnhart et al., 2004; Mitsiades et al., 2006) and perhaps activate invasion in vivo (Kleber et al., 2008).

The studies examining an apoptosis gene specific cDNA microarray suggested that downregulating the PATZ1 gene can cause the upregulation of genes involved in death receptor mediated apoptosis. The studies also indicated that possibility that upregulation of the TRAIL receptor and downregulation of PATZ1 could sensitize cells to TRAIL induced apoptosis. The results from the TRAIL experiments were encouraging and consistent with the results for FasL. They indicate that downregulating the PATZ1 gene can generally sensitize cells to death receptor mediated apoptosis.

Thus, the PATZ1 gene encodes a transcription factor that belongs to the BTB/POZ group of transcriptional regulators and has been implicated as a transcriptional repressor. Cloned cDNA from glioma cell lines expressed transcript variant 2 of PATZ1. A specific siRNA against PATZ1 but not a control randomized siRNA, greatly reduced PATZ1 expression in glioma cells as determined by quantitative PCR. In a panel of human glioma cell lines incubated with proapoptotic FasL, PATZ1 siRNA resulted in inhibition of cell growth as determined by the MTT colorimetric assay. Further studies showed that in the cell lines 10-08-MG, U-251MG, U-87MG, and T98G PATZ1 siRNA significantly increased apoptosis in response to incubation with soluble FasL, as shown by a morphologic acridine orange/ethidium bromide apoptotic assay. Using an apoptosis specific cDNA microarray assays further demonstrated that down-regulation of PATZ1 by siRNA resulted in the upregulation of death receptor pro-apoptotic genes including caspase 8 and Decoy Receptor 5 (DR5) in U-373MG cells. Since DR5 is the receptor for TRAIL PATZ1 downregulation was tested for sensitizing cells to TRAIL-induced apoptosis. PATZ1 siRNA, but not control siRNA, sensitized U-251 MG and T98G glioma cells to TRAIL-induced apoptosis. Altogether, these data demonstrate a previously unknown role for the transcription factor PATZ1 in conferring resistance to apoptosis and indicate that modulation of PATZ1 expression may be a therapeutic strategy for gliomas.

Citations for Examples 17-27

1. Stupp R, Mason W P, van den Bent M J, Weller M, Fisher B, Taphoorn M J, Belanger K, Brandes A A, Marosi C, Bogdahn U, Curschmann J, Janzer R C, Ludwin S K, Gorlia T, Allgeier A, Lacombe D, Cairncross J G, Eisenhauer E, Mirimanoff R O. Radiotherapy plus concomitant and adjuvant temozolomide for glioblastoma. N Engl J Med 352(10): 987-96, 2005.
2. Hutterer M, Knyazev P, Abate A, Reschke M, Maier H, Stefanova N, Knyazeva T, Barbieri V, Reindl M, Muigg A, Kostron H, Stockhammer G, Ullrich A. Axl and growth arrest-specific gene 6 are frequently overexpressed in human gliomas and predict poor prognosis in patients with glioblastoma multiforme. Clin Cancer Res 14(1): 130-8, 2008.
3. CBTRUS. Statistical Report: Primary Brain Tumors in the United States, 1998-2002. In Central Brain Tumor Registry of the United States, 2005.
4. Greenlee R, Murray T, Bolden S, Wingo P. Cancer statistics, 2000. CA Cancer J Clin 50(1): 7-33, 2000.

5. Barnhart B C, Legembre P, Pietras E, Bubici C, Franzoso G, Peter M E. CD95 ligand induces motility and invasiveness of apoptosis-resistant tumor cells. Embo J 23(15): 3175-85, 2004.
6. Riffkin C D, Gray A Z, Hawkins C J, Chow C W, Ashley D M. Ex vivo pediatric brain tumors express Fas (CD95) and FasL (CD95L) and are resistant to apoptosis induction. Neuro Oncol 3(4): 229-40, 2001.
7. Muschen M, Re D, Betz B, Moers C, Wolf J, Niederacher D, Diehl V, Beckmann M W. Resistance to CD95-mediated apoptosis in breast cancer is not due to somatic mutation of the CD95 gene. Int J Cancer 92(2): 309-10, 2001.
8. Maecker H L, Yun Z, Maecker H T, Giaccia A J. Epigenetic changes in tumor Fas levels determine immune escape and response to therapy. Cancer Cell 2(2): 139-48, 2002.
9. Yang B, Lin H, Hor W, Hwang J, Lin Y, Liu M, Wang Y. Mediation of enhanced transcription of the IL-10 gene in T cells, upon contact with human glioma cells, by Fas signaling through a protein kinase A-independent pathway. J Immunol 171(8): 3947-3954, 2003.
10. Foehr E D, Lorente G, Vincent V, Nikolich K, Urfer R. FAS associated phosphatase (FAP-1) blocks apoptosis of astrocytomas through dephosphorylation of FAS. J Neurooncol 74(3): 241-8, 2005.
11. Gomez G G, Kruse C A. Mechanisms of malignant glioma immune resistance and sources of immunosuppression. Gene Ther Mol Biol 10(a): 133-146, 2006.
12. Gomez G G, Varella-Garcia, M-L, Kruse, C A. Isolation of immunoresistant human glioma cell clones after immunoselection with alloreactive cytotoxic T lymphocytes: cytogenetic and molecular cytogenetic characterization. Cancer Genetics Cytogenetics, 165, 121-134, 2006.
13. Merlo A. Genes and pathways driving glioblastomas in humans and murine disease models. Neurosurg Rev 26(3): 145-58, 2003.
14. Tritz R, Habita C, Robbins J M, Gomez G G, Kruse C A. Catalytic nucleic acid enzymes for the study and development of therapies in the central nervous system: Review Article. Gene Ther Mol Biol 9A, 89-106, 2005.
15. Zollman S, Godt D, Prive G G, Couderc J L, Laski F A. The BTB domain, found primarily in zinc finger proteins, defines an evolutionarily conserved family that includes several developmentally regulated genes in *Drosophila*. Proc Natl Acad Sci USA 91(22): 10717-21, 1994.
16. Bardwell V J, Treisman R. The POZ domain: a conserved protein-protein interaction motif. Genes Dev 8(14): 1664-77, 1994.
17. Fedele M, Benvenuto G, Pero R, Majello B, Battista S, Lembo F, Vollono E, Day P M, Santoro M, Lania L, Bruni C B, Fusco A, Chiariotti L. A novel member of the BTB/POZ family, PATZ, associates with the RNF4 RING finger protein and acts as a transcriptional repressor. J Biol Chem 275(11): 7894-901, 2000.
18. Mastrangelo T, Modena P, Tornielli S, Bullrich F, Testi M A, Mezzelani A, Radice P, Azzarelli A, Pilotti S, Croce C M, Pierotti M A, Sozzi G. A novel zinc finger gene is fused to EWS in small round cell tumor. Oncogene 19(33): 3799-804, 2000.
19. Mitchelmore C, Kjaerulff K M, Pedersen H C, Nielsen J V, Rasmussen T E, Fisker M F, Finsen B, Pedersen K M, Jensen N A. Characterization of two novel nuclear BTB/POZ domain zinc finger isoforms. Association with differentiation of hippocampal neurons, cerebellar granule cells, and macroglia. J Biol Chem 277(9): 7598-609, 2002.
20. Pero R, Lembo F, Palmieri E A, Vitiello C, Fedele M, Fusco A, Bruni C B, Chiariotti L. PATZ attenuates the RNF4-mediated enhancement of androgen receptor-dependent transcription. J Biol Chem 277(5): 3280-5, 2002.
21. Fedele M, Franco R, Salvatore G, Paronetto M, Barbagallo F, Pero R, Chiariotti L, Sette C, Tramontano D, Chieffi G, Fusco A, Chieffi P. PATZ1 gene has a critical role in the spermatogenesis and testicular tumours. J Pathol 2008.
22. Knight M J, Riffkin C D, Muscat A M, Ashley D M, Hawkins C J. Analysis of FasL and TRAIL induced apoptosis pathways in glioma cells. Oncogene 20(41): 5789-98, 2001.
23. Hetz C A, Hunn M, Rojas P, Torres V, Leyton L, Quest A F. Caspase-dependent initiation of apoptosis and necrosis by the Fas receptor in lymphoid cells: onset of necrosis is associated with delayed ceramide increase. J Cell Sci 115 (Pt 23): 4671-83, 2002.
24. Mitsiades C S, Poulaki V, Fanourakis G, Sozopoulos E, McMillin D, Wen Z, Voutsinas G, Tseleni-Balafouta S, Mitsiades N. Fas signaling in thyroid carcinomas is diverted from apoptosis to proliferation. Clin Cancer Res 12(12): 3705-12, 2006.
25. Kleber S, Sancho-Martinez I, Wiestler B, Beisel A, Gieffers C, Hill O, Thiemann M, Mueller W, Sykora J, Kuhn A, Schreglmann N, Letellier E, Zuliani C, Klussmann S, Teodorczyk M, Grone H J, Ganten T M, Sultmann H, Tuttenberg J, von Deimling A, Regnier-Vigouroux A, Herold-Mende C, Martin-Villalba A. Yes and PI3K bind CD95 to signal invasion of glioblastoma. Cancer Cell 13(3): 235-48, 2008.
26. Xia S, Li Y, Rosen E M, Laterra J. Ribotoxic stress sensitizes glioblastoma cells to death receptor induced apoptosis: requirements for c-Jun NH2-terminal kinase and Bim. Mol Cancer Res 5(8): 783-92, 2007.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3).

For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A method for inhibiting proliferation of brain tumor cells, which comprises:
   administering to brain tumor cells a siNA agent that reduces the amount of RNA encoding a Fas/FasL apoptosis gating polypeptide in an amount sufficient to inhibit proliferation of the brain tumor cells,
   wherein the Fas/FasL apoptosis gating polypeptide is a FAPP2 polypeptide or a PATZ1 polypeptide, and
   wherein the siNA agent comprises one or more of the nucleotide sequences:

```
                                         (SEQ ID NO: 26)
5'-GAUGGAUCUUGUUGGAAAUUU-3'

(SEQ ID NO: 27)
5'-AUUUCCAACAAGAUCCAUCUU-3'

(SEQ ID NO: 28)
5'-GAUGGAUCUUGUUGGAAAUUsU-3'

(SEQ ID NO: 29)
5'-AUUUCCAACAAGAUCCAUCUsU-3'

(SEQ ID NO: 30)
5'-GAuGGAucuuGuuGGAAAuusu-3'

(SEQ ID NO: 31)
5'-AUUUCcAACAAGAUCcAUCUsU-3'

(SEQ ID NO: 32)
5'-GUCUAUGGAAGAAAUAGUUUU-3'

(SEQ ID NO: 33)
5'-UUACUACUACUACUACUACUU-3'

(SEQ ID NO: 34)
5'-GUCUAUGGAAGAAAUAGUUUsU-3'

(SEQ ID NO: 35)
5'-UUACUACUACUACUACUACUsU-3'

(SEQ ID NO: 36)
5'-GucuAuGGAAGAAAuAGuuusU-3'

(SEQ ID NO: 37)
5'-UuACuACuACuACuACuACuACuSU-3'
``` wherein s is a phosphorothioate linkage and lowercase nucleotide designations designate a nucleotide having a 2'-O-methyl modification.

2. The method of claim 1, wherein the brain tumor cells comprise glioma cells.

3. The method of claim 1, wherein the brain tumor cells are glioma cells.

4. The method of claim 2, wherein the brain tumor cells are human cells.

5. The method of claim 3, wherein the brain tumor cells are human cells.

6. The method of claim 4, wherein the reduction of FAPP2 polypeptide or PATZ1 polypeptide sensitizes the cells to Fas or FasL mediated apoptosis.

7. The method of claim 5, wherein the reduction of FAPP2 polypeptide or PATZ1 polypeptide sensitizes the cells to Fas or FasL mediated apoptosis.

8. The method of claim 6, wherein a FAPP2 targeted ribozyme comprises the nucleotide sequence:

```
                                         (SEQ ID NO: 1)
5'-NNNNNNNCUGAUGAGpdpdpdpdCGAANNNNNNNNN-3'.
``` wherein N indicates any of DNA bases A, C, G, T, or any of RNA bases A, C, G, U, or any of 2'-O-methylated RNA bases A, C, G, U,
   wherein A, C, G, indicate DNA bases A, C, G, or RNA bases A, C, G, or 2'-O-methyl RNA bases A, C, G,
   wherein U indicates a RNA base U or 2'-O-methyl RNA base U, and
   wherein pd indicates propanediol linkage.

9. The method of claim 6, wherein the siNA is siRNA.

10. The method of claim 9, wherein the siRNA comprises a phosphorothioate linkage.

11. The method of claim 10, wherein the siRNA comprises a 2'-O-methyl modification.

12. The method of claim 9, wherein the FAPP2 targeted siRNA comprises one or both of the nucleotide sequences:

```
                                         (SEQ ID NO: 26)
5'-GAUGGAUCUUGUUGGAAAUUU-3'

(SEQ ID NO: 27)
5'-AUUUCCAACAAGAUCCAUCUU-3'.
```

13. The method of claim 10, wherein the FAPP2 targeted siRNA comprises one or both of the nucleotide sequences:

```
                                         (SEQ ID NO: 28)
5'-GAUGGAUCUUGUUGGAAAUUsU-3'

(SEQ ID NO: 29)
5'-AUUUCCAACAAGAUCCAUCUsU-3'
``` wherein s is a phosphorothioate linkage.

14. The method of claim 11, wherein the FAPP2 targeted siRNA comprises one or both of the nucleotide sequences:

```
                                         (SEQ ID NO: 30)
5'-GAuGGAucuuGuuGGAAAuusu-3'

(SEQ ID NO: 31)
5'-AUUUCcAACAAGAUCcAUCUsU-3'
``` wherein s is a phosphorothioate linkage and lowercase nucleotide designations designate a nucleotide having a 2'-O-methyl modification.

15. The method of claim 9 wherein the PATZ1 targeted siRNA comprises one or more of the nucleotide sequences:

```
                                         (SEQ ID NO: 32)
5'-GUCUAUGGAAGAAAUAGUUUU-3'

(SEQ ID NO: 33)
5'-UUACUACUACUACUACUACUU-3'.
```

16. The method of claim 10, wherein the PATZ1 targeted siRNAi comprises one or more of the nucleotide sequences:

```
                                         (SEQ ID NO: 34)
5'-GUCUAUGGAAGAAAUAGUUUsU-3'

(SEQ ID NO: 35)
5'-UUACUACUACUACUACUACUsU-3'
``` wherein s is a phosphorothioate linkage.

17. The method of claim 11, wherein the PATZ1 targeted siRNA comprises one or more of the nucleotide sequences:

```
                                         (SEQ ID NO: 36)
5'-GucuAuGGAAGAAAuAGuuusU-3'

(SEQ ID NO: 37)
5'-UuACuACuACuACuACuACuSU-3'
``` wherein s is a phosphorothioate linkage and lowercase nucleotide designations designate a nucleotide having a 2'-O-methyl modification.

18. A method for treating a brain tumor in a subject, which comprises:
administering to a subject in need thereof a siNA agent that reduces the amount of RNA encoding a FAPP2 polypeptide or a PATZ1 polypeptide in an amount sufficient to inhibit proliferation of cells in the brain tumor in the subject,
wherein the siNA agent comprises comprises one or more of the nucleotide sequences:

```
                                    (SEQ ID NO: 26)
5'-GAUGGAUCUUGUUGGAAAUUU-3'

(SEQ ID NO: 27)
5'-AUUUCCAACAAGAUCCAUCUU-3'

(SEQ ID NO: 28)
5'-GAUGGAUCUUGUUGGAAAUUsU-3'

(SEQ ID NO: 29)
5'-AUUUCCAACAAGAUCCAUCUsU-3'

(SEQ ID NO: 30)
5'-GAuGGAucuuGuuGGAAAuusu-3'

(SEQ ID NO: 31)
5'-AUUUCcAACAAGAUCcAUCUsU-3'

(SEQ ID NO: 32)
5'-GUCUAUGGAAGAAAUAGUUUU-3'

(SEQ ID NO: 33)
5'-UUACUACUACUACUACUACUU-3'

(SEQ ID NO: 34)
5'-GUCUAUGGAAGAAAUAGUUUsU-3'

(SEQ ID NO: 35)
5'-UUACUACUACUACUACUACUsU-3'

(SEQ ID NO: 36)
5'-GucuAuGGAAGAAAuAGuuusU-3'

(SEQ ID NO: 37)
5'-UuACuACuACuACuACuACUsU-3'
``` wherein s is a phosphorothioate linkage and lowercase nucleotide designations designate a nucleotide having a 2'-O-methyl modification.

19. A method for treating a brain tumor in a subject, which comprises administering to a subject in need thereof a ribozyme that reduces the amount of RNA encoding a FAPP2 polypeptide or a PATZ1 polypeptide in an amount sufficient to inhibit proliferation of cells in the brain tumor in the subject,
wherein the ribozyme comprises one or more of the nucleotide sequences:

```
                                    (SEQ ID NO: 26)
5'-GAUGGAUCUUGUUGGAAAUUU-3'

(SEQ ID NO: 27)
5'-AUUUCCAACAAGAUCCAUCUU-3'

(SEQ ID NO: 28)
5'-GAUGGAUCUUGUUGGAAAUUsU-3'

(SEQ ID NO: 29)
5'-AUUUCCAACAAGAUCCAUCUsU-3'

(SEQ ID NO: 30)
5'-GAuGGAucuuGuuGGAAAuusu-3'

(SEQ ID NO: 31)
5'-AUUUCcAACAAGAUCcAUCUsU-3'

(SEQ ID NO: 32)
5'-GUCUAUGGAAGAAAUAGUUUU-3'

(SEQ ID NO: 33)
5'-UUACUACUACUACUACUACUU-3'

(SEQ ID NO: 34)
5'-GUCUAUGGAAGAAAUAGUUUsU-3'

(SEQ ID NO: 35)
5'-UUACUACUACUACUACUACUsU-3'

(SEQ ID NO: 36)
5'-GucuAuGGAAGAAAuAGuuusU-3'

(SEQ ID NO: 37)
5'-UuACuACuACuACuACuACUsU-3'
``` wherein s is a phosphorothioate linkage and lowercase nucleotide designations designate a nucleotide having a 2'-O-methyl modification.

20. A composition comprising the nucleic acid:

```
                                                    (SEQ ID NO: 1)
5'-NNNNNNNNCUGAUGAGpdpdpdpdCGAANNNNNNNNNN-3'
``` wherein N indicates any of DNA bases A, C, G, T, or any of RNA bases A, C, G, U, or any of 2'-O-methylated RNA bases A, C, G, U,
wherein A, C, G, indicate DNA bases A, C, G, or RNA bases A, C, G, or 2' 0-methyl RNA bases A, C, G,
wherein U indicates a RNA base U or 2'-O-methyl RNA base U, and
wherein pd indicates propanediol linkage.

21. A composition comprising one or both of the following nucleic acids:

```
                                    (SEQ ID NO: 30)
5'-GAuGGAucuuGuuGGAAAuusu-3'

(SEQ ID NO: 31)
5'-AUUUCcAACAAGAUCcAUCUsU-3'
``` wherein s is a phosphorothioate linkage and lowercase nucleotide designations designate a nucleotide having a 2'-O-methyl modification.

22. A composition comprising one or both of the following nucleic acids:

```
                                    (SEQ ID NO: 36)
5'-GucuAuGGAAGAAAuAGuuusU-3'

(SEQ ID NO: 37)
5'-UuACuACuACuACuACuACUsU-3'
``` wherein s is a phosphorothioate linkage and lowercase nucleotide designations designate a nucleotide having a 2'-O-methyl modification.

* * * * *

SEQUENCE LISTING

```
<160> NUMBER OF SEQ ID NOS: 55

<210> SEQ ID NO 1
<211> LENGTH: 28
<212> TYPE: DNA
<213> ORGANISM: Artificial Sequence
<220> FEATURE:
<223> OTHER INFORMATION: RIBOZYME:  A,G,C,T indicate DNA bases, A,G,C,U
      indicate RNA bases, A,G,C,U indicate 2' O methyl RNA
<220> FEATURE:
<221> NAME/KEY: misc_feature
<222> LOCATION: (1)..(7)
<223> OTHER INFORMATION: n is a, c, g, t or u
<220> FEATURE:
<221> NAME/KEY: misc_feature
<222> LOCATION: (15)..(16)
<223> OTHER INFORMATION: 4 propanediol linkages between G and C
<220> FEATURE:
<221> NAME/KEY: misc_feature
<222> LOCATION: (20)..(28)
<223> OTHER INFORMATION: n is a, c, g, t or u

<400> SEQUENCE: 1
nnnnnnncug augagcgaan nnnnnnnn                                       28

<210> SEQ ID NO 2
<211> LENGTH: 28
<212> TYPE: DNA
<213> ORGANISM: Artificial Sequence
<220> FEATURE:
<223> OTHER INFORMATION: RIBOZYME: A,G,C,T indicate DNA bases, A,G,C,U
      indicate RNA bases, A,G,C,U indicate 2' O methyl RNA
<220> FEATURE:
<221> NAME/KEY: misc_feature
<222> LOCATION: (15)..(16)
<223> OTHER INFORMATION: 4 propanediol linkages

<400> SEQUENCE: 2
atactgucug augagcgaaa ctataatt                                       28

<210> SEQ ID NO 3
<211> LENGTH: 1928
<212> TYPE: RNA
<213> ORGANISM: Homo sapiens

<400> SEQUENCE: 3
gccgccugcg accggcagcu cguucgccgc acuuuggagg cuucggcugc cccuccgacc    60
cacguagggc ccggacccgg gccuccuugu gaacagcgug ccggcuucgc cccacggguu   120
caccggcugg cugggcuuca agcgccgagg ccgccgcagu gaccccgccc ccgggccgag   180
gaugugaggc gggccgggcg uccccacacc gggcccgggc gccgggagug ggcgucuggg   240
cagcgccagg cgauggcccu gcugcuggug cuccucgccu cuuggggccu ggggcaguga   300
gggggccggc gggcgugggc cgaguggccg cgggcgccau ggaggggug cuguacaagu   360 ggaccaacua ucugagcggu uggcagccuc gaugguuccu ucucuguggg ggaauauugu   420
ccuauuauga uucuccugaa gaugccugga aagguugcaa agggagcaua caaauggcag   480
ucugugaaau ucaaguucau ucuguagaua auacacgcau ggaccugaua aucccugggg   540
```

```
aacaguauuu cuaccugaag gccagaagug uggcugaaag acagcgguggg cugguggccc    600
ugggaucagc caaggcuugc cugacugaca guaggaccca gaaggagaaa gaguuugcug    660
aaaacacuga aacuugaaa accaaaaugu cagaacuaag acucuacugu gaccuccuug     720
uucagcaagu agauaaaaca aagaaguga ccacaacugg uguguccaau ucugaggagg     780
gaauugaugu gggaacuuug cugaaaucaa ccuguaauac uuuucugaag accuggaag     840
aaugcaugca gaucgcaaau gcagccuuca ccucugagcu gcucuaccgc acuccaccag    900
gaucacccuca gcuggccaug cucaaguca gcaagaugaa acauccuauu uaccaauuc    960
auaauucauu ggaaaggcaa auggaguuga gcacuguga aaauggaucu uuaaauaugg     1020
aaauaaaugg ugaggaagaa auccaauga aaaauaagaa uuccuuauau uugaaaucug     1080
cagagauaga cugcagcaua ucaagugagg aaaauacaga ugauaauaua acaguccaag    1140
gugaaauaag gaaggaagau ggaauggaaa accugaaaaa ucaugacaau aacuugacuc    1200
agucuggauc agacucaagu ugcucuccgg aaugccucug ggaggaaggc aaagaaguua    1260
ucccaacuuu cuuuaguacc augaacacaa gcuuuaguga cauugaacuu cuggaagaca    1320
guggcauucc cacagaagca uucuuggcau cauguuaugc ugugguucca guauuagaca    1380
aacuuggccc uacaguguuu gcuccuguua agauggaucu uguuggaaau auuaagaaag    1440
uaaaucagaa guauauaacc aacaaagaag aguuuaccac ucccagaag auagugcugc     1500
acgaagugga ggcggaugua gcccagguua ggaacucagc gacugaagcc cucuugluggc    1560
ugaagagagg ucucaaauuu uugaagggau uuugacaga aguugaaaau ggggagaagg     1620
auauccagac agcccuaaau aaugcauaug guaaaacauu gcggcaacac cauggcuggg    1680
uaguucgagg gguuuuugcg guguaggaau gugggugugag acggaaucuccc agaaaccauc    1740
auggaccaug aggcaacucu gaggauggaa gccacacacu aaggacggua aagcagaaag     1800
aagagcugaa acccugauga uaagaagca gccaauuccg uccugcacug cccaccucca     1860
gaucucauuc augugaaaca aagagaaacu uuaucuuguu caagucaaaa aaaaaaaaaa    1920
aaaaaaaa    1928

<210> SEQ ID NO 4
<211> LENGTH: 1928
<212> TYPE: DNA
<213> ORGANISM: Homo sapiens

<400> SEQUENCE: 4
gccgcctgcg accggcagct cgttcgccgc actttggagg cttcggctgc ccctccgacc    60
cacgtagggc ccggacccgg gcctccttgt gaacagcgtg ccggcttcgc cccacgggtt    120
caccggctgg ctgggcttca agcgccgagg ccgccgcagt gaccccgccc cgggccgag    180
gatgtgaggc gggccgggcg tccccacacc gggcccgggc gccggagtg ggcgtctggg    240
cagcgccagg cgatggccct gctgctggtg ctcctcgcct cttggggcct ggggcagtga    300
ggggccggc gggcgtgggc cgagtggccg cgggcgccat ggaggggtg ctgtacaagt     360
ggaccaacta tctgagcggt tggcagcctc gatggttcct tctctgtggg ggaatattgt    420
cctattatga ttctcctgaa gatgcctgga aaggttgcaa agggagcata caaatggcag    480
tctgtgaaat tcaagttcat tctgtagata atacacgcat ggacctgata atccctgggg    540
aacagtattt ctacctgaag gccagaagtg tggctgaaag acagcggtgg ctggtggccc    600
tgggatcagc caaggcttgc ctgactgaca gtaggaccca gaaggagaaa gagtttgctg    660
aaaacactga aacttgaaa accaaaatgt cagaactaag actctactgt gacctccttg    720
```

```
ttcagcaagt agataaaaca aaagaagtga ccacaactgg tgtgtccaat tctgaggagg    780
gaattgatgt gggaactttg ctgaaatcaa cctgtaatac tttctgaag accttggaag     840 aatgcatgca gatcgcaaat gcagccttca cctctgagct gctctaccgc actccaccag    900
gatcacctca gctggccatg ctcaagtcca gcaagatgaa acatcctatt ataccaattc    960
ataattcatt ggaaaggcaa atggagttga gcacttgtga aaatggatct ttaaatatgg   1020
aaataaatgg tgaggaagaa atcctaatga aaaataagaa ttccttatat ttgaaatctg   1080
cagagataga ctgcagcata tcaagtgagg aaaatacaga tgataatata acagtccaag   1140
gtgaaataag gaaggaagat ggaatggaaa acctgaaaaa tcatgacaat aacttgactc   1200
agtctggatc agactcaagt tgctctccgg aatgcctctg ggaggaaggc aaagaagtta   1260
tcccaacttt ctttagtacc atgaacacaa gctttagtga cattgaactt ctggaagaca   1320
gtggcattcc cacagaagca ttcttggcat catgttatgc tgtggttcca gtattagaca   1380
aacttggccc tacagtgttt gctcctgtta agatggatct tgttgaaat attaagaaag    1440 taaatcagaa gtatataacc aacaagaag agtttaccac tctccagaag atagtgctgc    1500
acgaagtgga ggcggatgta gcccaggtta ggaactcagc gactgaagcc ctcttgtggc   1560
tgaagagagg tctcaaattt ttgaagggat ttttgacaga agtgaaaaat ggggagaagg   1620
atatccagac agccctaaat aatgcatatg gtaaaacatt gcggcaacac catggctggg   1680
tagttcgagg ggttttgcg gtgtaggaat gtgggtgtag acggaactcc agaaaccatc    1740
atggaccatg aggcaactct gaggatgaa gccacacact aaggacggta aagcagaaag    1800
aagagctgaa accctgatga taaagaagca gccaattccg tcctgcactg cccacctcca   1860
gatctcattc atgtgaaaca aagagaaact ttatcttgtt caagtcaaaa aaaaaaaaa    1920 aaaaaaaa                                                            1928
```

<210> SEQ ID NO 5
<211> LENGTH: 1701
<212> TYPE: DNA
<213> ORGANISM: Homo sapiens

<400> SEQUENCE: 5

```
gcccttggat ccgccaccat ggaggggtg ctgtacaagt ggaccaacta tctgagcggt      60
tggcagcctc gatggttcct tctctgtggg ggaatattgt cctattatga ttctcctgaa    120
gatgcctgga aaggttgcaa agggagcata caaatggcag tctgtgaaat tcaagttcat    180
tctgtagata atacacgcat ggacctgata atccctgggg aacagtattt ctacctgaag    240
gccagaagtg tggctgaaag acagcggtgg ctggtggccc tgggatcagc caaggcttgc    300
ctgactgaca gtaggaccca gaaggagaaa gagtttgctg aaaacactga aacttgaaa    360 accaaaatgt cagaactaag actctactgt gacctccttg ttcagcaagt agataaaaca    420
aaagaagtga ccacaactgg tgtgtccaat tctgaggagg gaattgatgt gggaactttg    480
ctgaaatcaa cctgtaatac tttctgaag accttggaag aatgcatgca gatcgcaaat    540
gcagccttca cctctgagct gctctaccgc actccaccag gatcacctca gctggccatg    600
ctcaagtcca gcaagatgaa acatcctatt ataccaattc ataattcatt ggaaaggcaa    660
atggagttga gcacttgtga aaatggatct ttaaatatgg aaataaatgg tgaggaagaa    720
atcctaatga aaaataagaa ttccttatat ttgaaatctg cagagataga ctgcagcata    780
tcaagtgagg aaaatacaga tgataatata acagtccaag gtgaaataag gaaggaagat    840
ggaatggaaa acctgaaaaa tcatgacaat aacttgtctc agtctggatc agactcaagt    900
```

```
tgctctccag aatgcctctg ggaggaaggc aaagaagtta tcccaacttt ctttagtacc    960
atgaacacaa gctttagtga cattgaactt ctggaagaca gtggcattcc cacagaagca   1020
ttcttggcat catgttgtgc tgtggttcca gtattagaca aacttggccc tacagtgttt   1080
gctcctgtta agatggatct tgttgaaaat attaagaaag taaatcagaa gtatataacc   1140
aataaagaag agtttaccac tctccagaag atagtgctgc acgaagtgga ggcggatgta   1200
gcccaggtta ggaactcagc gactgaagcc ctcttgtggc tgaagagagg tctcaaattt   1260
ttgaagggat ttttgacaga agtgaaaaat ggggaaaagg atatccagac agccctgaat   1320
aacgcatatg gtaaaacatt gcggcaacac catggctggg tagttcgagg ggttttttgcg  1380 ttagctttaa gggcaactcc atcctatgaa gattttgtgg ccgcgttaac cgtaaaggaa   1440
ggtgaccacc ggaaagaagc tttcagtatt gggatgcaga gggacctcag cctttacctc   1500
cctgccatga agaagcagat ggccatactg gacgctttat aagaggtcca tgggctggaa   1560
tctgatgagg ttgtatgatg gctgctgggc agcacctcct aacttcaggg aataaagtgc   1620
taaagtgtaa aaaaaaataa aaataaaaat aaataaataa ataaaattaa aaaaaataaa   1680
aaaaaaaaaa aaaaaaaaaa a                                            1701

<210> SEQ ID NO 6
<211> LENGTH: 2004
<212> TYPE: DNA
<213> ORGANISM: Homo sapiens

<400> SEQUENCE: 6
aggcgatggc cctgctgctg gtgctcctcg cctcttgggg cctggggcag tgaggggcc      60 ggcgggcgtg ggccgagtgg ccgcgggcgc catggagggg gtgctgtaca agtggaccaa   120
ctatctgagc ggttggcagc ctcgatggtt ccttctctgt gggggaatat tgtcctatta   180
tgattctcct gaagatgcct ggaaaggttc aaaggagc atacaaatgg cagtctgtga   240
aattcaagtt cattctgtag ataatacacg catggacctg ataatccctg gggaacagta   300
tttctacctg aaggccagaa gtgtggctga agacagcgg tggctggtgg ccctgggatc   360
agccaaggct tgcctgactg acagtaggac ccagaaggag aaagagtttg ctgaaaacac   420
tgaaaacttg aaaaccaaaa tgtcagaact aagactctac tgtgacctcc ttgttcagca   480
agtagataaa acaaaagaag tgaccacaac tggtgtgtcc aattctgagg agggaattga   540
tgtgggaact tgctgaaaat caacctgtaa tactttctg aagacttgg aagaatgcat   600 gcagatcgca aatgcagcct tcacctctga gctgctctac cgcactccac caggatcacc   660
tcagctggcc atgctcaagt ccagcaagat gaaacatcct attataccaa ttcataattc   720
attggaaagg caaatggagt tgagcacttg tgaaaatgga tctttaaata tggaaataaa   780
tggtgaggaa gaaatcctaa tgaaaaataa gaattcctta tatttgaaat ctgcagagat   840
agactgcagc atatcaagtg aggaaaatac agatgataat ataacagtcc aaggtgaaat   900
aaggaaggaa gatggaatgg aaaacctgaa aaatcatgac aataacttga ctcagtctgg   960
atcagactca agttgctctc cggaatgcct ctggaggaa ggcaaagaag ttatcccaac   1020
tttctttagt accatgaaca caagctttag tgacattgaa cttctggaag acagtggcat   1080
tcccacagaa gcattcttgg catcatgtta tgctgtggtt ccagtattag acaaacttgg   1140
ccctacagtg tttgctcctg ttaagatgga tcttgttgga aatattaaga agtaaatca   1200 gaagtatata accaacaaag aagagtttac cactctccag aagatagtgc tgcacgaagt   1260
ggaggcggat gtagcccagg ttaggaactc agcgactgaa gccctcttgt ggctgaagag   1320
```

| | |
|---|---:|
| aggtctcaaa tttttgaagg gattttttgac agaagtgaaa aatggggaga aggatatcca | 1380 |
| gacagcccta agaaatccaa cagaaaacac ttgacaccaa acatacccct gatgaagatc | 1440 |
| ctgaacttca agaatgaaga aagaattcct caccattcag gcagaaaaag caagtcacca | 1500 |
| agggacctca aacttccttt ccacaagatt ctgtgacggg aaacaatggg ggagtatttc | 1560 |
| cgaagttctg agtaggaaaa aagaatgact caaatgtatt attgccaacc aagtcgtcaa | 1620 |
| atctaatgtc aagttctctt aagcaggtaa gaactcagaa cataatacct gagtgccttc | 1680 |
| ttaaggaaac catttgatag gaaagatgaa ccaaataact caatgatgga tgagctggta | 1740 |
| gaaaaaaagc tggtggtgaa ccaaggtcaa actggaaatt atagtcacag tatagatata | 1800 |
| gattataaat attacaaacc ctaagatagc taataaattg gaatgggag aagggaggat | 1860 |
| ataagagcac taatgccctc ttattttcat agcagagact tgatactgtc tcaactttt | 1920 |
| tcaaaaacac aatttcttaa attttttggt aatcttttaa ataaacagat ttctaaaaag | 1980 |
| aaaaaaaaaa aaaaaaaaaa aaaa | 2004 |

<210> SEQ ID NO 7
<211> LENGTH: 1928
<212> TYPE: DNA
<213> ORGANISM: Homo sapiens

<400> SEQUENCE: 7

| | |
|---|---:|
| gccgcctgcg accggcagct cgttcgccgc actttggagg cttcggctgc ccctccgacc | 60 |
| cacgtagggc ccggacccgg gcctccttgt gaacagcgtg ccggcttcgc cccacgggtt | 120 |
| caccggctgg ctgggcttca agcgccgagg ccgccgcagt gaccccgccc ccgggccgag | 180 |
| gatgtgaggg gggccgggcg tccccacacc gggcccgggc gccgggagtg ggcgtctggg | 240 |
| cagcgccagg cgatggccct gctgctggtg ctcctcgcct cttggggcct ggggcagtga | 300 |
| gggggccggc gggcgtgggc cgagtggccg cgggcgccat ggagggggtg ctgtacaagt | 360 |
| ggaccaacta tctgagcggt tggcagcctc gatggttcct tctctgtggg ggaatattgt | 420 |
| cctattatga ttctcctgaa gatgcctgga aaggttgcaa agggagcata caaatggcag | 480 |
| tctgtgaaat tcaagttcat tctgtagata atacacgcat ggacctgata atccctgggg | 540 |
| aacagtattt ctacctgaag gccagaagtg tggctgaaag acagcggtgg ctggtggccc | 600 |
| tgggatcagc caaggcttgc ctgactgaca gtaggaccca gaaggagaaa gagtttgctg | 660 |
| aaaacactga aacttgaaa accaaaatgt cagaactaag actctactgt gacctccttg | 720 |
| ttcagcaagt agataaaaca aaagaagtga ccacaactgg tgtgtccaat tctgaggagg | 780 |
| gaattgatgt gggaactttg ctgaaatcaa cctgtaatac ttttctgaag accttggaag | 840 |
| aatgcatgca gatcgcaaat gcagccttca cctctgagct gctctaccgc actccaccag | 900 |
| gatcacctca gctggccatg ctcaagtcca gcaagatgaa acatcctatt ataccaattc | 960 |
| ataattcatt ggaaaggcaa atggagttga gcacttgtga aaatggatct ttaaatatgg | 1020 |
| aaataaatgg tgaggaagaa atcctaatga aaaataagaa ttccttatat ttgaaatctg | 1080 |
| cagagataga ctgcagcata tcaagtgagg aaaatacaga tgataatata acagtccaag | 1140 |
| gtgaaataag gaaggaagat ggaatggaaa acctgaaaaa tcatgacaat aacttgactc | 1200 |
| agtctggatc agactcaagt tgctctccgg aatgcctctg ggaggaaggc aaagaagtta | 1260 |
| tcccaacttt ctttagtacc atgaacacaa gctttagtga cattgaactt ctggaagaca | 1320 |
| gtggcattcc cacagaagca ttcttggcat catgttatgc tgtggttcca gtattagaca | 1380 |
| aacttggccc tacagtgttt gctcctgtta agatggatct tgttggaaat attaagaaag | 1440 |

| | |
|---|---|
| taaatcagaa gtatataacc aacaaagaag agtttaccac tctccagaag atagtgctgc | 1500 |
| acgaagtgga ggcggatgta gcccaggtta ggaactcagc gactgaagcc ctcttgtggc | 1560 |
| tgaagagagg tctcaaattt ttgaagggat ttttgacaga agtgaaaaat ggggagaagg | 1620 |
| atatccagac agccctaaat aatgcatatg gtaaaacatt gcggcaacac catggctggg | 1680 |
| tagttcgagg ggttttttgcg gtgtaggaat gtgggtgtag acggaactcc agaaaccatc | 1740 |
| atggaccatg aggcaactct gaggatggaa gccacacact aaggacggta aagcagaaag | 1800 |
| aagagctgaa accctgatga taaagaagca gccaattccg tcctgcactg cccacctcca | 1860 |
| gatctcattc atgtgaaaca agagaaact ttatcttgtt caagtcaaaa aaaaaaaaaa | 1920 |
| aaaaaaaa | 1928 |

<210> SEQ ID NO 8
<211> LENGTH: 2836
<212> TYPE: DNA
<213> ORGANISM: Homo sapiens

<400> SEQUENCE: 8

| | |
|---|---|
| agctcgttcg ccgcactttg gaggcttcgg ctgcccctcc gacccacgta gggcccggac | 60 |
| ccgggcctcc ttgtgaacag cgtgccggct tcgccccacg ggttcaccgg ctggctgggc | 120 |
| ttcaagcgcc gaggccgccg cagtgacccc gcccccgggc cgaggatgtg aggcgggccg | 180 |
| ggcgtcccca caccgggccc gggcgccggg agtgggcgtc tgggcagcgc caggcgatgg | 240 |
| ccctgctgct ggtgctcctc gcctcttggg gcctggggca gtgaggggggc cggcgggcgt | 300 |
| gggccgagtg gccgcgggcg ccatggaggg ggtgctgtac aagtggacca actatctgag | 360 |
| cggttggcag cctcgatggt tccttctctg tggggaata ttgtcctatt atgattctcc | 420 |
| tgaagatgcc tggaaaggtt gcaaagggag catacaaatg gcagtctgtg aaattcaagt | 480 |
| tcattctgta gataatacac gcatggacct gataatccct ggggaacagt atttctacct | 540 |
| gaaggccaga agtgtggctg aaagacagcg gtggctggtg gccctgggat cagccaaggc | 600 |
| ttgcctgact gacagtagga cccagaagga gaaagagttt gctgaaaaca ctgaaaactt | 660 |
| gaaaaccaaa atgtcagaac taagactcta ctgtgacctc cttgttcagc aagtagataa | 720 |
| aacaaaagaa gtgaccacaa ctggtgtgtc caattctgag gagggaattg atgtgggaac | 780 |
| tttgctgaaa tcaacctgta atactttttct gaagaccttg gaagaatgca tgcagatcgc | 840 |
| aaatgcagcc ttcacctctg agctgctcta ccgcactcca ccaggatcac ctcagctggc | 900 |
| catgctcaag tccagcaaga tgaaacatcc tattatacca attcataatt cattggaaag | 960 |
| gcaaatggag ttgagcactt gtgaaaatgg atctttaaat atggaaataa atggtgggga | 1020 |
| agaaatccta atgaaaaata agaattcctt atatttgaaa tctgcagaga tagactgcag | 1080 |
| catatcaagt gaggaaaata cagatgataa tataacagtc caaggtgaaa taaggaagga | 1140 |
| agatggaatg gaaaacctga aaatcatga caataacttg actcagtctg gatcagactc | 1200 |
| aagttgctct ccggaatgcc tctgggagga aggcaaagaa gttatcccaa ctttctttag | 1260 |
| taccatgaac acaagcttta gtgacattga acttctggaa gacagtggca ttcccacaga | 1320 |
| agcattcttg gcatcatgtt atgctgtggt tccagtatta gacaaacttg gccctacagt | 1380 |
| gtttgctcct gttaagatgg atcttgttgg aaatattaag aaagtaaaca gaagtatata | 1440 |
| accaacaaag aagagtttac cactctccag aagatagtgc tgcacgaagt ggaggcggat | 1500 |
| gtagcccagg ttaggaactc agcgactgaa gccctcttgt ggctgaagag aggtctcaaa | 1560 |
| ttttgaagg gattttttgac agaagtgaaa atgggggaga aggatatcca gacagcccta | 1620 |

```
agtgtaggaa tgtgggtgta gacggaactc cagaaaccat catgaccat gaggcaactc    1680 tgaggatgga agccacacac taaggacggt aaagcagaaa gaagagctga aaccctgatg    1740
ataaagaagc agccaattcc gtcctgcact gcccacctcc agatctcatt catgtgaaac    1800
aaagagaaac tttatcttgt tcaagtcact ttagtcaaga tttttattat cagatgaatg    1860
caatttctaa ttgatacacc ttaaaatttt caacatgtac acctgattta acaaaatcta    1920
gaattaagtc aatacttcta catgcattat agaccaaagg tcactgctat aagaactttg    1980
ggtatatagt caaattcctc acattttag aaacttgttt attcattgca tccctcccc      2040 atctcactct ctcacacact cacatattta ttttctcaga tccttataag ttcataagac    2100
atatgtcctt attccatttt tacagatgag aaaactgggg tttgcagggg ttaagtaact    2160
tatccaagat cacacaatta attagtggcg aagtcataat ttgaagtctt tctaatgccc    2220
aaatgtttcc attgtgtcac atatcggagc tgtgctcttt ccatcagcca gtttcccatt    2280
atcatagctg atgacatgca cacccaccat ctggggcagg ctttagtaca gcactctgtg    2340
ccatcatcca gatcaccaaa tcttagtaaa tggacgtgtc ataagagata aggctgccat    2400
agaatcacag cagcttctgg cttagtaaat tacctggata cacacctttt cctagaggaa    2460
atcccacatc ttcgtaggag atctggtgta atgctcttgg gacctctctc tagaggatga    2520
gctagtatca ctgggtccta gtaagtttca gcaaatataa tagagacaga actgtcatca    2580
ttatcagaaa agaaacagag aaaaatgtta aacaatggt tttgtgacct taaagtctgt    2640
gttagtccct tagcaccacc gctgagattt tgctgaaagg gacgttttgt gtgttgggct    2700
tcactgaagg aagcccctga agtgttcag aaataggaa aatgagaaac tgttccagct     2760
gaaaatacgg gcaaggggga atcattgaag aagacagaat attgaagtgt tcaaatgaat    2820
aaagaagcta aaaact                                                   2836

<210> SEQ ID NO 9
<211> LENGTH: 1781
<212> TYPE: DNA
<213> ORGANISM: Homo sapiens

<400> SEQUENCE: 9
gctgctggtg ctcctcgcct cttggggcct ggggcagtga gggggccggc gggcgtgggc      60
cgagtggccg cgggcgccat ggaggggtg ctgtacaagt ggaccaacta tctgagcggt     120
tggcagcctc gatggttcct tctctgtggg ggaatattgt cctattatga ttctcctgaa     180
gatgcctgga aaggttgcaa agggagcata caaatggcag tctgtgaaat tcaagttcat     240
tctgtagata atacacgcat ggacctgata atccctgggg aacagtattt ctacctgaag     300
gccagaagtg tggctgaaag acagcggtgg ctggtggccc tgggatcagc caaggcttgc     360
ctgactgaca gtaggaccca gaaggagaaa gagtttgctg aaaacactga aaacttgaaa     420
accaaaatgt cagaactaag actctactgt gacctccttg ttcagcaagt agataaaaca     480
aaagaagtga ccacaactgg tgtgtccaat tctgaggagg gaattgatgt gggaactttg     540
ctgaaatcaa cctgtaatac ttttctgaag accttggaag aatgcatgca gatcgcaaat     600
gcagccttca cctctgagct gctctaccgc actccaccag gatcacctca gctggccatg     660
ctcaagtcca gcaagatgaa acatcctatt ataccaattc ataattcatt ggaaaggcaa     720
atggagttga gcacttgtga aaatggatct ttaaatatgg aaataaatgg tgaggaagaa     780
atcctaatga aaaataagaa ttccttatat ttgaaatctg cagagataga ctgcagcata     840
tcaagtgagg aaaaatacaga tgataatata acagtccaag gtgaaataag gaaggaagat     900
```

```
ggaatggaaa acctgaaaaa tcatgacaat aacttgactc agtctggatc agactcaagt    960
tgctctccgg aatgcctctg ggaggaaggc aaagaagtta tcccaacttt ctttagtacc   1020
atgaacacaa gctttagtga cattgaactt ctggaagaca gtggcattcc cacagaagca   1080
ttcttggcat catgttatgc tgtggttcca gtattagaca aacttggccc tacagtgttt   1140
gctcctgtta aagatggatc ttgttggaaa tattaagaaa gtaaatcaga agtatataac   1200
caacaaagaa gagtttacca ctctccagaa gatagtgctg cacgaagtgg aggcggatgt   1260
agcccaggtt aggaactcag cgactgaagc cctcttgtgg ctgaagagag gtctcaaatt   1320
tttgaaggga ttttgacag aagtgaaaaa tggggagaag gatatccaga cagccctaaa    1380
taatgcatat ggtaaaacat tgcggcaaca ccatggctgg gtagttcgag gggttttgc    1440 gttagcttta agggcagctc catcctatga agattttgtg gccgcgttaa ccgtaaagga   1500
aggtgaccac cagaaagaag ctttcagtat tgggatgcag agggacctca gcctttacct   1560
ccctgccatg gagaagcagc tggccatact ggacacttta tatgaggtcc acgggctgga   1620
atctgatgag gtggtatgat ggctgctggg cagcacctcc taacttcagg gaataagtgc   1680
taaagtgttt tgttgcccta cttaatttcc agcaacagcc tcaacccctct ccaaccccctt  1740 cacctggggg gatggacagg aggtggcaaa acccagtgct t                      1781

<210> SEQ ID NO 10
<211> LENGTH: 455
<212> TYPE: PRT
<213> ORGANISM: Homo sapiens

<400> SEQUENCE: 10

Met Glu Gly Val Leu Tyr Lys Trp Thr Asn Tyr Leu Ser Gly Trp Gln
1               5                   10                  15

Pro Arg Trp Phe Leu Leu Cys Gly Gly Ile Leu Ser Tyr Tyr Asp Ser
            20                  25                  30

Pro Glu Asp Ala Trp Lys Gly Cys Lys Gly Ser Ile Gln Met Ala Val
        35                  40                  45

Cys Glu Ile Gln Val His Ser Val Asp Asn Thr Arg Met Asp Leu Ile
    50                  55                  60

Ile Pro Gly Glu Gln Tyr Phe Tyr Leu Lys Ala Arg Ser Val Ala Glu
65                  70                  75                  80

Arg Gln Arg Trp Leu Val Ala Leu Gly Ser Ala Lys Ala Cys Leu Thr
                85                  90                  95

Asp Ser Arg Thr Gln Lys Glu Lys Glu Phe Ala Glu Asn Thr Glu Asn
            100                 105                 110

Leu Lys Thr Lys Met Ser Glu Leu Arg Leu Tyr Cys Asp Leu Leu Val
        115                 120                 125

Gln Gln Val Asp Lys Thr Lys Glu Val Thr Thr Thr Gly Val Ser Asn
    130                 135                 140

Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
                165                 170                 175

Phe Thr Ser Glu Leu Leu Tyr Arg Thr Pro Gly Ser Pro Gln Leu
            180                 185                 190

Ala Met Leu Lys Ser Ser Lys Met Lys His Pro Ile Ile Pro Ile His
        195                 200                 205

Asn Ser Leu Glu Arg Gln Met Glu Leu Ser Thr Cys Glu Asn Gly Ser
    210                 215                 220
```

```
Leu Asn Met Glu Ile Asn Gly Glu Glu Ile Leu Met Lys Asn Lys
225                 230                 235                 240

Asn Ser Leu Tyr Leu Lys Ser Ala Glu Ile Asp Cys Ser Ile Ser Ser
            245                 250                 255

Glu Glu Asn Thr Asp Asp Asn Ile Thr Val Gln Gly Glu Ile Arg Lys
            260                 265                 270

Glu Asp Gly Met Glu Asn Leu Lys Asn His Asp Asn Asn Leu Thr Gln
            275                 280                 285

Ser Gly Ser Asp Ser Ser Cys Ser Pro Glu Cys Leu Trp Glu Glu Gly
            290                 295                 300

Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
            325                 330                 335

Ala Ser Cys Tyr Ala Val Val Pro Val Leu Asp Lys Leu Gly Pro Thr
            340                 345                 350

Val Phe Ala Pro Val Lys Met Asp Leu Val Gly Asn Ile Lys Lys Val
            355                 360                 365

Asn Gln Lys Tyr Ile Thr Asn Lys Glu Glu Phe Thr Thr Leu Gln Lys
            370                 375                 380

Ile Val Leu His Glu Val Glu Ala Asp Val Ala Gln Val Arg Asn Ser
385                 390                 395                 400

Ala Thr Glu Ala Leu Leu Trp Leu Lys Arg Gly Leu Lys Phe Leu Lys
            405                 410                 415

Gly Phe Leu Thr Glu Val Lys Asn Gly Glu Lys Asp Ile Gln Thr Ala
            420                 425                 430

Leu Asn Asn Ala Tyr Gly Lys Thr Leu Arg Gln His His Gly Trp Val
            435                 440                 445

Val Arg Gly Val Phe Ala Val
450                 455

<210> SEQ ID NO 11
<211> LENGTH: 507
<212> TYPE: PRT
<213> ORGANISM: Homo sapiens

<400> SEQUENCE: 11

Met Glu Gly Val Leu Tyr Lys Trp Thr Asn Tyr Leu Ser Gly Trp Gln
1               5                   10                  15

Pro Arg Trp Phe Leu Leu Cys Gly Gly Ile Leu Ser Tyr Tyr Asp Ser
            20                  25                  30

Pro Glu Asp Ala Trp Lys Gly Cys Lys Gly Ser Ile Gln Met Ala Val
            35                  40                  45

Cys Glu Ile Gln Val His Ser Val Asp Asn Thr Arg Met Asp Leu Ile
    50                  55                  60

Ile Pro Gly Glu Gln Tyr Phe Tyr Leu Lys Ala Arg Ser Val Ala Glu
65                  70                  75                  80

Arg Gln Arg Trp Leu Val Ala Leu Gly Ser Ala Lys Ala Cys Leu Thr
                85                  90                  95

Asp Ser Arg Thr Gln Lys Glu Lys Glu Phe Ala Glu Asn Thr Glu Asn
            100                 105                 110

Leu Lys Thr Lys Met Ser Glu Leu Arg Leu Tyr Cys Asp Leu Leu Val
        115                 120                 125

Gln Gln Val Asp Lys Thr Lys Glu Val Thr Thr Thr Gly Val Ser Asn
130                 135                 140
```

```
Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
            165                 170                 175

Phe Thr Ser Glu Leu Leu Tyr Arg Thr Pro Gly Ser Pro Gln Leu
        180                 185                 190

Ala Met Leu Lys Ser Ser Lys Met Lys His Pro Ile Ile Pro Ile His
    195                 200                 205

Asn Ser Leu Glu Arg Gln Met Glu Leu Ser Thr Cys Glu Asn Gly Ser
210                 215                 220

Leu Asn Met Glu Ile Asn Gly Glu Glu Ile Leu Met Lys Asn Lys
225                 230                 235                 240

Asn Ser Leu Tyr Leu Lys Ser Ala Glu Ile Asp Cys Ser Ile Ser Ser
                245                 250                 255

Glu Glu Asn Thr Asp Asp Asn Ile Thr Val Gln Gly Glu Ile Arg Lys
                260                 265                 270

Glu Asp Gly Met Glu Asn Leu Lys Asn His Asp Asn Asn Leu Ser Gln
            275                 280                 285

Ser Gly Ser Asp Ser Ser Cys Ser Pro Glu Cys Leu Trp Glu Glu Gly
        290                 295                 300

Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
                325                 330                 335

Ala Ser Cys Cys Ala Val Val Pro Val Leu Asp Lys Leu Gly Pro Thr
                340                 345                 350

Val Phe Ala Pro Val Lys Met Asp Leu Val Glu Asn Ile Lys Lys Val
            355                 360                 365

Asn Gln Lys Tyr Ile Thr Asn Lys Glu Glu Phe Thr Thr Leu Gln Lys
        370                 375                 380

Ile Val Leu His Glu Val Glu Ala Asp Val Ala Gln Val Arg Asn Ser
385                 390                 395                 400

Ala Thr Glu Ala Leu Leu Trp Leu Lys Arg Gly Leu Lys Phe Leu Lys
                405                 410                 415

Gly Phe Leu Thr Glu Val Lys Asn Gly Glu Lys Asp Ile Gln Thr Ala
                420                 425                 430

Leu Asn Asn Ala Tyr Gly Lys Thr Leu Arg Gln His His Gly Trp Val
            435                 440                 445

Val Arg Gly Val Phe Ala Leu Ala Leu Arg Ala Thr Pro Ser Tyr Glu
    450                 455                 460

Asp Phe Val Ala Ala Leu Thr Val Lys Glu Gly Asp His Arg Lys Glu
465                 470                 475                 480

Ala Phe Ser Ile Gly Met Gln Arg Asp Leu Ser Leu Tyr Leu Pro Ala
                485                 490                 495

Met Lys Lys Gln Met Ala Ile Leu Asp Ala Leu
            500                 505

<210> SEQ ID NO 12
<211> LENGTH: 440
<212> TYPE: PRT
<213> ORGANISM: Homo sapiens

<400> SEQUENCE: 12

Met Glu Gly Val Leu Tyr Lys Trp Thr Asn Tyr Leu Ser Gly Trp Gln
1               5                   10                  15
```

```
Pro Arg Trp Phe Leu Leu Cys Gly Gly Ile Leu Ser Tyr Tyr Asp Ser
             20                  25                  30

Pro Glu Asp Ala Trp Lys Gly Cys Lys Gly Ser Ile Gln Met Ala Val
             35                  40                  45

Cys Glu Ile Gln Val His Ser Val Asp Asn Thr Arg Met Asp Leu Ile
 50                  55                  60

Ile Pro Gly Glu Gln Tyr Phe Tyr Leu Lys Ala Arg Ser Val Ala Glu
 65                  70                  75                  80

Arg Gln Arg Trp Leu Val Ala Leu Gly Ser Ala Lys Ala Cys Leu Thr
                 85                  90                  95

Asp Ser Arg Thr Gln Lys Glu Lys Glu Phe Ala Glu Asn Thr Glu Asn
                100                 105                 110

Leu Lys Thr Lys Met Ser Glu Leu Arg Leu Tyr Cys Asp Leu Leu Val
             115                 120                 125

Gln Gln Val Asp Lys Thr Lys Glu Val Thr Thr Thr Gly Val Ser Asn
130                 135                 140

Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
                165                 170                 175

Phe Thr Ser Glu Leu Leu Tyr Arg Thr Pro Gly Ser Pro Gln Leu
                180                 185                 190

Ala Met Leu Lys Ser Ser Lys Met Lys His Pro Ile Ile Pro Ile His
                195                 200                 205

Asn Ser Leu Glu Arg Gln Met Glu Leu Ser Thr Cys Glu Asn Gly Ser
210                 215                 220

Leu Asn Met Glu Ile Asn Gly Glu Glu Ile Leu Met Lys Asn Lys
225                 230                 235                 240

Asn Ser Leu Tyr Leu Lys Ser Ala Glu Ile Asp Cys Ser Ile Ser Ser
                245                 250                 255

Glu Glu Asn Thr Asp Asp Asn Ile Thr Val Gln Gly Glu Ile Arg Lys
                260                 265                 270

Glu Asp Gly Met Glu Asn Leu Lys Asn His Asp Asn Leu Thr Gln
                275                 280                 285

Ser Gly Ser Asp Ser Ser Cys Ser Pro Glu Cys Leu Trp Glu Glu Gly
290                 295                 300

Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
                325                 330                 335

Ala Ser Cys Tyr Ala Val Val Pro Val Leu Asp Lys Leu Gly Pro Thr
                340                 345                 350

Val Phe Ala Pro Val Lys Met Asp Leu Val Gly Asn Ile Lys Lys Val
                355                 360                 365

Asn Gln Lys Tyr Ile Thr Asn Lys Glu Glu Phe Thr Thr Leu Gln Lys
                370                 375                 380

Ile Val Leu His Glu Val Glu Ala Asp Val Ala Gln Val Arg Asn Ser
385                 390                 395                 400

Ala Thr Glu Ala Leu Leu Trp Leu Lys Arg Gly Leu Lys Phe Leu Lys
                405                 410                 415

Gly Phe Leu Thr Glu Val Lys Asn Gly Glu Lys Asp Ile Gln Thr Ala
                420                 425                 430

Leu Arg Asn Pro Thr Glu Asn Thr
```

```
              435                 440
```

<210> SEQ ID NO 13
<211> LENGTH: 455
<212> TYPE: PRT
<213> ORGANISM: Homo sapiens

<400> SEQUENCE: 13

```
Met Glu Gly Val Leu Tyr Lys Trp Thr Asn Tyr Leu Ser Gly Trp Gln
1               5                   10                  15

Pro Arg Trp Phe Leu Leu Cys Gly Gly Ile Leu Ser Tyr Tyr Asp Ser
            20                  25                  30

Pro Glu Asp Ala Trp Lys Gly Cys Lys Gly Ser Ile Gln Met Ala Val
        35                  40                  45

Cys Glu Ile Gln Val His Ser Val Asp Asn Thr Arg Met Asp Leu Ile
    50                  55                  60

Ile Pro Gly Glu Gln Tyr Phe Tyr Leu Lys Ala Arg Ser Val Ala Glu
65                  70                  75                  80

Arg Gln Arg Trp Leu Val Ala Leu Gly Ser Ala Lys Ala Cys Leu Thr
                85                  90                  95

Asp Ser Arg Thr Gln Lys Glu Lys Glu Phe Ala Glu Asn Thr Glu Asn
            100                 105                 110

Leu Lys Thr Lys Met Ser Glu Leu Arg Leu Tyr Cys Asp Leu Leu Val
        115                 120                 125

Gln Gln Val Asp Lys Thr Lys Glu Val Thr Thr Gly Val Ser Asn
    130                 135                 140

Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
                165                 170                 175

Phe Thr Ser Glu Leu Leu Tyr Arg Thr Pro Pro Gly Ser Pro Gln Leu
            180                 185                 190

Ala Met Leu Lys Ser Ser Lys Met Lys His Pro Ile Ile Pro Ile His
        195                 200                 205

Asn Ser Leu Glu Arg Gln Met Glu Leu Ser Thr Cys Glu Asn Gly Ser
    210                 215                 220

Leu Asn Met Glu Ile Asn Gly Glu Glu Ile Leu Met Lys Asn Lys
225                 230                 235                 240

Asn Ser Leu Tyr Leu Lys Ser Ala Glu Ile Asp Cys Ser Ile Ser Ser
                245                 250                 255

Glu Glu Asn Thr Asp Asp Asn Ile Thr Val Gln Gly Glu Ile Arg Lys
            260                 265                 270

Glu Asp Gly Met Glu Asn Leu Lys Asn His Asp Asn Asn Leu Thr Gln
        275                 280                 285

Ser Gly Ser Asp Ser Ser Cys Ser Pro Glu Cys Leu Trp Glu Glu Gly
    290                 295                 300

Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
                325                 330                 335

Ala Ser Cys Tyr Ala Val Val Pro Val Leu Asp Lys Leu Gly Pro Thr
            340                 345                 350

Val Phe Ala Pro Val Lys Met Asp Leu Val Gly Asn Ile Lys Lys Val
        355                 360                 365

Asn Gln Lys Tyr Ile Thr Asn Lys Glu Glu Phe Thr Thr Leu Gln Lys
```

```
              370                 375                 380
Ile Val Leu His Glu Val Glu Ala Asp Val Ala Gln Val Arg Asn Ser
385                 390                 395                 400

Ala Thr Glu Ala Leu Leu Trp Leu Lys Arg Gly Leu Lys Phe Leu Lys
                405                 410                 415

Gly Phe Leu Thr Glu Val Lys Asn Gly Glu Lys Asp Ile Gln Thr Ala
                420                 425                 430

Leu Asn Asn Ala Tyr Gly Lys Thr Leu Arg Gln His His Gly Trp Val
                435                 440                 445

Val Arg Gly Val Phe Ala Val
                450                 455

<210> SEQ ID NO 14
<211> LENGTH: 372
<212> TYPE: PRT
<213> ORGANISM: Homo sapiens

<400> SEQUENCE: 14

Met Glu Gly Val Leu Tyr Lys Trp Thr Asn Tyr Leu Ser Gly Trp Gln
1               5                   10                  15

Pro Arg Trp Phe Leu Leu Cys Gly Gly Ile Leu Ser Tyr Tyr Asp Ser
                20                  25                  30

Pro Glu Asp Ala Trp Lys Gly Cys Lys Gly Ser Ile Gln Met Ala Val
                35                  40                  45

Cys Glu Ile Gln Val His Ser Val Asp Asn Thr Arg Met Asp Leu Ile
50                  55                  60

Ile Pro Gly Glu Gln Tyr Phe Tyr Leu Lys Ala Arg Ser Val Ala Glu
65                  70                  75                  80

Arg Gln Arg Trp Leu Val Ala Leu Gly Ser Ala Lys Ala Cys Leu Thr
                85                  90                  95

Asp Ser Arg Thr Gln Lys Glu Lys Glu Phe Ala Glu Asn Thr Glu Asn
                100                 105                 110

Leu Lys Thr Lys Met Ser Glu Leu Arg Leu Tyr Cys Asp Leu Leu Val
                115                 120                 125

Gln Gln Val Asp Lys Thr Lys Glu Val Thr Thr Thr Gly Val Ser Asn
130                 135                 140

Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
                165                 170                 175

Phe Thr Ser Glu Leu Leu Tyr Arg Thr Pro Gly Ser Pro Gln Leu
                180                 185                 190

Ala Met Leu Lys Ser Ser Lys Met Lys His Pro Ile Ile Pro Ile His
                195                 200                 205

Asn Ser Leu Glu Arg Gln Met Glu Leu Ser Thr Cys Glu Asn Gly Ser
210                 215                 220

Leu Asn Met Glu Ile Asn Gly Gly Glu Ile Leu Met Lys Asn Lys
225                 230                 235                 240

Asn Ser Leu Tyr Leu Lys Ser Ala Glu Ile Asp Cys Ser Ile Ser Ser
                245                 250                 255

Glu Glu Asn Thr Asp Asp Asn Ile Thr Val Gln Gly Glu Ile Arg Lys
                260                 265                 270

Glu Asp Gly Met Glu Asn Leu Lys Asn His Asp Asn Asn Leu Thr Gln
                275                 280                 285

Ser Gly Ser Asp Ser Ser Cys Ser Pro Glu Cys Leu Trp Glu Glu Gly
```

```
                290                 295                 300
Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
                325                 330                 335

Ala Ser Cys Tyr Ala Val Val Pro Val Leu Asp Lys Leu Gly Pro Thr
                340                 345                 350

Val Phe Ala Pro Val Lys Met Asp Leu Val Gly Asn Ile Lys Lys Val
                355                 360                 365

Asn Arg Ser Ile
            370

<210> SEQ ID NO 15
<211> LENGTH: 391
<212> TYPE: PRT
<213> ORGANISM: Homo sapiens

<400> SEQUENCE: 15

Ala Ala Gly Ala Pro Arg Leu Leu Gly Pro Gly Ala Val Arg Gly Pro
1               5                   10                  15

Ala Gly Val Gly Arg Val Ala Ala Gly Ala Met Glu Gly Val Leu Tyr
                20                  25                  30

Lys Trp Thr Asn Tyr Leu Ser Gly Trp Gln Pro Arg Trp Phe Leu Leu
            35                  40                  45

Cys Gly Gly Ile Leu Ser Tyr Tyr Asp Ser Pro Glu Asp Ala Trp Lys
        50                  55                  60

Gly Cys Lys Gly Ser Ile Gln Met Ala Val Cys Glu Ile Gln Val His
65                  70                  75                  80

Ser Val Asp Asn Thr Arg Met Asp Leu Ile Ile Pro Gly Glu Gln Tyr
                85                  90                  95

Phe Tyr Leu Lys Ala Arg Ser Val Ala Glu Arg Gln Arg Trp Leu Val
                100                 105                 110

Ala Leu Gly Ser Ala Lys Ala Cys Leu Thr Asp Ser Arg Thr Gln Lys
            115                 120                 125

Glu Lys Glu Phe Ala Glu Asn Thr Glu Asn Leu Lys Thr Lys Met Ser
130                 135                 140

Glu Leu Arg Leu Tyr Cys Asp Leu Leu Val Gln Gln Val Asp Lys Thr
145                 150                 155                 160

Lys Glu Val Thr Thr Thr Gly Val Ser Asn Ser Glu Glu Gly Ile Asp
                165                 170                 175

Val Gly Thr Leu Leu Lys Ser Thr Cys Asn Thr Phe Leu Lys Thr Leu
                180                 185                 190

Glu Glu Cys Met Gln Ile Ala Asn Ala Ala Phe Thr Ser Glu Leu Leu
            195                 200                 205

Tyr Arg Thr Pro Pro Gly Ser Pro Gln Leu Ala Met Leu Lys Ser Ser
210                 215                 220

Lys Met Lys His Pro Ile Ile Pro Ile His Asn Ser Leu Glu Arg Gln
225                 230                 235                 240

Met Glu Leu Ser Thr Cys Glu Asn Gly Ser Leu Asn Met Glu Ile Asn
                245                 250                 255

Gly Glu Glu Ile Leu Met Lys Asn Lys Asn Ser Leu Tyr Leu Lys
                260                 265                 270

Ser Ala Glu Ile Asp Cys Ser Ile Ser Ser Glu Glu Asn Thr Asp Asp
            275                 280                 285

Asn Ile Thr Val Gln Gly Glu Ile Arg Lys Glu Asp Gly Met Glu Asn
```

```
                290                 295                 300
Leu Lys Asn His Asp Asn Asn Leu Thr Gln Ser Gly Ser Asp Ser Ser
305                 310                 315                 320

Cys Ser Pro Glu Cys Leu Trp Glu Glu Gly Lys Glu Val Ile Pro Thr
                325                 330                 335

Phe Phe Ser Thr Met Asn Thr Ser Phe Ser Asp Ile Glu Leu Leu Glu
                340                 345                 350

Asp Ser Gly Ile Pro Thr Glu Ala Phe Leu Ala Ser Cys Tyr Ala Val
                355                 360                 365

Val Pro Val Leu Asp Lys Leu Gly Pro Thr Val Phe Ala Pro Val Lys
                370                 375                 380

Asp Gly Ser Cys Trp Lys Tyr
385                 390

<210> SEQ ID NO 16
<211> LENGTH: 3674
<212> TYPE: DNA
<213> ORGANISM: Homo sapiens

<400> SEQUENCE: 16
gggcctactc tgccgccgcc gccgcccgcc cgctccagcc gccgccgccg ccgccaccgc      60
cctccaggct ccgggacccg gccgcgccca ccgcccccgt gcgcgccccg ccgccgccgc     120
cttcgccttc gccttttgtt tcctccgctc cggcgccccc gccccggctc gcgctttgca     180
ggggacgcag cgcgcgcccc cagcgggccc gggaaaagcc gcggcgcgcg cgcgcgcctg     240
cgcggcggac ccctccttct cctccccgcg tgcgcgtgcc cttcttggct gcgcgccggc     300
gccgcctggc gggcgggagg ggaggtggca ggcgcgtttg caggaggggc gcacctcttc     360
gctcgcgcac ccccccggaa ggtagaccgg aaggggagg cgggcgggcg gagaggagag      420
agtggcgcgc agtccagcga gggcggggt tggctatgtg ggggtggtg caccccgcag       480 tctagacagt ctgatccggg ctgggggcgt gtacactcgg cgcacctgcg agactacaga     540
gcctcgggcc ggcacgtgtg gggagtgtgg acacgtctgc tgcgccccgc ttctcgctgc     600
tgaggggaag ggaggggggcg ggcaggtgca gcggccgggc tagtgggagg gggcggcggc    660
catggagcgg gtgaacgacg cttcgtgcgg cccgtctggc tgctacacat accaggtgag     720
cagacacagc acggagatgc tgcacaacct gaaccagcag cgcaaaaacg gcgggcgctt     780
ctgcgacgtg ctcttgcggg taggcgacga gagcttccca gcgcaccgcg ccgtgctggc    840
cgcctgcagc gagtactttg agtcggtgtt cagcgcccag ttgggcgacg gcggagctgc     900
ggacgggggt ccggctgatg tagggggcgc gacggcagca ccaggcggcg gggccggggg    960
cagccgggag ctggagatgc acactatcag ctccaaggta tttggggaca ttctggactt   1020
cgcctacact tcccgcatcg tggtgcgctt ggagagcttt cccgaactca tgacggccgc    1080
caagttcctg ctgatgaggt cggttatcga gatctgccag gaagtcatca aacagtccaa    1140
cgtacagatc ctggtacccc ctgcccgcgc cgatataatg ctctttcgcc ccctgggac    1200 ctcggacttg gcttcccctt tggacatgac caacggggca gccttggcag ccaacagcaa    1260
tggcatcgcc ggcagcatgc agccagagga ggaggcagct cgggcggctg gtgcagccat    1320
tgcaggccaa gcctctttgc ctgtgttacc tggggtggac cgcttgccca tggtggctgg    1380
accccctatc ccccaactgc tgacttcccc attccccagt gtggcatcca gtgcccctcc    1440
cctgactggc aagcgaggcc ggggccgccc aaggaaggcc aacctgctgg actcaatgtt    1500
tgggtcccca ggggcctga gggaggcagg catccttcca tgcggtctat gtggtaaggt    1560
```

```
gttcactgat gccaaccggc tccggcagca cgaggcccag cacggtgtca ccagcctcca    1620
gctgggctac atcgaccttc ctcctccgag gctgggtgag aatgggctac ccatctctga    1680
agaccccgac ggcccccgaa agaggagccg gaccaggaag caggtggctt gtgagatctg    1740
cggcaagatc ttccgtgatg tgtatcatct taaccggcac aagctgtccc actctgggga    1800
gaagccctac tcctgccctg tgtgtgggtt gcggttcaag agaaaagacc gcatgtccta    1860
ccatgtgcgg tcccatgatg ggtccgtggg caagccttac atctgccaga gctgtgggaa    1920
aggcttctcc aggcctgatc acttgaacgg acatatcaag caggtgcaca cttctgagcg    1980
gcctcacaag tgtcagacct gcaatgcttc ttttgccacc cgagaccgtc tgcgctccca    2040
cctggcctgt catgaagaca aggtgccctg ccaggtgtgt gggaagtact gcgggcagc    2100 atacatggca gaccacctga agaagcacag cgaggggccc agcaacttct gcagtatctg    2160
taaccgagaa ggccagaaat gctcacatca ggatccgatt gagagctctg actcctatgg    2220
tgacctctca gatgccagcg acctgaagac gccagagaag cagagtgcca atggctcttt    2280
ctcctgcgac atggcagtcc ccaaaaacaa aatggagtct gatggggaga agaagtaccc    2340
atgccctgaa tgtgggagct tcttccgctc taagtcctac ttgaacaaac acatccagaa    2400
ggtgcatgtc cgggctctcg ggggcccccct gggggacctg gccctgccc ttggctcacc    2460 tttctctcct cagcagaaca tgtctctcct cgagtccttt gggtttcaga ttgttcagtc    2520
ggcatttgcg tcatctttag tagatcctga ggttgaccag cagcccatgg ggcctgaagg    2580
gaaatgaggc agctgctgtg tccccacgga acaaccatc tggggactgc tgggaaatgc    2640
tgtgaatgcg gagggaagtg atgtttgggt tctgtagctg agagattttt attcatttt    2700 aactgccccc caaccccact ccaactcctt ctccaccacc cattctccca atggtcttta    2760
gaaatagatt ttcatctgat attctgcaga aatatcaatg agacttggta tgggacaggg    2820
gcagaaaaca ctacataggc ctccaaggca aaaccagtcc cagtttcttt aatgggaaga    2880
agctggaatt cctggtgctc aattcttagt gaccccaatc ctatacccaa atctatgata    2940
ttctgggacc tcagtgattt tggtcccctc ccacttctct agttcgtcat cctcccttcc    3000
catatccttc aaaagaacca cactagggtc tccacctact tatacaatgc ggatgcccaa    3060
ctgtttttaa ggaagccaga agcatcccat ggaccatggg gtgagtgtcc tccaagagcc    3120
ccctgagctc agccctctgc ctggagggct ccagacctttc tgagccctg cttggaggcg    3180 agcattttca ctgctaggac aagctcagct gttgaggaca cccccacccc aaatttcagt    3240
tcttacgtga ttttaaccat tcaacatgct gttgggtttt aattctctaa ttattattat    3300
tattgttatt attttttagg accagttgta gtgaattgct actgaaagct atcccaggtg    3360
atacagagct ctttgtaaac cgcagtcaca cattagggtt agtattaaac tttgtttaga    3420
tgtaccataa ttaacttggc tagttgattg tttgaagtct atggaagaaa tagttttatg    3480
caaaatttta aaaatgcca gtctggtcag ggaagtaggg ggtttcaatg ctgttgggaa    3540
ccaggaaggt gggacagccg gcaggtaggg acattgtgta cctcagttgt gtcacatgtg    3600
agcaagccca ggttgacctt gtgatgtgaa ttgatctgat cagactgtat taaaaatgtt    3660
agtacattac tcta                                                     3674
```

<210> SEQ ID NO 17
<211> LENGTH: 3674
<212> TYPE: RNA
<213> ORGANISM: Homo sapiens

<400> SEQUENCE: 17

```
gggccuacuc ugccgccgcc gccgcccgcc cgcuccagcc gccgccgccg ccgccaccgc    60
ccuccaggcu ccgggacccg gcccgcgcca ccgcccccgu gcgcgcccg ccgccgccgc    120 cuucgccuuc gccuuuuguu uccuccgcuc cggcgccccc gccccggcuc gcgcuuugca    180
ggggacgcag cgcgcgcccc cagcgggccc gggaaaagcc gcggcgcgcg cgcgcgccug    240
cgcggcggac cccuccuucu ccuccccgcg ugcgcgugcc cuucuuggcu gcgcgccggc    300
gccgccuggc gggcgggagg ggagguggca ggcgcguuug caggaggggc gcaccucuuc    360
gcucgcgcac ccccccggaa gguagaccgg aaggggagg cgggcgggcg gagaggagag    420
aguggcgcgc aguccagcga gggcggggu uggcuaugug gggggugug cacccccgcag   480 ucuagacagu cugauccggg cuggggggcgu guacacucgg cgcaccugcg agacuacaga   540
gccucgggcc ggcacgugug gggagugugg acacgucugc ugcgcccgc uucucgcugc    600 ugaggggaag ggagggggcg ggcaggugca gcggccgggc uaguggagg gggcggcggc    660 cauggagcgg gugaacgacg cuucgugcgg cccgucuggc ugcuacacau accaggugag    720
cagacacagc acggagaugc ugcacaaccu gaaccagcag cgcaaaaacg gcgggcgcuu    780
cugcgacgug ucuuugcggg uaggcgacga gagcuuccca gcgcaccgcg ccgugcuggc    840
cgccugcagc gaguacuuug agucggguguu cagcgcccag uugggcgacg gcggagcugc    900 ggacggggu ccggcugaug uaggggcgc gacggcagca ccaggcggcg gggccggggg    960
cagccgggag cuggagaugc acacuaucag cuccaaggua uuuggggaca uucuggacuu   1020
cgccuacacu ucccgcaucg uggugcgcuu ggagagcuuu cccgaacuca ugacggccgc   1080
caaguuccug cugaugaggu cgguuaucga gaucugccag gaagucauca aacaguccaa   1140
cguacagauc cugguacccc cugcccgcgc cgauauaaug ucuuucgcc ccccugggac    1200 cucggacuug ggcuucccuu uggacaugac caacggggca gccuuggcag ccaacagcaa   1260
uggcaucgcc ggcagcaugc agccaggaga ggaggcagcu cgggcggcug ugcagccau    1320 ugcaggccaa gccucuuugc cuguguuacc uggggugggac cgcuugccca uggugcugg    1380 accccuaucc ccccaacugc ugacuucccc auucccccagu guggcaucca ugccccuucc   1440
ccugacuggc aagcgaggcc ggggccgccc aaggaaggcc aaccugcugg acucaaguguu   1500 ugggucccca ggggccugga ggaggcagg cauccuucca ugcggucuau gugguaaggu    1560
guucacugau gccaaccggc uccggcagca cgaggcccag cacgugucag ccagccucca   1620
gcugggcuac aucgaccuuc cuccuccgag gcugggugag auggcuac ccaucucuga    1680 agaccccgac ggccccgaaa agaggagccg gaccaggaag cagguggcuu gugagaaucug   1740 cggcaagauc uuccgugaug uguaucaucu uaaccggcac aagcugucc acucugggga   1800 gaagcccuac uccugcccug uguggggguu gcgguucaag agaaaagacc gcaugccua    1860 ccaugugcgg ucccaugaug ggccguggg caagccuauc aucaccagga gcugugggaa   1920
aggcuucucc aggccugauc acuugaacgg acauaucaag caggugcaca cuucugagcg    1980 gcccucacaag ugcagaccuu gcaaugcuuc uuuugccacc cgagaccguc ugcgcuccca   2040
ccuggccugu caugaagaca gguugcccug ccaggugugu ggaaguacuu gcgggcagc    2100 auacauggca gaccaccuga gaagcacag cgaggggccc agcaacuucu gcaguaucug   2160
uaaccgagaa ggcagaaaau gcucacauca ggaccgauu gagagcucug accucuaugg   2220
ugaccucuca gaugccagcg accugaagac gccagagaag cagagugcca auggcucuuu    2280
cuccugcgac auggcaguccc ccaaaaacaa aauggagucu gauggggaga gaaguaccc    2340 augcccugaa uguggggagcu ucuuccgcuc uaaguccuac uugaacaaac acauccagaa    2400
```

| | | | | |
|---|---|---|---|---|
| ggugcauguc | cgggcucucg | ggggccccu | ggggaccug | ggcccugccc | uuggcucacc | 2460 |
| uuucucuccu | cagcagaaca | ugucucuccu | cgagcccuuu | ggguuucaga | uguucaguc | 2520 |
| ggcauuugcg | ucaucuuuag | uagauccuga | gguugaccag | cagcccaugg | ggccugaagg | 2580 |
| gaaaugaggc | agcugcugug | uccccacgga | aacaaccauc | uggggacugc | ugggaaaugc | 2640 |
| ugugaaugcg | gagggaagug | auguuugggu | ucuagcug | agagauuuuu | auucauuuuu | 2700 |
| aacugccccc | caaccccacu | ccaacuccuu | cuccaccacc | cauucuccca | uggucuuua | 2760 |
| gaaauagauu | uucaucugau | auucugcaga | aauaucaaug | agacuuggua | ugggacaggg | 2820 |
| gcagaaaaca | cuacauaggc | cuccaaggca | aaccaguccc | caguuucuuu | aaugggaaga | 2880 |
| agcuggaauu | ccuggugcuc | aauucuuagu | gaccccaauc | cuauacccaa | aucuaugaua | 2940 |
| uucugggacc | ucagugauuu | uggcccccuc | ccacuucucu | aguucgucau | ccucccuucc | 3000 |
| cauauccuuc | aaaagaacca | cacuaggguc | uccaccuacu | uauacaaugc | ggaugcccaa | 3060 |
| cuguuuuuaa | ggaagccaga | agcaucccau | ggaccauggg | gugagugucc | uccaagagcc | 3120 |
| cccugagcuc | agcccucugc | cuggagggcu | ccagaccuuu | cugagcccug | cuuggaggcg | 3180 |
| agcauuuuca | cugcuaggac | aagcucagcu | guugaggaca | cccccacccc | aaauuucagu | 3240 |
| ucuuacguga | uuuuaaccau | ucaacaugcu | guuggguuuu | aauucucuaa | uuauuauuau | 3300 |
| uauuguuauu | auuuuuuagg | accaguugua | gugaauugcu | acugaaagcu | aucccaggug | 3360 |
| auacagagcu | cuuuguaaac | cgcagucaca | cauuaggguu | aguauuaaac | uuuguuuaga | 3420 |
| uguaccauaa | uuaacuuggc | uaguugauug | uuugaagucu | auggaagaaa | uaguuuuaug | 3480 |
| caaaauuuua | aaaaugcca | gucuggucag | ggaaguaggg | gguuucaaug | cuguugggaa | 3540 |
| ccaggaaggu | gggacagccg | gcagguaggg | acauugugua | ccucaguugu | gucacaugug | 3600 |
| agcaagccca | gguugaccuu | gugaugugaa | uugaucugau | cagacuguau | uaaaaauguu | 3660 |
| aguacauuac | ucua | | | | | 3674 |

<210> SEQ ID NO 18
<211> LENGTH: 3812
<212> TYPE: DNA
<213> ORGANISM: Homo sapiens

<400> SEQUENCE: 18

| | | | | |
|---|---|---|---|---|
| gggcctactc | tgccgccgcc | gccgccgcc | cgctccagcc | gccgccgccg | ccgccaccgc | 60 |
| cctccaggct | ccgggacccg | gcccgcgcca | ccgcccccgt | gcgcgccccg | ccgccgccgc | 120 |
| cttcgccttc | gcctttttgtt | tcctccgctc | cggcgccccc | gccccggctc | gcgctttgca | 180 |
| ggggacgcag | cgcgcgcccc | cagcgggccc | gggaaaagcc | gcggcgcgcg | cgcgcgcctg | 240 |
| cgcggcggac | ccctccttct | cctccccgcg | tgcgcgtgcc | cttcttggct | gcgcgccggc | 300 |
| gccgcctggc | gggcgggagg | ggaggtggca | ggcgcgtttg | caggaggggc | gcacctcttc | 360 |
| gctcgcgcac | ccccccggaa | ggtagaccgg | gaaggggagg | cgggcggggcg | gagaggagag | 420 |
| agtggcgcgc | agtccagcga | gggcgggggt | tggctatgtg | ggggtggtg | caccccgcag | 480 |
| tctagacagt | ctgatccggg | ctgggggcgt | gtacactcgg | cgcacctgcg | agactacaga | 540 |
| gcctcgggcc | ggcacgtgtg | gggagtgtgg | acacgtctgc | tgcgccccgc | ttctcgctgc | 600 |
| tgaggggaag | ggaggggcg | ggcaggtgca | cggccgggc | tagtgggagg | gggcggcggc | 660 |
| catggagcgg | gtgaacgacg | cttcgtgcgg | cccgtctggc | tgctacacat | accaggtgag | 720 |
| cagacacagc | acgagatgc | tgcacaacct | gaaccagcag | cgcaaaaacg | gcgggcgctt | 780 |
| ctgcgacgtg | ctcttgcggg | taggcgacga | gagcttccca | gcgcaccgcg | ccgtgctggc | 840 |

-continued

| | |
|---|---|
| cgcctgcagc gagtactttg agtcggtgtt cagcgcccag ttgggcgacg gcggagctgc | 900 |
| ggacgggggt ccggctgatg taggggggcgc gacggcagca ccaggcggcg gggccggggg | 960 |
| cagccgggag ctggagatgc acactatcag ctccaaggta tttggggaca ttctggactt | 1020 |
| cgcctacact tcccgcatcg tggtgcgctt ggagagcttt cccgaactca tgacggccgc | 1080 |
| caagttcctg ctgatgaggt cggttatcga gatctgccag gaagtcatca aacagtccaa | 1140 |
| cgtacagatc ctggtacccc ctgcccgcgc cgatataatg ctctttcgcc ccctgggac | 1200 |
| ctcggacttg ggcttccctt tggacatgac caacggggca gccttggcag ccaacagcaa | 1260 |
| tggcatcgcc ggcagcatgc agccagagga ggaggcagct cgggcggctg gtgcagccat | 1320 |
| tgcaggccaa gcctctttgc ctgtgttacc tggggtggac cgcttgccca tggtggctgg | 1380 |
| accctatcc ccccaactgc tgacttcccc attcccagt gtggcatcca gtgccctcc | 1440 |
| cctgactggc aagcgaggcc ggggccgccc aaggaaggcc aacctgctgg actcaatgtt | 1500 |
| tgggtcccca gggggcctga gggaggcagg catccttcca tgcggtctat gtggtaaggt | 1560 |
| gttcactgat gccaaccggc tccggcagca cgaggcccag cacggtgtca ccagcctcca | 1620 |
| gctgggctac atcgaccttc ctcctccgag gctgggtgag aatgggctac ccatctctga | 1680 |
| agaccccgac ggcccccgaa agaggagccg gaccaggaag caggtggctt gtgagatctg | 1740 |
| cggcaagatc ttccgtgatg tgtatcatct taaccggcac aagctgtccc actctgggga | 1800 |
| gaagccctac tcctgccctg tgtgtgggtt gcggttcaag agaaaagacc gcatgtccta | 1860 |
| ccatgtgcgg tccatgatg ggtccgtggg caagccttac atctgccaga gctgtgggaa | 1920 |
| aggcttctcc aggcctgatc acttgaacgg acatatcaag caggtgcaca cttctgagcg | 1980 |
| gcctcacaag tgtcagacct gcaatgcttc ttttgccacc cgagaccgtc tgcgctccca | 2040 |
| cctggcctgt catgaagaca aggtgccctg ccaggtgtgt gggaagtact gcgggcagc | 2100 |
| atacatggca gacccctga agaagcacag cgagggccc agcaacttct gcagtatctg | 2160 |
| taaccgaggt ttctcctctg cctcctactt aaaggtccat gttaaaaccc accacggtgt | 2220 |
| tccccttccc caggtctcca ggcaccagga gcccatcctg aatggggag cagcgttcca | 2280 |
| ctgcgccagg acctatggca caaagaagg ccagaaatgc tcacatcagg atccgattga | 2340 |
| gagctctgac tcctatggtg acctctcaga tgccagcgac ctgaagacgc cagagaagca | 2400 |
| gagtgccaat ggctctttct cctgcgacat ggcagtcccc aaaaacaaaa tggagtctga | 2460 |
| tggggagaag aagtacccat gccctgaatg tgggagcttc ttccgctcta agtcctactt | 2520 |
| gaacaaacac atccagaagg tgcatgtccg ggctctcggg ggccccctgg gggacctggg | 2580 |
| ccctgccctt ggctcacctt tctctcctca gcagaacatg tctctcctcg agtcctttgg | 2640 |
| gtttcagatt gttcagtcgg catttgcgtc atctttagta gatcctgagg ttgaccagca | 2700 |
| gcccatgggg cctgaaggga atgaggcag ctgctgtgtc cccacggaaa caaccatctg | 2760 |
| gggactgctg ggaaatgctg tgaatgcgga gggaagtgat gtttggggttc tgtagctgag | 2820 |
| agatttttat tcatttttaa ctgccccca accccactcc aactccttct ccaccaccca | 2880 |
| ttctcccaat ggtctttaga aatagatttt catctgatat tctgcagaaa tatcaatgag | 2940 |
| acttggtatg ggacaggggc agaaaacact acataggcct ccaaggcaaa accagtccca | 3000 |
| gtttctttaa tgggaagaag ctggaattcc tggtgctcaa ttcttagtga ccccaatcct | 3060 |
| atacccaaat ctatgatatt ctgggacctc agtgattttg gtccctccc acttctctag | 3120 |
| ttcgtcatcc tcccttccca tatccttcaa aagaaccaca ctagggtctc cacctactta | 3180 |
| tacaatgcgg atgcccaact gttttttaagg aagccagaag catcccatgg accatggggt | 3240 |

-continued

| | |
|---|---|
| gagtgtcctc caagagcccc ctgagctcag ccctctgcct ggagggctcc agacctttct | 3300 |
| gagccctgct tggaggcgag cattttcact gctaggacaa gctcagctgt tgaggacacc | 3360 |
| cccaccccaa atttcagttc ttacgtgatt ttaaccattc aacatgctgt tgggttttaa | 3420 |
| ttctctaatt attattatta ttgttattat tttttaggac cagttgtagt gaattgctac | 3480 |
| tgaaagctat cccaggtgat acagagctct ttgtaaaccg cagtcacaca ttagggttag | 3540 |
| tattaaactt tgtttagatg taccataatt aacttggcta gttgattgtt tgaagtctat | 3600 |
| ggaagaaata gttttatgca aaatttttaaa aaatgccagt ctggtcaggg aagtaggggg | 3660 |
| tttcaatgct gttgggaacc aggaaggtgg gacagccggc aggtagggac attgtgtacc | 3720 |
| tcagttgtgt cacatgtgag caagcccagg ttgaccttgt gatgtgaatt gatctgatca | 3780 |
| gactgtatta aaaatgttag tacattactc ta | 3812 |

<210> SEQ ID NO 19
<211> LENGTH: 3747
<212> TYPE: DNA
<213> ORGANISM: Homo sapiens

<400> SEQUENCE: 19

| | |
|---|---|
| gggcctactc tgccgccgcc gccgcccgcc cgctccagcc gccgccgccg ccgccaccgc | 60 |
| cctccaggct ccgggacccg gccgcgcca ccgcccccgt gcgcgcccg ccgccgccgc | 120 |
| cttcgccttc gccttttgtt tcctccgctc cggcgccccc gccccggctc gcgctttgca | 180 |
| ggggacgcag cgcgcgcccc cagcgggccc gggaaaagcc gcggcgcgcg cgcgcgcctg | 240 |
| cgcggcggac ccctccttct cctccccgcg tgcgcgtgcc cttcttggct gcgcgccggc | 300 |
| gccgcctggc gggcgggagg ggaggtggca ggcgcgtttg caggaggggc gcacctcttc | 360 |
| gctcgcgcac ccccccggaa ggtagaccgg gaaggggagg cgggcgggcg gagaggagag | 420 |
| agtggcgcgc agtccagcga gggcggggt tggctatgtg gggggtggtg cacccccgcag | 480 |
| tctagacagt ctgatccggg ctgggggcgt gtacactcgg cgcacctgcg agactacaga | 540 |
| gcctcgggcc ggcacgtgtg gggagtgtgg acacgtctgc tgcgccccgc ttctcgctgc | 600 |
| tgaggggaag ggagggggcg ggcaggtgca gcggccgggc tagtgggagg gggcggcggc | 660 |
| catggagcgg gtgaacgacg cttcgtgcgg cccgtctggc tgctacacat accaggtgag | 720 |
| cagacacagc acggagatgc tgcacaacct gaaccagcag cgcaaaaacg gcgggcgctt | 780 |
| ctgcgacgtg ctcttgcggg taggcgacga gagcttccca gcgcaccgcg ccgtgctggc | 840 |
| cgcctgcagc gagtactttg agtcggtgtt cagcgcccag ttgggcgacg gcggagctgc | 900 |
| ggacggggt ccggctgatg taggggggcgc gacggcagca ccaggcggcg gggccggggg | 960 |
| cagccgggag ctgagatgc acactatcag ctccaaggta tttggggaca ttctggactt | 1020 |
| cgcctacact tcccgcatcg tggtgcgctt ggagagcttt cccgaactca tgacggccgc | 1080 |
| caagttcctg ctgatgaggt cggttatcga gatctgccag gaagtcatca aacagtccaa | 1140 |
| cgtacagatc ctggtacccc ctgcccgcgc cgatataatg ctctttcgcc ccctgggac | 1200 |
| ctcggacttg ggcttcccctt tggacatgac caacgggca gccttggcag ccaacagcaa | 1260 |
| tggcatcgcc ggcagcatgc agccagagga ggaggcagct cgggcggctg gtgcagccat | 1320 |
| tgcaggccaa gcctctttgc ctgtgttacc tggggtggac cgcttgccca tggtggctgg | 1380 |
| acccctatcc ccccaactgc tgacttcccc attccccagt gtggcatcca gtgcccctcc | 1440 |
| cctgactggc aagcgaggcc ggggccgccc aaggaaggcc aacctgctgg actcaatgtt | 1500 |
| tgggtcccca gggggcctga gggaggcagg catccttcca tgcggtctat gtggtaaggt | 1560 |

```
gttcactgat gccaaccggc tccggcagca cgaggcccag cacggtgtca ccagcctcca   1620
gctgggctac atcgacctcc ctcctccgag gctgggtgag aatgggctac ccatctctga   1680
agaccccgac ggcccccgaa agaggagccg gaccaggaag caggtggctt gtgagatctg   1740
cggcaagatc ttccgtgatg tgtatcatct taaccggcac aagctgtccc actctgggga   1800
gaagccctac tcctgccctg tgtgtgggtt gcggttcaag agaaagacc gcatgtccta    1860 ccatgtgcgg tccatgatg ggtccgtggg caagccttac atctgccaga gctgtgggaa    1920
aggcttctcc aggcctgatc acttgaacgg acatatcaag caggtgcaca cttctgagcg   1980
gcctcacaag tgtcagacct gcaatgcttc ttttgccacc cgagaccgtc tgcgctccca   2040
cctggcctgt catgaagaca aggtgccctg ccaggtgtgt gggaagtact gcgggcagc    2100 atacatggca gaccacctga agaagcacag cgaggggccc agcaacttct gcagtatctg   2160
taaccgaggt ctccaggcac caggagccca tcctgaatgg gggagcagcg ttccactgcg   2220
ccaggaccta tggcaacaaa gaaggccaga aatgctcaca tcaggatccg attgagagct   2280
ctgactccta tggtgacctc tcagatgcca gcgacctgaa gacgccagag aagcagagtg   2340
ccaatggctc tttctcctgc gacatggcag tccccaaaaa caaatggag tctgatgggg    2400 agaagaagta cccatgccct gaatgtggga gcttcttccg ctctaagtcc tacttgaaca   2460
aacacatcca gaaggtgcat gtccgggctc tcggggccc cctgggggac ctgggccctg    2520
cccttggctc acctttctct cctcagcaga acatgtctct cctcgagtcc tttgggtttc   2580
agattgttca gtcggcattt gcgtcatctt tagtagatcc tgaggttgac cagcagccca   2640
tggggcctga agggaaatga ggcagctgct gtgtccccac ggaaacaacc atctggggac   2700
tgctgggaaa tgctgtgaat gcggagggaa gtgatgtttg ggttctgtag ctgagagatt   2760
tttattcatt tttaactgcc ccccaacccc actccaactc cttctccacc acccattctc   2820
ccaatggtct ttagaaatag attttcatct gatattctgc agaaatatca atgagacttg   2880
gtatgggaca ggggcagaaa acactacata ggcctccaag gcaaaaccag tcccagtttc   2940
tttaatggga agaagctgga attcctggtg ctcaattctt agtgacccca atcctatacc   3000
caaatctatg atattctggg acctcagtga ttttggtccc ctcccacttc tctagttcgt   3060
catcctccct tcccatatcc ttcaaaagaa ccacactagg gtctccacct acttatacaa   3120
tgcggatgcc caactgtttt taaggaagcc agaagcatcc catggaccat ggggtgagtg   3180
tcctccaaga gcccctgag ctcagccctc tgcctggagg gctccagacc tttctgagcc    3240
ctgcttggag gcgagcattt tcactgctag gacaagctca gctgttgagg acaccccac    3300 cccaaatttc agttcttacg tgatttaac cattcaacat gctgttgggt tttaattctc     3360
taattattat tattattgtt attattttt aggaccagtt gtagtgaatt gctactgaaa     3420
gctatcccag gtgatacaga gctctttgta aaccgcagtc acacattagg gttagtatta   3480
aactttgttt agatgtacca taattaactt ggctagttga ttgtttgaag tctatggaag   3540
aaatagtttt atgcaaaatt ttaaaaaatg ccagtctggt cagggaagta gggggtttca   3600
atgctgttgg gaaccaggaa ggtgggacag ccggcaggta gggacattgt gtacctcagt   3660
tgtgtcacat gtgagcaagc ccaggttgac cttgtgatgt gaattgatct gatcagactg   3720
tattaaaaat gttagtacat tactcta                                       3747

<210> SEQ ID NO 20
<211> LENGTH: 2582
<212> TYPE: DNA
<213> ORGANISM: Homo sapiens
```

```
<400> SEQUENCE: 20
ctatgtgggg ggtggtgcac cccgcagtct agacagtctg atccgggctg ggggcgtgta      60
cactcggcgc acctgcgaga ctacagagcc tcgggccggc acgtgtgggg agtgtggaca     120
cgtctgctgc gccccgcttc tcgctgctga ggggaaggga gggggcgggc aggtgcagcg     180
gccgggctag tgggaggggg cggcggccat ggagcgggtg aacgacgctt cgtgcggccc     240
gtctggctgc tacacatacc aggtgagcag acacagcacg gagatgctgc acaacctgaa     300
ccagcagcgc aaaaacggcg ggcgcttctg cgacgtgctc ttgcgggtag cgacgagag      360
cttcccagcg caccgcgccg tgctggccgc ctgcagcgag tactttgagt cggtgttcag     420
cgcccagttg ggcgacggcg gagctgcgga cggggtccg gctgatgtag ggggcgcgac      480
ggcagcacca ggcggcgggg ccgggggcag ccggagctg gagatgcaca ctatcagctc      540
caaggtattt ggggacattc tggacttcgc ctacacttcc cgcatcgtgg tgcgcttgga     600
gagctttccc gaactcatga cggccgccaa gttcctgctg atgaggtcgg ttatcgagat     660
ctgccaggaa gtcatcaaac agtccaacgt acagatcctg gtaccccctg cccgcgccga     720
tataatgctc tttcgcccc  ctgggacctc ggacttgggc ttccctttgg acatgaccaa     780
cggggcagcc ttggcagcca acagcaatgg catcgccggc agcatgcagc cagaggagga     840
ggcagctcgg gcggctggtg cagccattgc aggccaagcc tctttgcctg tgttacctgg     900
ggtggaccgc ttgcccatgg tggctggacc cctatccccc caactgctga cttccccatt     960
ccccagtgtg gcatccagtg cccctcccct gactggcaag cgaggccggg gccgcccaag    1020
gaaggccaac ctgctggact caatgtttgg gtccccaggg ggcctgaggg aggcaggcat    1080
ccttccatgc ggtctatgtg gtaaggtgtt cactgatgcc aaccggctcc ggcagcacga    1140
ggcccagcac ggtgtcacca gcctccagct gggctacatc gaccttcctc ctccgaggct    1200
gggtgagaat gggctaccca tctctgaaga ccccgacggc ccccgaaaga ggagccggac    1260
caggaagcag gtggcttgtg agatctgcgg caagatcttc cgtgatgtgt atcatcttaa    1320
ccggcacaag ctgtcccact ctggggagaa gccctactcc tgccctgtgt gtgggttgcg    1380
gttcaagaga aaagaccgca tgtcctacca tgtgcggtcc catgatgggt ccgtgggcaa    1440
gccttacatc tgccagagct gtgggaaagg cttctccagg cctgatcact tgaacggaca    1500
tatcaagcag gtgcacactt ctgagcggcc tcacaagtgt caggtgtggg ttgggagcag    1560
cagcggcctg ccgcccctgg aacctcttcc tagcgacctg ccatcatggg actttgccca    1620
gcctgctttg tggaggtcgt cccattcggt tcctgacacc gccttttccc tttctctaaa    1680
aaaatcattc ccagcccttg aaaacctggg cccagcacac tccagcaaca ctctcttctg    1740
cccagccccg ccgggatatc tgaggcaggg ctggaccacc ccagagggca gcaggcctt    1800
tacccagtgg cctgttggct agcctgggcc tccctggaga gggttgacag tggaagggaa    1860
caggaggggc atttggcctg agaccccgc ttttgggaga ggctagcagg gtggttcctg     1920
cccagcatgc ccagctcctc cctgggtgac tcggagtctt tcccatgtca gagcccccaa    1980
atggggtag caaggagcac ctttctggaa ccccctatag catccaagtt tctttctggg     2040
ctctcttgcc ttttcccccc tttcacagat ggcacccctg ggcatctgtc cttgcctagg    2100
tgattttgga ggttggtgcc ttcctgggaa ctagccacca gcttatctgc ttcccttccc    2160
ctggcatcac ttcccatagg cctggggttt ctagactggg gcctggccac cccttttccc    2220
actccacgag tgagtcggcc tccagagaag actggcacaa ttccaactag agtcaaccca    2280
tgctgccctc tgcccttccc actcagatct agatcctgct ttcatttctg gctagtgaag    2340
```

-continued

```
tagactttttg tgtttttgag gtttattagc aggtctgctc aggaaccaaa ctaatgagta    2400
gctttatatt gggccacccc aatatatggc tttgggggct gaaaaagcag atgtagaccc    2460
cctccctcgg atccttattg gtgtgcccett tagcactccg cagactctgc ggggtgaaca    2520
ggagtgatga taaaattttt cattctaaaa aaaaaaaaaa aaaaaaaaaa aaaaaaaaaa    2580
aa                                                                   2582
```

<210> SEQ ID NO 21
<211> LENGTH: 641
<212> TYPE: PRT
<213> ORGANISM: Homo sapiens

<400> SEQUENCE: 21

```
Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
            20                  25                  30

Gln Arg Lys Asn Gly Gly Arg Phe Cys Asp Val Leu Leu Arg Val Gly
        35                  40                  45

Asp Glu Ser Phe Pro Ala His Arg Ala Val Leu Ala Ala Cys Ser Glu
    50                  55                  60

Tyr Phe Glu Ser Val Phe Ser Ala Gln Leu Gly Asp Gly Gly Ala Ala
65                  70                  75                  80

Asp Gly Gly Pro Ala Asp Val Gly Ala Thr Ala Ala Pro Gly Gly
            85                  90                  95

Gly Ala Gly Gly Ser Arg Glu Leu Glu Met His Thr Ile Ser Ser Lys
            100                 105                 110

Val Phe Gly Asp Ile Leu Asp Phe Ala Tyr Thr Ser Arg Ile Val Val
            115                 120                 125

Arg Leu Glu Ser Phe Pro Glu Leu Met Thr Ala Ala Lys Phe Leu Leu
        130                 135                 140

Met Arg Ser Val Ile Glu Ile Cys Gln Glu Val Ile Lys Gln Ser Asn
145                 150                 155                 160

Val Gln Ile Leu Val Pro Pro Ala Arg Ala Asp Ile Met Leu Phe Arg
                165                 170                 175

Pro Pro Gly Thr Ser Asp Leu Gly Phe Pro Leu Asp Met Thr Asn Gly
            180                 185                 190

Ala Ala Leu Ala Ala Asn Ser Asn Gly Ile Ala Gly Ser Met Gln Pro
        195                 200                 205

Glu Glu Ala Ala Arg Ala Ala Gly Ala Ala Ile Ala Gly Gln Ala
    210                 215                 220

Ser Leu Pro Val Leu Pro Gly Val Asp Arg Leu Pro Met Val Ala Gly
225                 230                 235                 240

Pro Leu Ser Pro Gln Leu Leu Thr Ser Pro Phe Pro Ser Val Ala Ser
                245                 250                 255

Ser Ala Pro Pro Leu Thr Gly Lys Arg Gly Arg Gly Arg Pro Arg Lys
            260                 265                 270

Ala Asn Leu Leu Asp Ser Met Phe Gly Ser Pro Gly Gly Leu Arg Glu
        275                 280                 285

Ala Gly Ile Leu Pro Cys Gly Leu Cys Gly Lys Val Phe Thr Asp Ala
    290                 295                 300

Asn Arg Leu Arg Gln His Glu Ala Gln His Gly Val Thr Ser Leu Gln
305                 310                 315                 320

Leu Gly Tyr Ile Asp Leu Pro Pro Arg Leu Gly Glu Asn Gly Leu
                325                 330                 335
```

```
Pro Ile Ser Glu Asp Pro Asp Gly Pro Arg Lys Arg Ser Arg Thr Arg
            340                 345                 350

Lys Gln Val Ala Cys Glu Ile Cys Gly Lys Ile Phe Arg Asp Val Tyr
        355                 360                 365

His Leu Asn Arg His Lys Leu Ser His Ser Gly Glu Lys Pro Tyr Ser
    370                 375                 380

Cys Pro Val Cys Gly Leu Arg Phe Lys Arg Lys Asp Arg Met Ser Tyr
385                 390                 395                 400

His Val Arg Ser His Asp Gly Ser Val Gly Lys Pro Tyr Ile Cys Gln
                405                 410                 415

Ser Cys Gly Lys Gly Phe Ser Arg Pro Asp His Leu Asn Gly His Ile
            420                 425                 430

Lys Gln Val His Thr Ser Glu Arg Pro His Lys Cys Gln Thr Cys Asn
        435                 440                 445

Ala Ser Phe Ala Thr Arg Asp Arg Leu Arg Ser His Leu Ala Cys His
    450                 455                 460

Glu Asp Lys Val Pro Cys Gln Val Cys Gly Lys Tyr Leu Arg Ala Ala
465                 470                 475                 480

Tyr Met Ala Asp His Leu Lys Lys His Ser Glu Gly Pro Ser Asn Phe
                485                 490                 495

Cys Ser Ile Cys Asn Arg Glu Gly Gln Lys Cys Ser His Gln Asp Pro
            500                 505                 510

Ile Glu Ser Ser Asp Ser Tyr Gly Asp Leu Ser Asp Ala Ser Asp Leu
        515                 520                 525

Lys Thr Pro Glu Lys Gln Ser Ala Asn Gly Ser Phe Ser Cys Asp Met
    530                 535                 540

Ala Val Pro Lys Asn Lys Met Glu Ser Asp Gly Glu Lys Lys Tyr Pro
545                 550                 555                 560

Cys Pro Glu Cys Gly Ser Phe Phe Arg Ser Lys Ser Tyr Leu Asn Lys
                565                 570                 575

His Ile Gln Lys Val His Val Arg Ala Leu Gly Gly Pro Leu Gly Asp
            580                 585                 590

Leu Gly Pro Ala Leu Gly Ser Pro Phe Ser Pro Gln Asn Met Ser
        595                 600                 605

Leu Leu Glu Ser Phe Gly Phe Gln Ile Val Gln Ser Ala Phe Ala Ser
    610                 615                 620

Ser Leu Val Asp Pro Glu Val Asp Gln Gln Pro Met Gly Pro Glu Gly
625                 630                 635                 640

Lys

<210> SEQ ID NO 22
<211> LENGTH: 687
<212> TYPE: PRT
<213> ORGANISM: Homo sapiens

<400> SEQUENCE: 22

Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
            20                  25                  30

Gln Arg Lys Asn Gly Gly Arg Phe Cys Asp Val Leu Leu Arg Val Gly
        35                  40                  45

Asp Glu Ser Phe Pro Ala His Arg Ala Val Leu Ala Ala Cys Ser Glu
    50                  55                  60
```

-continued

```
Tyr Phe Glu Ser Val Phe Ser Ala Gln Leu Gly Asp Gly Ala Ala
 65                  70                  75                  80

Asp Gly Gly Pro Ala Asp Val Gly Gly Thr Ala Ala Pro Gly Gly
                 85                  90                  95

Gly Ala Gly Gly Ser Arg Glu Leu Glu Met His Thr Ile Ser Ser Lys
            100                 105                 110

Val Phe Gly Asp Ile Leu Asp Phe Ala Tyr Thr Ser Arg Ile Val Val
            115                 120                 125

Arg Leu Glu Ser Phe Pro Glu Leu Met Thr Ala Ala Lys Phe Leu Leu
130                 135                 140

Met Arg Ser Val Ile Glu Ile Cys Gln Glu Val Ile Lys Gln Ser Asn
145                 150                 155                 160

Val Gln Ile Leu Val Pro Pro Ala Arg Ala Asp Ile Met Leu Phe Arg
                165                 170                 175

Pro Pro Gly Thr Ser Asp Leu Gly Phe Pro Leu Asp Met Thr Asn Gly
            180                 185                 190

Ala Ala Leu Ala Ala Asn Ser Asn Gly Ile Ala Gly Ser Met Gln Pro
            195                 200                 205

Glu Glu Glu Ala Ala Arg Ala Ala Gly Ala Ala Ile Ala Gly Gln Ala
210                 215                 220

Ser Leu Pro Val Leu Pro Gly Val Asp Arg Leu Pro Met Val Ala Gly
225                 230                 235                 240

Pro Leu Ser Pro Gln Leu Leu Thr Ser Pro Phe Pro Ser Val Ala Ser
                245                 250                 255

Ser Ala Pro Pro Leu Thr Gly Lys Arg Gly Arg Gly Arg Pro Arg Lys
            260                 265                 270

Ala Asn Leu Leu Asp Ser Met Phe Gly Ser Pro Gly Gly Leu Arg Glu
            275                 280                 285

Ala Gly Ile Leu Pro Cys Gly Leu Cys Gly Lys Val Phe Thr Asp Ala
            290                 295                 300

Asn Arg Leu Arg Gln His Glu Ala Gln His Gly Val Thr Ser Leu Gln
305                 310                 315                 320

Leu Gly Tyr Ile Asp Leu Pro Pro Arg Leu Gly Glu Asn Gly Leu
                325                 330                 335

Pro Ile Ser Glu Asp Pro Asp Gly Pro Arg Lys Arg Ser Arg Thr Arg
            340                 345                 350

Lys Gln Val Ala Cys Glu Ile Cys Gly Lys Ile Phe Arg Asp Val Tyr
            355                 360                 365

His Leu Asn Arg His Lys Leu Ser His Ser Gly Glu Lys Pro Tyr Ser
            370                 375                 380

Cys Pro Val Cys Gly Leu Arg Phe Lys Arg Lys Asp Arg Met Ser Tyr
385                 390                 395                 400

His Val Arg Ser His Asp Gly Ser Val Gly Lys Pro Tyr Ile Cys Gln
                405                 410                 415

Ser Cys Gly Lys Gly Phe Ser Arg Pro Asp His Leu Asn Gly His Ile
            420                 425                 430

Lys Gln Val His Thr Ser Glu Arg Pro His Lys Cys Gln Thr Cys Asn
            435                 440                 445

Ala Ser Phe Ala Thr Arg Asp Arg Leu Arg Ser His Leu Ala Cys His
450                 455                 460

Glu Asp Lys Val Pro Cys Gln Val Cys Gly Lys Tyr Leu Arg Ala Ala
465                 470                 475                 480

Tyr Met Ala Asp His Leu Lys Lys His Ser Glu Gly Pro Ser Asn Phe
                485                 490                 495
```

```
Cys Ser Ile Cys Asn Arg Gly Phe Ser Ser Ala Ser Tyr Leu Lys Val
            500                 505                 510

His Val Lys Thr His His Gly Val Pro Leu Pro Gln Val Ser Arg His
        515                 520                 525

Gln Glu Pro Ile Leu Asn Gly Ala Ala Phe His Cys Ala Arg Thr
530                 535                 540

Tyr Gly Asn Lys Glu Gly Gln Lys Cys Ser His Gln Asp Pro Ile Glu
545                 550                 555                 560

Ser Ser Asp Ser Tyr Gly Asp Leu Ser Asp Ala Ser Asp Leu Lys Thr
                565                 570                 575

Pro Glu Lys Gln Ser Ala Asn Gly Ser Phe Ser Cys Asp Met Ala Val
            580                 585                 590

Pro Lys Asn Lys Met Glu Ser Asp Gly Glu Lys Lys Tyr Pro Cys Pro
            595                 600                 605

Glu Cys Gly Ser Phe Phe Arg Ser Lys Ser Tyr Leu Asn Lys His Ile
610                 615                 620

Gln Lys Val His Val Arg Ala Leu Gly Gly Pro Leu Gly Asp Leu Gly
625                 630                 635                 640

Pro Ala Leu Gly Ser Pro Phe Ser Pro Gln Gln Asn Met Ser Leu Leu
                645                 650                 655

Glu Ser Phe Gly Phe Gln Ile Val Gln Ser Ala Phe Ala Ser Ser Leu
            660                 665                 670

Val Asp Pro Glu Val Asp Gln Gln Pro Met Gly Pro Glu Gly Lys
            675                 680                 685

<210> SEQ ID NO 23
<211> LENGTH: 537
<212> TYPE: PRT
<213> ORGANISM: Homo sapiens

<400> SEQUENCE: 23

Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
            20                  25                  30

Gln Arg Lys Asn Gly Gly Arg Phe Cys Asp Val Leu Leu Arg Val Gly
        35                  40                  45

Asp Glu Ser Phe Pro Ala His Arg Ala Val Leu Ala Ala Cys Ser Glu
    50                  55                  60

Tyr Phe Glu Ser Val Phe Ser Ala Gln Leu Asp Gly Gly Ala Ala
65                  70                  75                  80

Asp Gly Gly Pro Ala Asp Val Gly Gly Ala Thr Ala Ala Pro Gly Gly
                85                  90                  95

Gly Ala Gly Gly Ser Arg Glu Leu Glu Met His Thr Ile Ser Ser Lys
            100                 105                 110

Val Phe Gly Asp Ile Leu Asp Phe Ala Tyr Thr Ser Arg Ile Val Val
        115                 120                 125

Arg Leu Glu Ser Phe Pro Glu Leu Met Thr Ala Ala Lys Phe Leu Leu
    130                 135                 140

Met Arg Ser Val Ile Glu Ile Cys Gln Glu Val Ile Lys Gln Ser Asn
145                 150                 155                 160

Val Gln Ile Leu Val Pro Pro Ala Arg Ala Asp Ile Met Leu Phe Arg
                165                 170                 175

Pro Pro Gly Thr Ser Asp Leu Gly Phe Pro Leu Asp Met Thr Asn Gly
            180                 185                 190
```

```
Ala Ala Leu Ala Ala Asn Ser Asn Gly Ile Ala Gly Ser Met Gln Pro
            195                 200                 205

Glu Glu Glu Ala Ala Arg Ala Ala Gly Ala Ala Ile Ala Gly Gln Ala
        210                 215                 220

Ser Leu Pro Val Leu Pro Gly Val Asp Arg Leu Pro Met Val Ala Gly
225                 230                 235                 240

Pro Leu Ser Pro Gln Leu Leu Thr Ser Pro Phe Pro Ser Val Ala Ser
            245                 250                 255

Ser Ala Pro Pro Leu Thr Gly Lys Arg Gly Arg Gly Pro Arg Lys
            260                 265                 270

Ala Asn Leu Leu Asp Ser Met Phe Gly Ser Pro Gly Leu Arg Glu
        275                 280                 285

Ala Gly Ile Leu Pro Cys Gly Leu Cys Gly Lys Val Phe Thr Asp Ala
        290                 295                 300

Asn Arg Leu Arg Gln His Glu Ala Gln His Gly Val Thr Ser Leu Gln
305                 310                 315                 320

Leu Gly Tyr Ile Asp Leu Pro Pro Arg Leu Gly Glu Asn Gly Leu
            325                 330                 335

Pro Ile Ser Glu Asp Pro Asp Gly Pro Arg Lys Arg Ser Arg Thr Arg
            340                 345                 350

Lys Gln Val Ala Cys Glu Ile Cys Gly Lys Ile Phe Arg Asp Val Tyr
        355                 360                 365

His Leu Asn Arg His Lys Leu Ser His Ser Gly Glu Lys Pro Tyr Ser
        370                 375                 380

Cys Pro Val Cys Gly Leu Arg Phe Lys Arg Lys Asp Arg Met Ser Tyr
385                 390                 395                 400

His Val Arg Ser His Asp Gly Ser Val Gly Lys Pro Tyr Ile Cys Gln
            405                 410                 415

Ser Cys Gly Lys Gly Phe Ser Arg Pro Asp His Leu Asn Gly His Ile
        420                 425                 430

Lys Gln Val His Thr Ser Glu Arg Pro His Lys Cys Gln Thr Cys Asn
        435                 440                 445

Ala Ser Phe Ala Thr Arg Asp Arg Leu Arg Ser His Leu Ala Cys His
        450                 455                 460

Glu Asp Lys Val Pro Cys Gln Val Cys Gly Lys Tyr Leu Arg Ala Ala
465                 470                 475                 480

Tyr Met Ala Asp His Leu Lys Lys His Ser Glu Gly Pro Ser Asn Phe
            485                 490                 495

Cys Ser Ile Cys Asn Arg Gly Leu Gln Ala Pro Gly Ala His Pro Glu
        500                 505                 510

Trp Gly Ser Ser Val Pro Leu Arg Gln Asp Leu Trp Gln Gln Arg Arg
        515                 520                 525

Pro Glu Met Leu Thr Ser Gly Ser Asp
        530                 535

<210> SEQ ID NO 24
<211> LENGTH: 537
<212> TYPE: PRT
<213> ORGANISM: Homo sapiens

<400> SEQUENCE: 24

Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
            20                  25                  30
```

```
Gln Arg Lys Asn Gly Gly Arg Phe Cys Asp Val Leu Leu Arg Val Gly
            35                  40                  45
Asp Glu Ser Phe Pro Ala His Arg Ala Val Leu Ala Ala Cys Ser Glu
 50                  55                  60
Tyr Phe Glu Ser Val Phe Ser Ala Gln Leu Gly Asp Gly Gly Ala Ala
 65                  70                  75                  80
Asp Gly Gly Pro Ala Asp Val Gly Gly Ala Thr Ala Ala Pro Gly Gly
            85                  90                  95
Gly Ala Gly Gly Ser Arg Glu Leu Glu Met His Thr Ile Ser Ser Lys
            100                 105                 110
Val Phe Gly Asp Ile Leu Asp Phe Ala Tyr Thr Ser Arg Ile Val Val
            115                 120                 125
Arg Leu Glu Ser Phe Pro Glu Leu Met Thr Ala Ala Lys Phe Leu Leu
            130                 135                 140
Met Arg Ser Val Ile Glu Ile Cys Gln Glu Val Ile Lys Gln Ser Asn
145                 150                 155                 160
Val Gln Ile Leu Val Pro Pro Ala Arg Ala Asp Ile Met Leu Phe Arg
            165                 170                 175
Pro Pro Gly Thr Ser Asp Leu Gly Phe Pro Leu Asp Met Thr Asn Gly
            180                 185                 190
Ala Ala Leu Ala Ala Asn Ser Asn Gly Ile Ala Gly Ser Met Gln Pro
            195                 200                 205
Glu Glu Glu Ala Ala Arg Ala Ala Gly Ala Ala Ile Ala Gly Gln Ala
            210                 215                 220
Ser Leu Pro Val Leu Pro Gly Val Asp Arg Leu Pro Met Val Ala Gly
225                 230                 235                 240
Pro Leu Ser Pro Gln Leu Leu Thr Ser Pro Phe Pro Ser Val Ala Ser
            245                 250                 255
Ser Ala Pro Pro Leu Thr Gly Lys Arg Gly Arg Gly Arg Pro Arg Lys
            260                 265                 270
Ala Asn Leu Leu Asp Ser Met Phe Gly Ser Pro Gly Gly Leu Arg Glu
            275                 280                 285
Ala Gly Ile Leu Pro Cys Gly Leu Cys Gly Lys Val Phe Thr Asp Ala
            290                 295                 300
Asn Arg Leu Arg Gln His Glu Ala Gln His Gly Val Thr Ser Leu Gln
305                 310                 315                 320
Leu Gly Tyr Ile Asp Leu Pro Pro Arg Leu Gly Glu Asn Gly Leu
            325                 330                 335
Pro Ile Ser Glu Asp Pro Asp Gly Pro Arg Lys Arg Ser Arg Thr Arg
            340                 345                 350
Lys Gln Val Ala Cys Glu Ile Cys Gly Lys Ile Phe Arg Asp Val Tyr
            355                 360                 365
His Leu Asn Arg His Lys Leu Ser His Ser Gly Glu Lys Pro Tyr Ser
            370                 375                 380
Cys Pro Val Cys Gly Leu Arg Phe Lys Arg Lys Asp Arg Met Ser Tyr
385                 390                 395                 400
His Val Arg Ser His Asp Gly Ser Val Gly Lys Pro Tyr Ile Cys Gln
            405                 410                 415
Ser Cys Gly Lys Gly Phe Ser Arg Pro Asp His Leu Asn Gly His Ile
            420                 425                 430
Lys Gln Val His Thr Ser Glu Arg Pro His Lys Cys Gln Val Trp Val
            435                 440                 445
Gly Ser Ser Ser Gly Leu Pro Pro Leu Glu Pro Leu Pro Ser Asp Leu
```

```
                450                 455                 460
Pro Ser Trp Asp Phe Ala Gln Pro Ala Leu Trp Arg Ser His Ser
465                 470                 475                 480

Val Pro Asp Thr Ala Phe Ser Leu Ser Leu Lys Lys Ser Phe Pro Ala
                485                 490                 495

Leu Glu Asn Leu Gly Pro Ala His Ser Ser Asn Thr Leu Phe Cys Pro
                500                 505                 510

Ala Pro Pro Gly Tyr Leu Arg Gln Gly Trp Thr Thr Pro Glu Gly Ser
                515                 520                 525

Arg Ala Phe Thr Gln Trp Pro Val Gly
                530                 535

<210> SEQ ID NO 25
<211> LENGTH: 537
<212> TYPE: PRT
<213> ORGANISM: Homo sapiens

<400> SEQUENCE: 25

Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
                20                  25                  30

Gln Arg Lys Asn Gly Gly Arg Phe Cys Asp Val Leu Leu Arg Val Gly
            35                  40                  45

Asp Glu Ser Phe Pro Ala His Arg Ala Val Leu Ala Ala Cys Ser Glu
        50                  55                  60

Tyr Phe Glu Ser Val Phe Ser Ala Gln Leu Gly Asp Gly Gly Ala Ala
65                  70                  75                  80

Asp Gly Gly Pro Ala Asp Val Gly Gly Ala Thr Ala Ala Pro Gly Gly
                85                  90                  95

Gly Ala Gly Gly Ser Arg Glu Leu Glu Met His Thr Ile Ser Ser Lys
            100                 105                 110

Val Phe Gly Asp Ile Leu Asp Phe Ala Tyr Thr Ser Arg Ile Val Val
        115                 120                 125

Arg Leu Glu Ser Phe Pro Glu Leu Met Thr Ala Ala Lys Phe Leu Leu
130                 135                 140

Met Arg Ser Val Ile Glu Ile Cys Gln Glu Val Ile Lys Gln Ser Asn
145                 150                 155                 160

Val Gln Ile Leu Val Pro Pro Ala Arg Ala Asp Ile Met Leu Phe Arg
                165                 170                 175

Pro Pro Gly Thr Ser Asp Leu Gly Phe Pro Leu Asp Met Thr Asn Gly
            180                 185                 190

Ala Ala Leu Ala Ala Asn Ser Asn Gly Ile Ala Gly Ser Met Gln Pro
        195                 200                 205

Glu Glu Glu Ala Ala Arg Ala Ala Gly Ala Ile Ala Gly Gln Ala
    210                 215                 220

Ser Leu Pro Val Leu Pro Gly Val Asp Arg Leu Pro Met Val Ala Gly
225                 230                 235                 240

Pro Leu Ser Pro Gln Leu Leu Thr Ser Pro Phe Pro Ser Val Ala Ser
                245                 250                 255

Ser Ala Pro Pro Leu Thr Gly Lys Arg Gly Arg Gly Arg Pro Arg Lys
            260                 265                 270

Ala Asn Leu Leu Asp Ser Met Phe Gly Ser Pro Gly Gly Leu Arg Glu
        275                 280                 285

Ala Gly Ile Leu Pro Cys Gly Leu Cys Gly Lys Val Phe Thr Asp Ala
```

```
                290                 295                 300
Asn Arg Leu Arg Gln His Glu Ala Gln His Gly Val Thr Ser Leu Gln
305                 310                 315                 320

Leu Gly Tyr Ile Asp Leu Pro Pro Arg Leu Gly Glu Asn Gly Leu
            325                 330                 335

Pro Ile Ser Glu Asp Pro Asp Gly Pro Arg Lys Arg Ser Arg Thr Arg
            340                 345                 350

Lys Gln Val Ala Cys Glu Ile Cys Gly Lys Ile Phe Arg Asp Val Tyr
            355                 360                 365

His Leu Asn Arg His Lys Leu Ser His Ser Gly Glu Lys Pro Tyr Ser
370                 375                 380

Cys Pro Val Cys Gly Leu Arg Phe Lys Arg Lys Asp Arg Met Ser Tyr
385                 390                 395                 400

His Val Arg Ser His Asp Gly Ser Val Gly Lys Pro Tyr Ile Cys Gln
            405                 410                 415

Ser Cys Gly Lys Gly Phe Ser Arg Pro Asp His Leu Asn Gly His Ile
            420                 425                 430

Lys Gln Val His Thr Ser Glu Arg Pro His Lys Cys Gln Val Trp Val
            435                 440                 445

Gly Ser Ser Gly Leu Pro Pro Leu Glu Pro Leu Pro Ser Asp Leu
450                 455                 460

Pro Ser Trp Asp Phe Ala Gln Pro Ala Leu Trp Arg Ser Ser His Ser
465                 470                 475                 480

Val Pro Asp Thr Ala Phe Ser Leu Ser Leu Lys Lys Ser Phe Pro Ala
            485                 490                 495

Leu Glu Asn Leu Gly Pro Ala His Ser Ser Asn Thr Leu Phe Cys Pro
            500                 505                 510

Ala Pro Pro Gly Tyr Leu Arg Gln Gly Trp Thr Thr Pro Glu Gly Ser
            515                 520                 525

Arg Ala Phe Thr Gln Trp Pro Val Gly
            530                 535

<210> SEQ ID NO 26
<211> LENGTH: 21
<212> TYPE: RNA
<213> ORGANISM: Artificial Sequence
<220> FEATURE:
<223> OTHER INFORMATION: FAPP2 targeted siRNA

<400> SEQUENCE: 26
gauggaucuu guuggaaauu u                                            21

<210> SEQ ID NO 27
<211> LENGTH: 21
<212> TYPE: RNA
<213> ORGANISM: Artificial Sequence
<220> FEATURE:
<223> OTHER INFORMATION: FAPP2 targeted siRNA

<400> SEQUENCE: 27
auuuccaaca agauccaucu u                                            21

<210> SEQ ID NO 28
<211> LENGTH: 21
<212> TYPE: RNA
<213> ORGANISM: Artificial Sequence
<220> FEATURE:
<223> OTHER INFORMATION: FAPP2 targeted siRNA
<220> FEATURE:
<221> NAME/KEY: misc_feature
```

```
<222> LOCATION: (20)..(21)
<223> OTHER INFORMATION: Phosphorothioate linkage between U and U

<400> SEQUENCE: 28
gauggaucuu guuggaaauu u                                              21

<210> SEQ ID NO 29
<211> LENGTH: 21
<212> TYPE: RNA
<213> ORGANISM: Artificial Sequence
<220> FEATURE:
<223> OTHER INFORMATION: FAPP2 targeted siRNA
<220> FEATURE:
<221> NAME/KEY: misc_feature
<222> LOCATION: (20)..(21)
<223> OTHER INFORMATION: Phosphorothioate linkage between U and U

<400> SEQUENCE: 29
auuuccaaca agauccaucu u                                              21

<210> SEQ ID NO 30
<211> LENGTH: 21
<212> TYPE: RNA
<213> ORGANISM: Artificial Sequence
<220> FEATURE:
<223> OTHER INFORMATION: FAPP2 targeted siRNA
<220> FEATURE:
<221> NAME/KEY: modified_base
<222> LOCATION: (3)..(3)
<223> OTHER INFORMATION: 2'-O-methyl modification
<220> FEATURE:
<221> NAME/KEY: modified_base
<222> LOCATION: (7)..(10)
<223> OTHER INFORMATION: 2'-O-methyl modification
<220> FEATURE:
<221> NAME/KEY: modified_base
<222> LOCATION: (12)..(13)
<223> OTHER INFORMATION: 2'-O-methyl modification
<220> FEATURE:
<221> NAME/KEY: modified_base
<222> LOCATION: (19)..(21)
<223> OTHER INFORMATION: 2'-O-methyl modification
<220> FEATURE:
<221> NAME/KEY: misc_feature
<222> LOCATION: (20)..(21)
<223> OTHER INFORMATION: Phosphorothioate linkage between U and U

<400> SEQUENCE: 30
gauggaucuu guuggaaauu u                                              21

<210> SEQ ID NO 31
<211> LENGTH: 21
<212> TYPE: RNA
<213> ORGANISM: Artificial Sequence
<220> FEATURE:
<223> OTHER INFORMATION: FAPP2 targeted siRNA
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (20)..(21)
<223> OTHER INFORMATION: Phosphorothioate linkage between U and U

<400> SEQUENCE: 31
auuuccaaca agauccaucu u                                              21
```

```
<210> SEQ ID NO 32
<211> LENGTH: 21
<212> TYPE: RNA
<213> ORGANISM: Artificial Sequence
<220> FEATURE:
<223> OTHER INFORMATION: PATZ1 targeted siRNA

<400> SEQUENCE: 32
gucuauggaa gaaauaguuu u                                              21

<210> SEQ ID NO 33
<211> LENGTH: 21
<212> TYPE: RNA
<213> ORGANISM: Artificial Sequence
<220> FEATURE:
<223> OTHER INFORMATION: PATZ1 targeted siRNA

<400> SEQUENCE: 33
uuacuacuac uacuacuacu u                                              21

<210> SEQ ID NO 34
<211> LENGTH: 21
<212> TYPE: RNA
<213> ORGANISM: Artificial Sequence
<220> FEATURE:
<223> OTHER INFORMATION: PATZ1 targeted siRNA
<220> FEATURE:
<221> NAME/KEY: misc_feature
<222> LOCATION: (20)..(21)
<223> OTHER INFORMATION: Phosphorothioate linkage between U and U

<400> SEQUENCE: 34
gucuauggaa gaaauaguuu u                                              21

<210> SEQ ID NO 35
<211> LENGTH: 21
<212> TYPE: RNA
<213> ORGANISM: Artificial Sequence
<220> FEATURE:
<223> OTHER INFORMATION: PATZ1 targeted siRNA
<220> FEATURE:
<221> NAME/KEY: misc_feature
<222> LOCATION: (20)..(21)
<223> OTHER INFORMATION: Phosphorothioate linkage between U and U

<400> SEQUENCE: 35
uuacuacuac uacuacuacu u                                              21

<210> SEQ ID NO 36
<211> LENGTH: 22
<212> TYPE: RNA
<213> ORGANISM: Artificial Sequence
<220> FEATURE:
<223> OTHER INFORMATION: PATZ1 targeted siRNA
<220> FEATURE:
<221> NAME/KEY: modified_base
<222> LOCATION: (2)..(4)
<223> OTHER INFORMATION: 2'-O-methyl modification
<220> FEATURE:
<221> NAME/KEY: modified_base
<222> LOCATION: (6)..(6)
<223> OTHER INFORMATION: 2'-O-methyl modification
<220> FEATURE:
<221> NAME/KEY: modified_base
<222> LOCATION: (15)..(15)
<223> OTHER INFORMATION: 2'-O-methyl modification
<220> FEATURE:
<221> NAME/KEY: modified_base
<222> LOCATION: (18)..(20)
<223> OTHER INFORMATION: 2'-O-methyl modification
<220> FEATURE:
<221> NAME/KEY: misc_feature
```

```
<222> LOCATION: (20)..(21)
<223> OTHER INFORMATION: Phosphorothioate linkage between U and U

<400> SEQUENCE: 36
gucuauggaa gaaauaguuu su                                             22

<210> SEQ ID NO 37
<211> LENGTH: 21
<212> TYPE: RNA
<213> ORGANISM: Artificial Sequence
<220> FEATURE:
<223> OTHER INFORMATION: PATZ1 targeted siRNA
<220> FEATURE:
<221> NAME/KEY: misc_feature
<222> LOCATION: (2)..(2)
<223> OTHER INFORMATION: 2'-O-methyl modification
<220> FEATURE:
<221> NAME/KEY: misc_feature
<222> LOCATION: (5)..(5)
<223> OTHER INFORMATION: 2'-O-methyl modification
<220> FEATURE:
<221> NAME/KEY: misc_feature
<222> LOCATION: (8)..(8)
<223> OTHER INFORMATION: 2'-O-methyl modification
<220> FEATURE:
<221> NAME/KEY: misc_feature
<222> LOCATION: (11)..(11)
<223> OTHER INFORMATION: 2'-O-methyl modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification
<220> FEATURE:
<221> NAME/KEY: misc_feature
<222> LOCATION: (20)..(21)
<223> OTHER INFORMATION: Phosphorothioate linkage between U and U

<400> SEQUENCE: 37
uuacuacuac uacuacuacu u                                              21

<210> SEQ ID NO 38
<211> LENGTH: 75
<212> TYPE: DNA
<213> ORGANISM: Artificial Sequence
<220> FEATURE:
<223> OTHER INFORMATION: Ribozyme synthesized by IDT containing the
      restriction enzyme sites Bam HI and Mlu I (RzFAPP-1)

<400> SEQUENCE: 38
aataaaggat ccatttcaca agaagccaac cagagaaaca cacgttgtgg tatattacct    60
ggtacgcgta acaat                                                    75

<210> SEQ ID NO 39
<211> LENGTH: 75
<212> TYPE: DNA
<213> ORGANISM: Artificial Sequence
<220> FEATURE:
<223> OTHER INFORMATION: Hairpin ribozyme synthesized by IDT containing
      the restriction enzyme sites Bam HI and Mlu I

<400> SEQUENCE: 39
attgttacgc gtaccaggta ataccaca acgtgtgttt ctctggttgg cttcttgtga      60
aatggatcct ttatt                                                    75

<210> SEQ ID NO 40
<211> LENGTH: 75
```

```
<212> TYPE: DNA
<213> ORGANISM: Artificial Sequence
<220> FEATURE:
<223> OTHER INFORMATION: Hairpin ribozyme synthesized by IDT containing
      the restriction enzyme sites Bam HI and Mlu I

<400> SEQUENCE: 40
aataaaggat ccttagattt agaaacttac cagagaaaca cacgttgtgg tatattacct    60
ggtacgcgta acaat                                                    75

<210> SEQ ID NO 41
<211> LENGTH: 75
<212> TYPE: DNA
<213> ORGANISM: Artificial Sequence
<220> FEATURE:
<223> OTHER INFORMATION: Hairpin ribozyme synthesized by IDT containing
      the restriction enzyme sites Bam HI and Mlu I

<400> SEQUENCE: 41
attgttacgc gtaccaggta ataccaca acgtgtgttt ctctggtaag tttctaaatc      60
taaggatcct ttatt                                                    75

<210> SEQ ID NO 42
<211> LENGTH: 75
<212> TYPE: DNA
<213> ORGANISM: Artificial Sequence
<220> FEATURE:
<223> OTHER INFORMATION: Disabled ribozyme

<400> SEQUENCE: 42
aataaaggat ccttagattt agaaacttac cagagcgtca cacgttgtgg tatattacct    60
ggtacgcgta acaat                                                    75

<210> SEQ ID NO 43
<211> LENGTH: 75
<212> TYPE: DNA
<213> ORGANISM: Artificial Sequence
<220> FEATURE:
<223> OTHER INFORMATION: Disabled ribozyme

<400> SEQUENCE: 43
attgttacgc gtaccaggta ataccaca acgtgtgacg ctctggtaag tttctaaatc      60
taaggatcct ttatt                                                    75

<210> SEQ ID NO 44
<211> LENGTH: 21
<212> TYPE: RNA
<213> ORGANISM: Artificial Sequence
<220> FEATURE:
<223> OTHER INFORMATION: Randomized control siRNA
<220> FEATURE:
<221> NAME/KEY: modified_base
<222> LOCATION: (2)..(2)
<223> OTHER INFORMATION: 2'-O-methyl modification
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (8)..(8)
<223> OTHER INFORMATION: 2'-O-methyl modification
<220> FEATURE:
<221> NAME/KEY: modified_base
<222> LOCATION: (11)..(11)
<223> OTHER INFORMATION: 2'-O-methyl modification
<220> FEATURE:
<221> NAME/KEY: modified_base
```

```
<222> LOCATION: (14)..(14)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (20)..(20)
<223> OTHER INFORMATION: 2'-O-methyl modification

<400> SEQUENCE: 44
guaguaguag uaguaguaau u                                         21

<210> SEQ ID NO 45
<211> LENGTH: 21
<212> TYPE: RNA
<213> ORGANISM: Artificial Sequence
<220> FEATURE:
<223> OTHER INFORMATION: Randomized control siRNA: antisense
<220> FEATURE:
<221> NAME/KEY: modified_base
<222> LOCATION: (2)..(2)
<223> OTHER INFORMATION: 2'-O-methyl modification
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (8)..(8)
<223> OTHER INFORMATION: 2'-O-methyl modification
<220> FEATURE:
<221> NAME/KEY: modified_base
<222> LOCATION: (11)..(11)
<223> OTHER INFORMATION: 2'-O-methyl modification
<220> FEATURE:
<221> NAME/KEY: modified_base
<222> LOCATION: (14)..(14)
<223> OTHER INFORMATION: 2'-O-methyl modification
<220> FEATURE:
<221> NAME/KEY: modified_base
<222> LOCATION: (17)..(17)
<223> OTHER INFORMATION: 2'-O-methyl modification
<220> FEATURE:
<221> NAME/KEY: misc_feature
<222> LOCATION: (20)..(21)
<223> OTHER INFORMATION: Phosphorothioate linkage

<400> SEQUENCE: 45
uuacuacuac uacuacuacu u                                         21

<210> SEQ ID NO 46
<211> LENGTH: 21
<212> TYPE: DNA
<213> ORGANISM: Artificial Sequence
<220> FEATURE:
<223> OTHER INFORMATION: luc siRNA
<220> FEATURE:
<221> NAME/KEY: modified_base
<222> LOCATION: (1)..(3)
<223> OTHER INFORMATION: 2'-O-methyl modification
<220> FEATURE:
<221> NAME/KEY: modified_base
<222> LOCATION: (5)..(5)
<223> OTHER INFORMATION: 2'-O-methyl modification
<220> FEATURE:
<221> NAME/KEY: modified_base
<222> LOCATION: (7)..(8)
<223> OTHER INFORMATION: 2'-O-methyl modification
<220> FEATURE:
<221> NAME/KEY: modified_base
```

```
<222> LOCATION: (12)..(12)
<223> OTHER INFORMATION: 2'-O-methyl modification
<220> FEATURE:
<221> NAME/KEY: modified_base
<222> LOCATION: (14)..(17)
<223> OTHER INFORMATION: 2'-O-methyl modification
<220> FEATURE:
<221> NAME/KEY: modified_base
<222> LOCATION: (20)..(21)
<223> OTHER INFORMATION: Phosphorothioate linkage
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxythymidine

<400> SEQUENCE: 46
cuuacgcuga guacuucgat t                                              21

<210> SEQ ID NO 47
<211> LENGTH: 21
<212> TYPE: DNA
<213> ORGANISM: Artificial Sequence
<220> FEATURE:
<223> OTHER INFORMATION: luc siRNA
<220> FEATURE:
<221> NAME/KEY: modified_base
<222> LOCATION: (7)..(7)
<223> OTHER INFORMATION: 2'-O-methyl modification
<220> FEATURE:
<221> NAME/KEY: modified_base
<222> LOCATION: (11)..(11)
<223> OTHER INFORMATION: 2'-O-methyl modification
<220> FEATURE:
<221> NAME/KEY: modified_base
<222> LOCATION: (16)..(16)
<223> OTHER INFORMATION: 2'-O-methyl modification
<220> FEATURE:
<221> NAME/KEY: modified_base
<222> LOCATION: (20)..(20)
<223> OTHER INFORMATION: Deoxythymidine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (21)..(21)
<223> OTHER INFORMATION: Deoxythymidine

<400> SEQUENCE: 47
ucgaaguacu cagcguaagt t                                              21

<210> SEQ ID NO 48
<211> LENGTH: 20
<212> TYPE: DNA
<213> ORGANISM: Artificial Sequence
<220> FEATURE:
<223> OTHER INFORMATION: FAPP2 Fwd Primer

<400> SEQUENCE: 48
acatcaggat ccgattgaga                                                20

<210> SEQ ID NO 49
<211> LENGTH: 19
<212> TYPE: DNA
<213> ORGANISM: Artificial Sequence
<220> FEATURE:
<223> OTHER INFORMATION: FAPP2 Rev primer

<400> SEQUENCE: 49
```
atgcaccttc tggatgtgt                                                    19

<210> SEQ ID NO 50
<211> LENGTH: 20
<212> TYPE: DNA
<213> ORGANISM: Artificial Sequence
<220> FEATURE:
<223> OTHER INFORMATION: GAPDH Fwd primer

<400> SEQUENCE: 50
gagtcaacgg atttggtcgt                                                   20

<210> SEQ ID NO 51
<211> LENGTH: 20
<212> TYPE: DNA
<213> ORGANISM: Artificial Sequence
<220> FEATURE:
<223> OTHER INFORMATION: GAPDH Rev primer

<400> SEQUENCE: 51
ttgattttgg agggatctcg                                                   20

<210> SEQ ID NO 52
<211> LENGTH: 21
<212> TYPE: RNA
<213> ORGANISM: Artificial Sequence
<220> FEATURE:
<223> OTHER INFORMATION: PATZ1 siRNA

<400> SEQUENCE: 52
gucuauggaa gaaauaguuu u                                                 21

<210> SEQ ID NO 53
<211> LENGTH: 21
<212> TYPE: RNA
<213> ORGANISM: Artificial Sequence
<220> FEATURE:
<223> OTHER INFORMATION: PATZ1  antisense siRNA

<400> SEQUENCE: 53
aacuauuucu uccauagacu u                                                 21

<210> SEQ ID NO 54
<211> LENGTH: 23
<212> TYPE: RNA
<213> ORGANISM: Artificial Sequence
<220> FEATURE:
<223> OTHER INFORMATION: randomized control siRNA

<400> SEQUENCE: 54
cuauauccua guaugaguca auu                                               23

<210> SEQ ID NO 55
<211> LENGTH: 21
<212> TYPE: RNA
<213> ORGANISM: Artificial Sequence
<220> FEATURE:
<223> OTHER INFORMATION: randomized control antisense siRNA

<400> SEQUENCE: 55
gacucauacu aggauauagu u                                                 21